US007914738B2

(12) United States Patent
Hutchins et al.

(10) Patent No.: US 7,914,738 B2
(45) Date of Patent: Mar. 29, 2011

(54) CELL BLOCK CASSETTE AND FILTER ASSEMBLY

(75) Inventors: Timothy Hutchins, Attleboro Falls, MA (US); Hal Watts, Holden, MA (US); Steven A. Scampini, Groton, MA (US); Eric Grimes, Hudson, MA (US)

(73) Assignee: Cytyc Corporation, Marlborough, MA (US)

( * ) Notice: Subject to any disclaimer, the term of this patent is extended or adjusted under 35 U.S.C. 154(b) by 328 days.

(21) Appl. No.: 11/839,533

(22) Filed: Aug. 15, 2007

(65) Prior Publication Data

US 2008/0057573 A1     Mar. 6, 2008

Related U.S. Application Data

(60) Provisional application No. 60/822,449, filed on Aug. 15, 2006, provisional application No. 60/863,941, filed on Nov. 1, 2006.

(51) Int. Cl.
*G01N 21/00* (2006.01)

(52) U.S. Cl. .............. 422/63; 422/64; 422/65; 422/66; 422/67; 435/40.5; 435/40.52; 436/180

(58) Field of Classification Search ............. 422/63–67; 435/40.5, 40.52; 436/180
See application file for complete search history.

(56) References Cited

U.S. PATENT DOCUMENTS

| | | | | |
|---|---|---|---|---|
| 4,678,559 | A | * | 7/1987 | Szabados ...................... 209/17 |
| 5,234,585 | A | * | 8/1993 | Zuk, Jr. ......................... 210/188 |
| 5,817,032 | A | | 10/1998 | Williamson, IV et al. |
| 6,913,152 | B2 | * | 7/2005 | Zuk, Jr. ......................... 210/406 |
| 6,913,921 | B2 | | 7/2005 | Fischer |
| 7,541,161 | B2 | * | 6/2009 | Fischer ....................... 435/40.5 |
| 2004/0069714 | A1 | | 4/2004 | Ferguson |

FOREIGN PATENT DOCUMENTS

EP     0448837     10/1991

OTHER PUBLICATIONS

International Search Report for PCT/US2007/076052, Form PCT/ISA/220 and 210, Applicant Cytyc Corporation, mailed Feb. 1, 2008 (7 pages).
Written Opinion of the International Searching Authority for PCT/US2007/076052, Form PCT/ISA/237, Applicant Cytyc Corporation, mailed Feb. 1, 2008 (6 pages).

* cited by examiner

*Primary Examiner* — Jyoti Nagpaul
(74) *Attorney, Agent, or Firm* — Vista IP Law Group LLP

(57) ABSTRACT

A system for making cell blocks includes a cell block cassette and processing station, the cassette including a main body having a having a collection aperture formed therein and a filter assembly removably attached to the main body, the filter assembly defining a collection well in communication with the collection aperture, and having a filter positioned across a bottom surface of the collection well, the filter configured to retain cellular matter carried in a fluid that is dispensed into the collection well and flows across the filter. The cell block processor has a cassette interface removably seating the cell block cassette, and a sensor positioned or positionable to detect and monitor a fluid level in the collection well. The processing station includes an automated fluid delivery system operable to dispense a fluid into the collection well, and a controller operatively coupled to the fluid delivery system, wherein the controller causes the fluid delivery system to selectively dispense fluids into the collection well based at least in part on a flow rate across the filter determined at least in part based on changes in the monitored fluid level in the collection well.

17 Claims, 43 Drawing Sheets

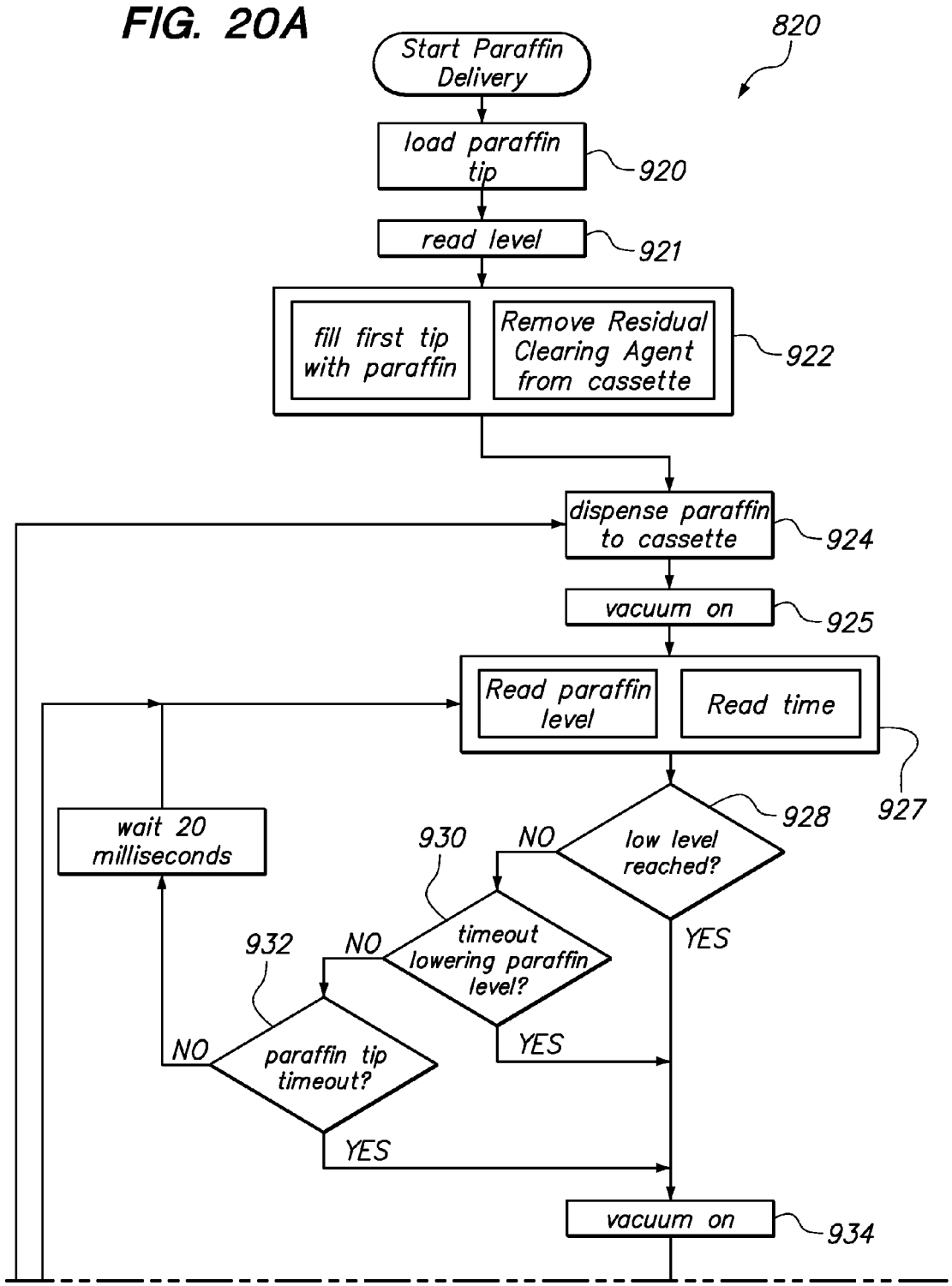

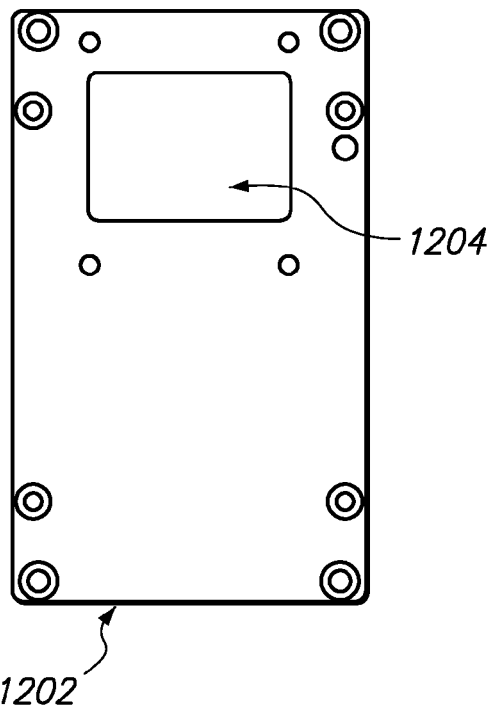
FIG. 31
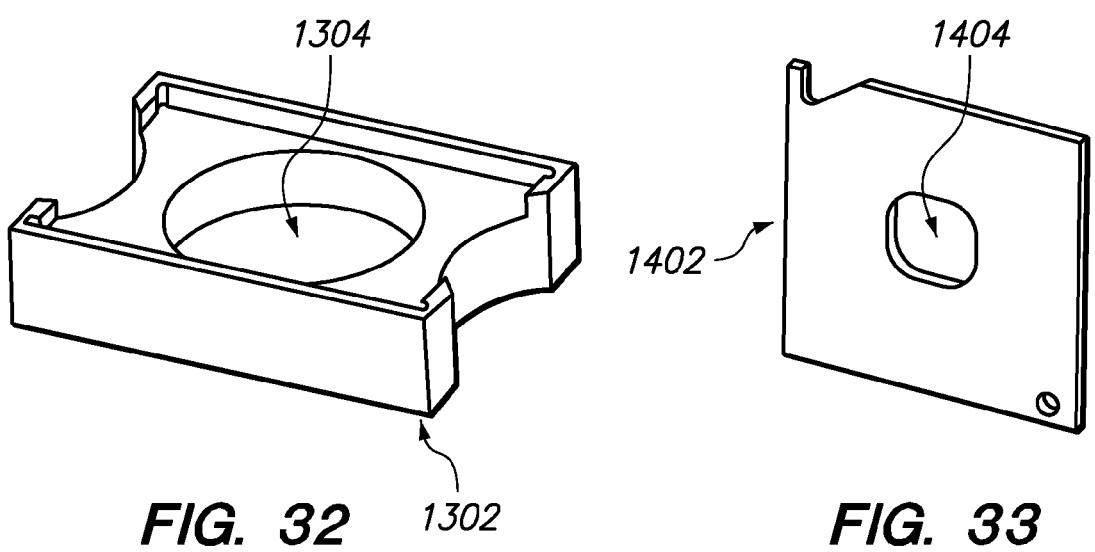
FIG. 32
FIG. 33

CELL BLOCK CASSETTE AND FILTER ASSEMBLY

RELATED APPLICATION DATA

The present application claims the benefit under 35 U.S.C. §119 to U.S. Provisional Patent Applications Ser. Nos. 60/822,449, filed on Aug. 15, 2006, and 60/863,941, filed on Nov. 1, 2006. The foregoing provisional applications are each incorporated by reference into the present application in their entirety.

FIELD OF THE INVENTION

The present inventions pertain to systems and methods for preparing cells for microscopic examination, and more particularly to automated and semi-automated systems and methods for embedding cellular materials and tissue fragments within a paraffin substrate that may be thereafter thinly-cut using a standard microtome, for microscope examination.

BACKGROUND

It is useful for diagnosing or detecting a disease process to perform a histologic or cytologic examination of a tissue cell sample using a light microscope. This requires that a tissue (cellular material) sample must first be retrieved from the patient, and then processed for microscopic examination. A number of minimally invasive techniques are available for retrieving and collecting cell samples from a patient, e.g., by using a fine needle aspiration biopsy, or by brushing body cavity surfaces accessible through minimally invasive endoscopic techniques. A variety of cell sample processing techniques are also known, such as the Cytospin® technique and the Thin-prep® technique, for depositing cellular materials and tissue fragments directly onto a microscope slide. Another technique, commonly referred to as a cell block preparation, immobilizes cellular materials and/or small tissue fragments within a solid support structure, typically paraffin. Thin sections of the cell block are then cut with a microtome and mounted onto a microscope slide for examination.

U.S. Pat. No. 6,913,921 discloses and describes methods and apparatus for cell block preparation, including providing a tissue collection cassette that serves a dual function of capturing cellular sample matter and providing a fluid pathway through which the cell processing and embedding reagents can flow. The cellular sample material is provided in an aqueous solution or a liquid cell preservative, which is passed through the tissue cassette across a filter that traps the cells and tissue fragments. A reagent flow pathway is configured to sequentially pass embedding reagents (alcohol, xylene, eosin stain) and liquefied paraffin through the tissue cassette and the cell sample already deposited on the filter. Once the paraffin is cooled, the filter is peeled away, leaving a paraffin "disk" protruding from the tissue cassette, with embedded cellular matter positioned at the end of the disk in a plane at which a tissue section can be cut using a standard microtome for microscope examination.

While representing an improvement over the then-state of the art for cell block preparation, the methods and apparatus disclosed in the '921 patent remain labor intensive, requiring manual operation and supervision, in particular, for determining when a sufficient quantity of cellular material has been gathered on the filter. Further, the cell sample fluid "pathway" (tubing and sample port) must be replaced following each use to avoid contamination of subsequent samples, and the filter-to-cassette connection relies on a relatively thick o-ring in order to create a sufficient length of paraffin cell block for later microtome slicing.

SUMMARY OF THE DISCLOSED INVENTIONS

Systems and methods are disclosed herein for the efficient creation of paraffin-embedded cell blocks, including several improvements over the methods and the apparatus disclosed in U.S. Pat. No. 6,913,921, such as (but not limited to) substantially automated cell block creation that does not require human oversight, an innovative two-piece cassette and filter assembly, more consistent cellular matter quantities in the created cell blocks, shorter processing time, reduced use of hazardous reagents, and more fully encapsulated cell blocks to preserve nucleic acid integrity.

In an exemplary embodiment, a cell block preparation system includes a two-piece cell block cassette, a cell block processing station and a finishing station. The cell block cassette includes a main cassette body having a collection aperture formed therein, and a filter assembly removably attached to the main cassette body and defining a sample collection well in communication with the collection aperture. A filter positioned across a bottom surface of the collection well is configured to retain cellular matter (e.g., cervical cells) carried in a sample fluid (e.g., preservative solution) that is dispensed into the collection well and flows across the filter. In embodiments disclosed herein, the filter assembly comprises a single-piece housing having a base portion forming the sealing surface, and a neck portion extending from the base portion. The neck portion of the filter assembly housing defines a perimeter of the collection well and has a top end that makes an interference fit with an annular grove located in a bottom surface of the main cassette body in order to detachably attach the filter assembly to the main cassette body. The filter assembly housing further comprises a filter support retention portion extending from an underside of the base portion, with a thermally conductive porous filter support member (e.g., a sintered metal disc or a metal screen) retained therein, the filter being positioned atop the filter support member within the collection well. The base portion sealing surface slopes at a downward angle from the neck portion, such that an outermost edge of the sealing surface extends to (or beyond) an outermost edge of the filter support retention portion in order to form a seal with the waste chamber interface (described below) on the processing station.

The processing station has a cassette interface that removably seats the cell block cassette, with a sensor (e.g., an ultrasound sensor) positioned or positionable to detect a fluid level in the sample collection well from which the flow rate across the filter (which is related to the amount of cellular material retained on the filter surface) may be calculated. A waste chamber compartment underlies the cassette interface, the filter assembly sealing surface sealably engaging waste chamber interface when the cell block cassette is seated (and latched) in the cassette interface. Respective pressurized air and vacuum sources may be selectively placed in communication with the interior of the waste chamber, so as to force air back through the filter and into the collection well; or alternatively to draw air, fluid, or both, from collection well, through the filter, and into the waste chamber interior. The sample fluid is drawn across the filter with the assistance of the vacuum, which may be interrupted for administering back air pressure pulses to momentarily push the cellular material away from the filter surface and allow for fluid in the collection well to drain.

The processing station includes an automated fluid delivery system and a controller that causes the fluid delivery system to dispense sample fluid from a sample vial into the cell block cassette collection well. In one embodiment, the automated fluid delivery system comprises an automated arm assembly including a pipette tip holder configured to selectively retrieve, carry and dispose of pipette tips. A suction source is coupled to the pipette tip holder, such that an open proximal end of a pipette tip held by the pipette tip holder may be selectively connected to the suction source for aspirating sample fluid, and liquefied paraffin. The processing station is equipped with empty (sterile) pipette tips, a sample vial interface for holding a sample vial containing cellular material suspended in a liquid carrier, a supply of liquefied paraffin (e.g., a heated paraffin bath), and liquid reagent sources (e.g., xylene and isopropyl alcohol), which are each also connected to the pipette holder for being dispensed through a pipette tip into the sample collection well.

For cell block processing, the automated arm assembly is configured to selectively retrieve a pipette tip, position the retrieved pipette tip to aspirate fluid from a sample vial seated in the sample vial interface, and then dispense the drawn sample fluid into the sample collection well. The controller monitors a fluid level in the collection well as a function of time and, based on the fixed dimensions of the collection well, the controller calculates a flow rate across the filter based on the fluid level output signals received from the sensor. The sensor is preferably fixed relative to the cassette interface, with the automated arm assembly being movable relative to the sensor. In the case of using an ultrasonic sensor, the sensor should be directed orthogonally to the fluid surface in the collection well for accurate time of flight reflection readings. Depending on the calculated fluid flow rate across the filter, the controller causes the automated arm assembly to continue to draw and dispense sample fluid from the sample vial into the collection well, respectively, until the flow rate (even with occasional back air pressure "burping" through the filter) is such that the controller determines a desired threshold amount of cellular material has been deposited on the filter. Notably, the cell blocks may additionally include larger tissue fragments manually placed on the filter and then augmented by aspiration of additional cellular material from the sample fluid.

Once the controller determines that desired threshold amount of cellular material has been deposited on the filter, liquid reagents are selectively dispensed through the same pipette tip into the collection well to treat the retained cellular material, after which the automated arm assembly discards the pipette tip used to dispense the sample fluid, and retrieves a new pipette tip to draw and dispense liquefied paraffin into the collection well to embed the retained cellular matter in paraffin. The paraffin is allowed to cool (and preferably affirmatively chilled), and the cassette is then removed from the cell processor. The filter assembly is removed from the cassette, leaving the paraffin-embedded cellular material attached to and sticking out the collection aperture of the main cassette body. In may be preferable to chill the already solidified paraffin in order to thermally contract the paraffin prior to separately the filter assembly. The embedded cellular material (while still attached to the cassette) is then placed atop of (in direct contact with) an additional piece of paraffin in a thermally conductive mold configured to seat the main cassette body. The mold is then heated to soften and at least partially blend together the embedding paraffin and additional paraffin, without being heated to the point of softening or liquefying the embedding paraffin such that the retained cellular material therein breaks apart and disburses through the embedding paraffin. The mold is then quickly and controllably cooled to bond the "additional" and embedding paraffin.

Other and further aspects and embodiments of the disclosed inventions are described in the detailed description of the accompanying drawings.

BRIEF DESCRIPTION OF THE DRAWINGS

It will be appreciated that the system and apparatus shown in the drawings are not necessarily drawn to scale, with emphasis instead being placed on illustrating the various aspects and features of the illustrated embodiments, in which:

FIGS. 20A-B is a flow chart of the paraffin delivery process used for creating a new cell block.

FIG. 31 is a representation of one embodiment of a heatsink top plate.

FIG. 32 is a representation of one embodiment of a cassette holder.

FIG. 33 is a representation of one embodiment of a clamp plate.

DETAILED DESCRIPTION OF THE ILLUSTRATED EMBODIMENTS

Systems and methods of embodiments of the present invention provide substantially automated creation of paraffin-embedded cell blocks by employing an automated arm in conjunction with a controlled vacuum to deposit a layer of cellular material (e.g., cervical cells obtained form a typical Pap smear) on a removable cell block cassette filter, infiltrate the deposited cellular matter with stain, reagents and paraffin, and then encapsulate the embedded cellular matter with additional paraffin.

Figure 1:
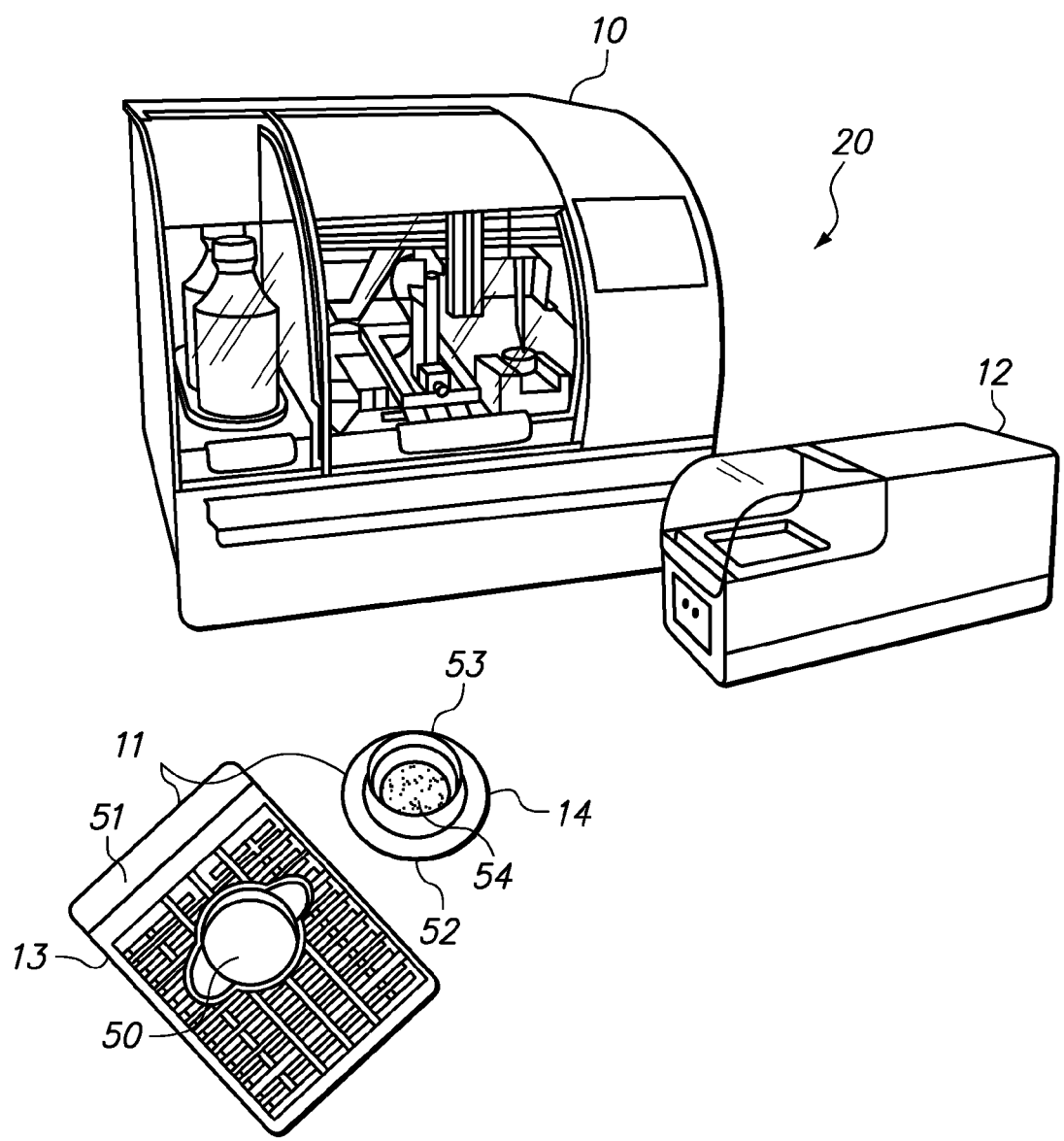
FIG. 1 is a perspective view a cell block preparation system including a processing station, a cell block cassette with detachable filter, and a finishing station, constructed according to exemplary embodiments of the disclosed inventions.
Figure 2:
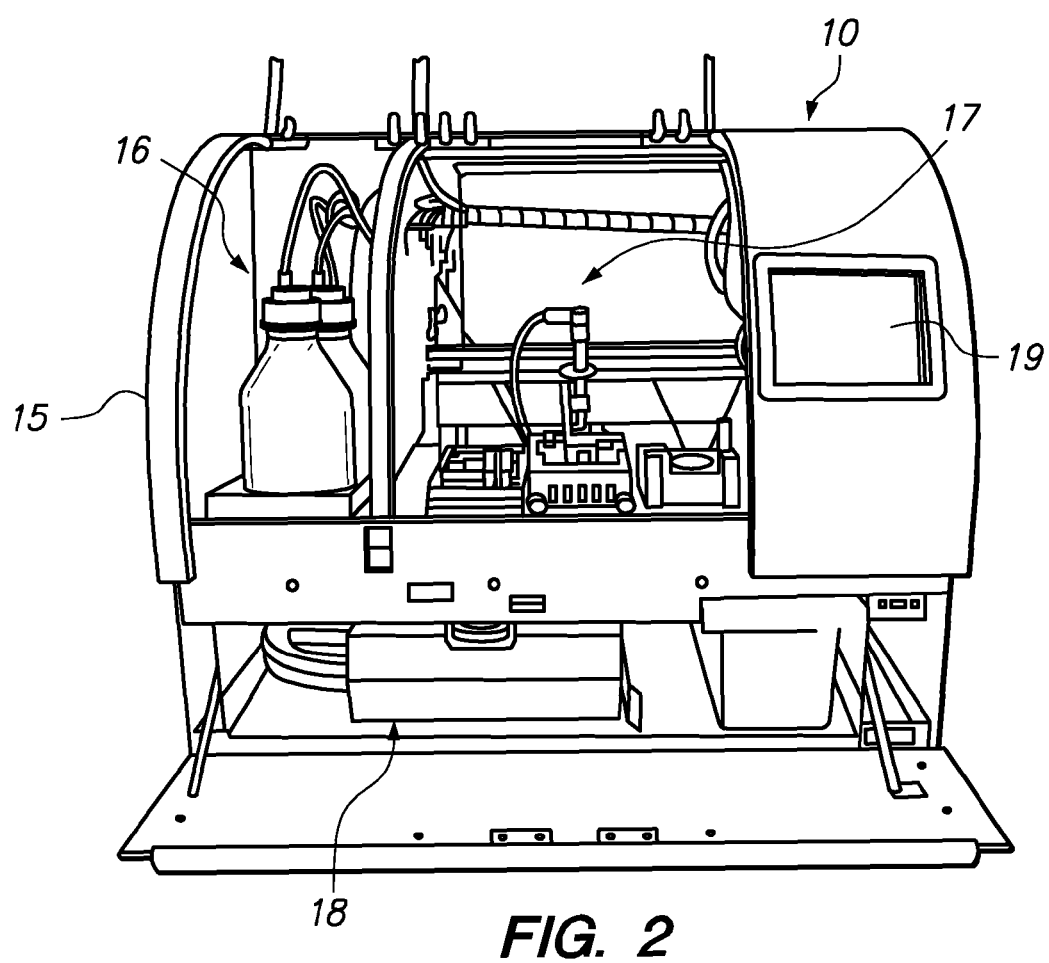
FIG. 2 is a front perspective view of the processing station, with its cabinet doors open to reveal its interior compartments and contents.

FIG. 1. depicts the main components of an exemplary cell block processing system 20, including a cell block processing station 10, a two-piece cell block cassette 11 (including a main cassette body 13 and a detachable filter assembly 14) which captures the captures the cellular material and guides infusion of the reagents and paraffin, and a finishing station 12 for encapsulating a newly created cell block in additional paraffin in preparation for later cutting and slide preparation. As seen in FIG. 2, the cell block processing station 10 includes a reagent compartment 16, process compartment 17 and waste compartment 18 provided in a single housing cabinet 15. A controller (not shown) including a computer processor and associated memory is housed within one side of the process compartment 17, and is operatively coupled with a user interface touch screen 19 located on a front exterior surface of the cabinet 15. the user interface is preferably provided in multiple possible languages and formats, as is well-known in the art of user interfaces.

Figure 3:
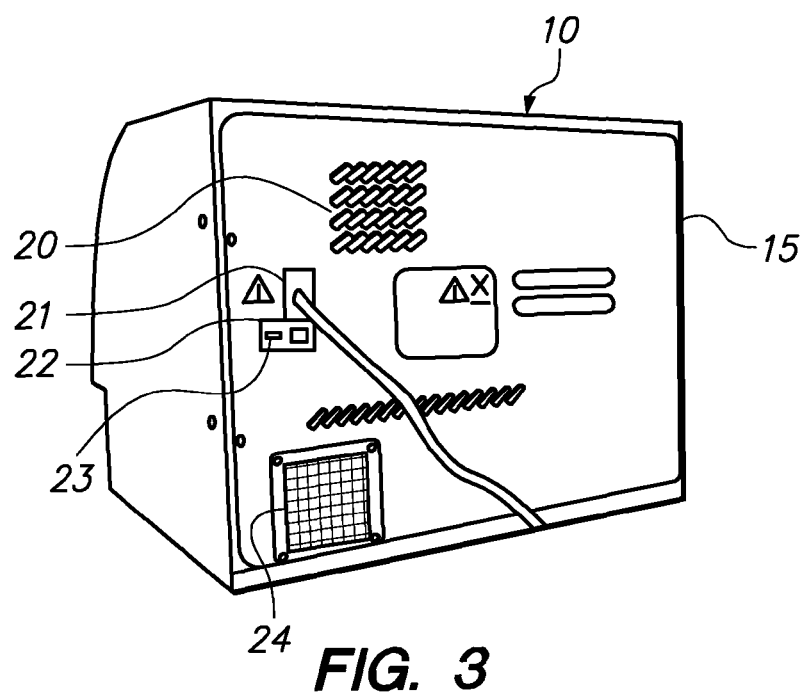
FIG. 3 is a side-rear perspective view of the processing station.

Referring to FIG. 3, the back side of the processing station cabinet 15 is preferably ventilated 20 to release heat generated by the interior electronics. A main power on/off switch 21 is located on the back side of the cabinet, although other locations may be used, if so desired. Respective ethernet and USB ports 22 and 23 are also provided on the back side of the cabinet 15. The interior cabinet chambers are preferably fume ventilated using a charcoal-activated filter, which may be accessed through the filter cover piece 24 on the back of the cabinet 15.

Figure 4:
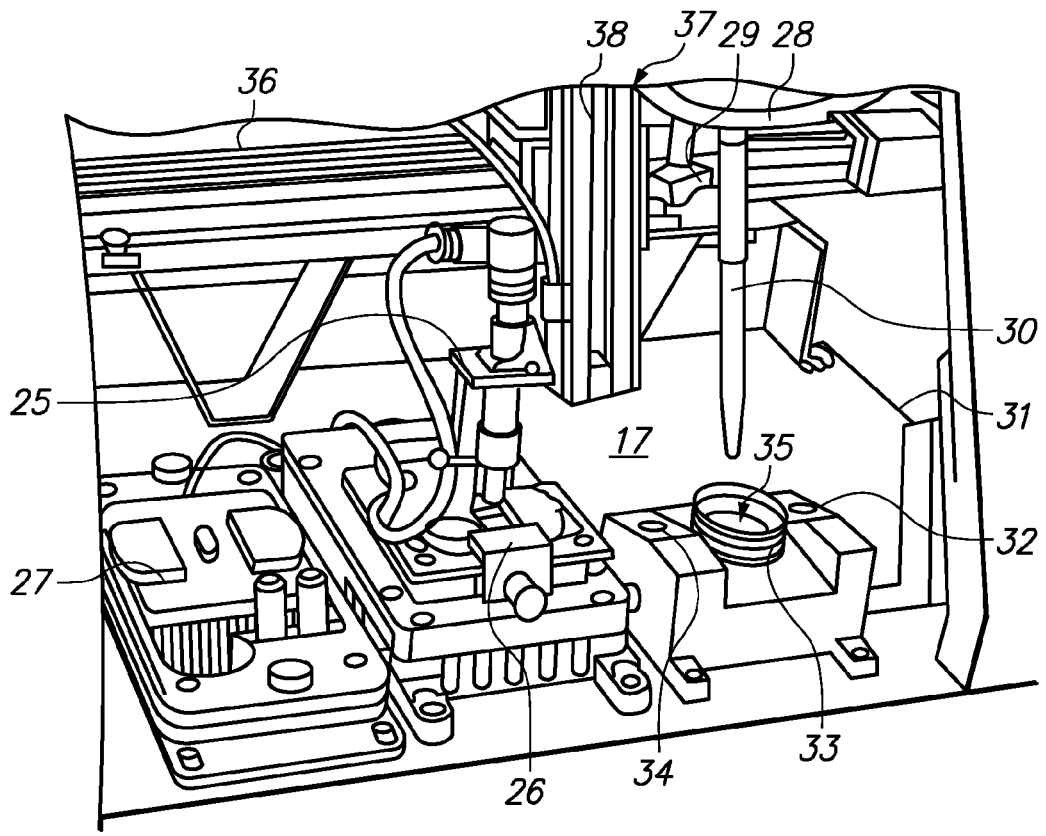
FIG. 4 is a partial perspective view of process compartment of the processing station.

Referring to FIG. 4, the process compartment 17 generally includes a cell block cassette interface 26 configured for removably seating the cell block cassette and (attached) filter assembly 14. A fluid level sensor 25 is mounted in a fixed position relative to the cassette interface 26 to detect a fluid level in the collection well of the cell block cassette 14 (described in greater detail herein). In particular, where an ultrasound sensor is used, the sensor 25 is mounted directly above and orthogonal to the fluid surface in the collection well. The sensor 25 is preferably mounted on a pivoting attachment that can be moved to allow for inserting and removing a cell block cassette from the cell block cassette interface 26. A heated paraffin reservoir 27 (e.g., containing Paraplast-Xtra® paraffin wax) is disposed to one side, and a sample vial interface (or holder) 33 is disposed to another side, respectively, of the cell block cassette interface 26. The sample vial interface 33 defines a well 35 for removably seating a standard fluid sample vial (not shown) from which cellular matter is to be aspirated for creating a respective cell block. The sample vial interface 33 is flanked on its sides by a sample pipette tip holder 32 and a liquid waste port 34, respectively.

An automated arm assembly 37 is mounted along a rear portion of the process compartment 17, and includes a delivery arm 28 that may moved horizontally along rail 36 and vertically along rail 38. The delivery arm 28 is coupled to a pipette holder adapted to selectively retrieve, carry and discard (using the pipette tip remover 31) pipette tips 30 used for fluid and paraffin aspiration and dispensing during cell block processing. A pipette tip sensor 29 is fixed to the delivery arm 28 for detecting whether a pipette tip is connected to the tip holder. The delivery arm 28 and pipette holder are preferably configured so that pipette tips attached to the holder will approach the sample collection well of a mounted cell block cassette at an angle from the perpendicular (e.g., 15-20°) in order to avoid interfering with the fluid level sensor 25 when dispensing sample fluid, stain, reagents and/or paraffin into the cassette collection well.

Figure 5:
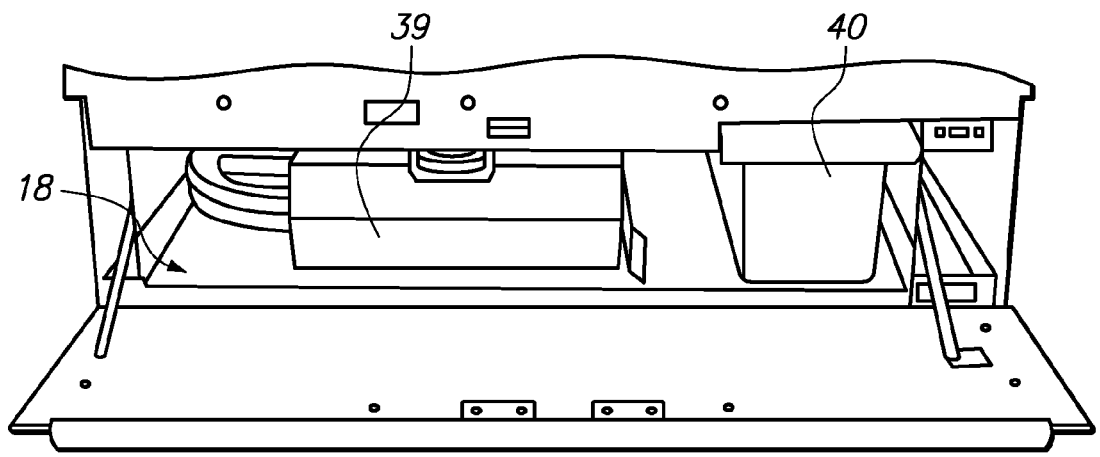
FIG. 5 is a partial perspective view of a waste compartment of the processing station.

Referring to FIG. 5, the waste compartment 18 generally includes a fluid waste chamber 39 underlying the cell block cassette interface (FIG. 4), and a pipette tip waste bin 40 underlying the pipette tip remover 31 (FIG. 4). As will be explained in greater detail herein, the waste chamber 39 is sized for single cell block processes and maintains a closed system in conjunction with a cell block cassette seated in the cassette interface. As explained in greater detail herein, the contents of the waste chamber 39 are evacuated into a large waste container (not shown) prior to (or following) each new cell block process.

Figure 10A:
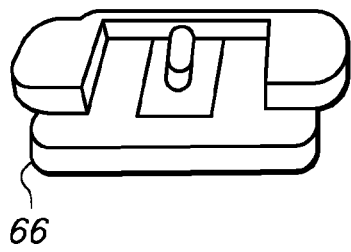
FIGS. 10A-10C show perspective views of the heated paraffin bath assembly components in the cell processing station.
Figure 10B:
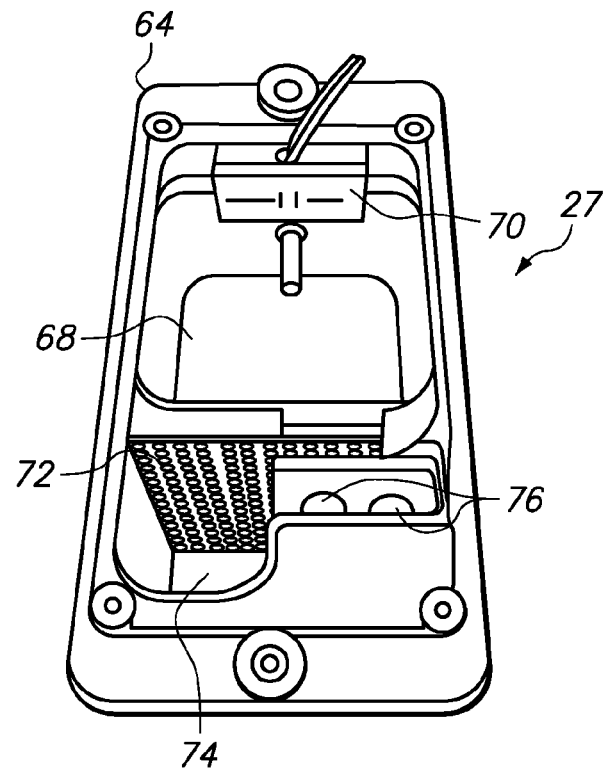
Figure 10C:
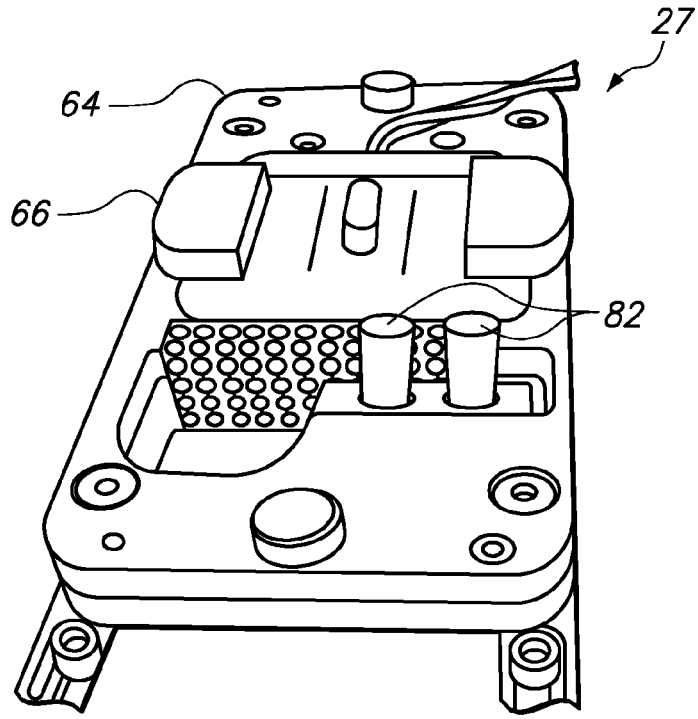

FIGS. 10A-10C show perspective views of the components of the heated paraffin bath 27, which includes a main body 64 defining a heated wax tank 68 that is covered using a removable cover plate 66 (FIG. 10A; shown assembled on FIG. 10C). The cover plate 66 reduces the likelihood that the wax may become contaminated by airborne pollutants. Prior to processing a cell block, pieces of wax paraffin are placed in the heated wax tank 68 and melted. A temperature sensor 70 is provided for the controller to monitor and regulate the temperature of the wax bath 68. The wax bath is divided by a screen 72, with a portion 74 of the bath 68 left exposed by the cover plate 66, allowing for a pipette tip carried by the pipette holder on the automatic arm assembly to be positioned in the bath portion 74 for aspiration of liquefied paraffin there from. New pieces of wax are preferably inserted in the portion of the bath 68 that is underlying the cover plate 66, and the screen 72 keeps any solid pieces that have not yet melted from clogging up a pipette tip submerged in the exposed portion of the bath 74. As described herein, the paraffin aspiration and dispensing process will typically require two separate pipette tips. For this purpose, a pair of pipette tip holding slots 76 (FIG. 10B) are built into the paraffin bath structure 27 for holding a respective pair of pipette tips 82 (FIG. 10C).

Figure 6A:
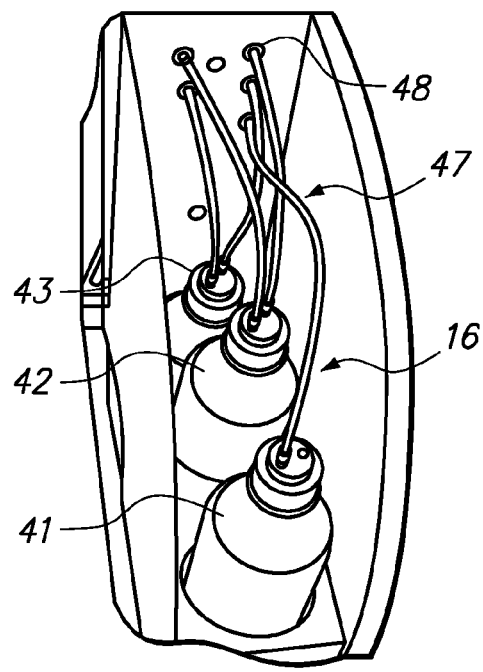
FIG. 6A is a partial perspective view of a reagent compartment of the processing station.
Figure 6C:
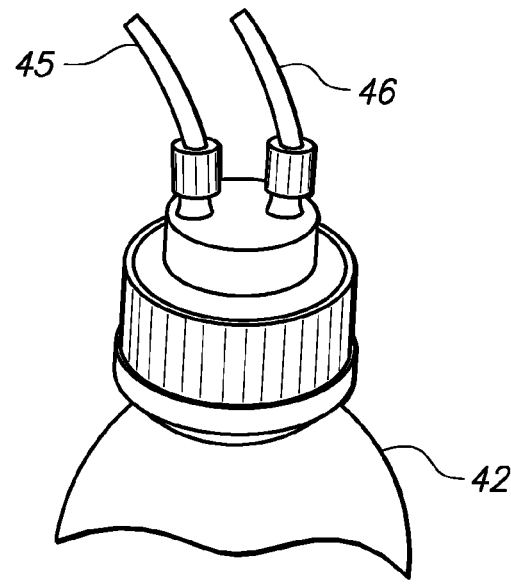
FIG. 6C is partial perspective view of a reagent container top and lid, illustrating the outflow and inflow tubing connections.
Figure 6B:
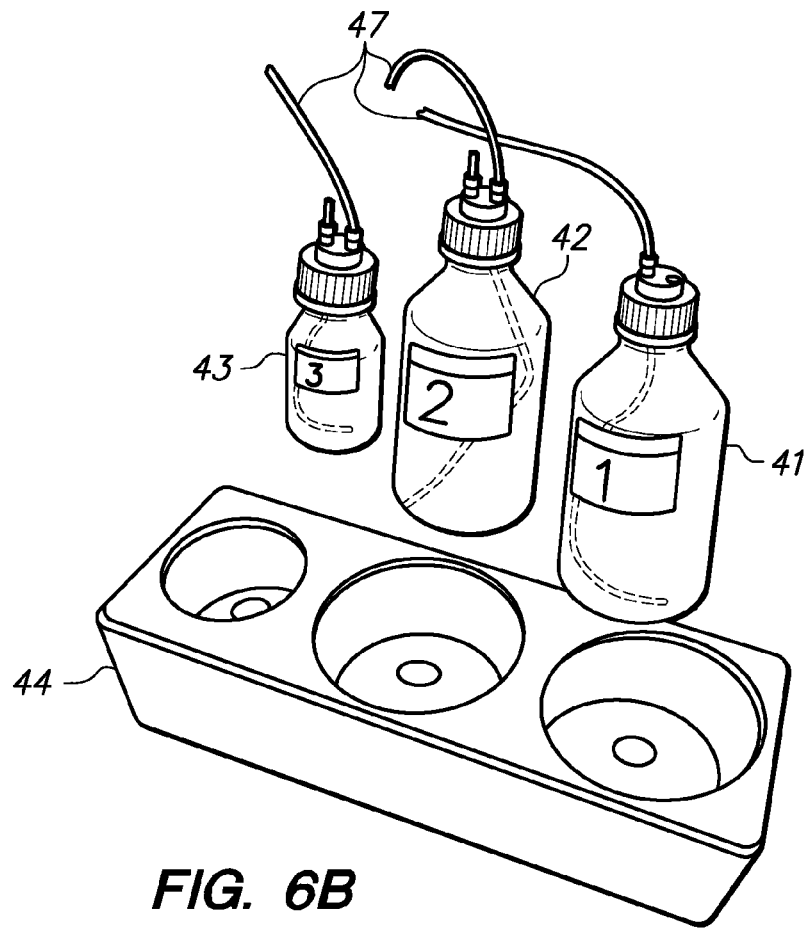
FIG. 6B is a perspective view of a reagent holder tray that is housed in the reagent compartment.

Referring to FIG. 6A, the reagent compartment 16 stores three separate fluid containers. The first container 41 stores alcohol for use as a drying agent (e.g., 98% isopropyl alcohol, HPLC-UV grade). The second container 42 stores xylene for use as a clearing agent to remove the alcohol (e.g., reagent grade ACS, histology lab grade 100% xylene). The third container 43 stores a staining agent (e.g., eosin Y intensified stain available from Fisher Scientific), which is used (optionally) to stain the cellular matter prior to application of the alcohol and xylne. While technically not itself a "reagent", the stain container 43 is kept in the reagent compartment 16. As shown in FIG. 6B, the fluid containers 41, 42 and 43 are seated in respective wells formed in a holding tray 44 for added stability. To reduce the chances of confusion, the connector feed lines 47 for the fluid containers are preferably different colors from one another, for example, the eosin stain has a red feed line, xylene a green feed line, and the isopropyl alcohol a blue feed line.

As shown in FIG. 6A, possible confusion or entanglement of the fluid feed lines 47 is further reduced by providing a manifold 48 to keep the lines spaced apart within the reagent compartment 16. The fluid containers 41, 42, 43 are provided with respective air inlets (or air inlet lines if they are pressurized) to replace the fluid contents as they are dispensed. By way of example, FIG. 6C shows a container lid for the xylene container 42, which includes a green outlet (feed) line 45, and a white air inlet line 46. The respective fluid feed lines 47 are each coupled to the pipette tip holder, with a respective valve operable by the controller to place the respective individual fluid feed lines feed line in fluid communication with a pipette tip carried by the pipette holder. In the illustrated embodiment, the eosin stain and xylene feed lines are pressurized using standard in-line pumps (not shown), and the isopropyl alcohol feed line is coupled with an in-line syringe pump (not shown), which allows the alcohol feed line to alternatively be used as an sample fluid and paraffin aspiration suction source by the pipette holder.

Figure 7:
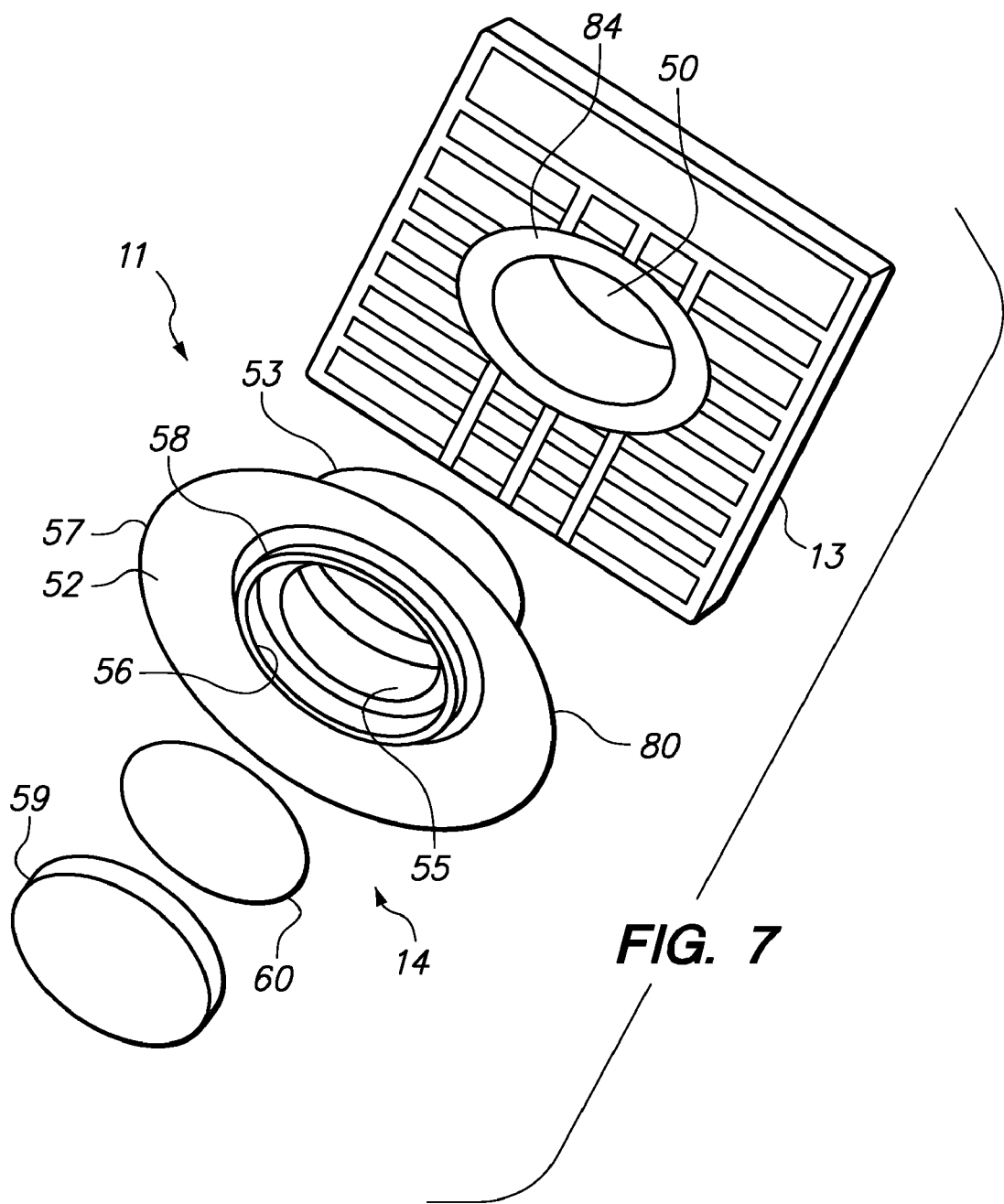
FIG. 7 is an exploded perspective view of the cell block cassette and filter assembly.

Referring again to FIG. 1, as well as to FIG. 7, the cell block cassette 11 includes a main cassette body 13 made of molded plastic and having a collection aperture 50 formed therein, and a filter assembly 14 removably attached to the main cassette body 13 and defining a sample collection well 54 in communication with the collection aperture 50 when the pieces are attached. A filter 60 (e.g., a "track edge" filter membrane) is positioned across a bottom surface of the collection well 54, and is sized configured to retain cellular matter (e.g., cervical cells) carried in a sample fluid (e.g., preservative solution) that is dispensed into the collection well 54 and flows across the filter 50. It has been found by the inventors that a filter having a relatively high density (number per area) of pores having diameters less than about 5 microns and, in particular, approximately 3 microns each are suitable for cell block processing using embodiments of the invention, since much of the cellular matter and other objects in the sample solution is between 7-9 microns in diameter, and larger pores tend to become clogged prior to when an adequate cell layer has been deposited on the filter.

Still referring to FIGS. 1 and 7, the filter assembly 14 comprises a single-piece housing or body 80 having a base portion 52 forming the sealing surface, and a neck portion 53 extending from the base portion 52. The neck portion 53 defines a perimeter 55 of the collection well 54, and has a top end that makes an interference fit with an annular grove 84 located in a bottom surface of the main cassette body 13 in order to detachably attach the filter assembly 14 to the main cassette body 13. The filter assembly housing further comprises a filter support retention portion 56 extending from an underside of the base portion 52, with a thermally conductive porous filter support member, e.g., a sintered metal disc or other thermally conductive porous support 59 (such as a metal screen or solid thermally conductive disc with holes punched in it) retained therein, the filter 60 being positioned atop the filter support member 59 within the collection well 54. The support 59 also serves to transmit heat and cooling to the contents of the collection well via electronics (e.g., a peltier system) located in or accessed through the waste chamber (not shown). The base portion sealing surface slopes at a downward angle from the neck portion, such that an outermost edge 57 of the sealing surface extends to (or beyond) an outermost edge 58 of the filter support retention portion 56 in order to form a seal with the waste chamber interface (described below) on the processing station 10.

In particular, cells must be contained on the filter 60 and the sample fluid, stain, reagents and paraffin must be allowed to pass through the system and be discarded in the waste chamber, leaving only cells and hardened paraffin wax behind. As mentioned above, a vacuum in fluid communication with the waste chamber interior is applied by the controller across the filter 60 at varying strengths (described herein) in order to achieve this fluid pass. Pressured air may also applied under certain conditions from the underside of the collection well to ensure the pores of the filter membrane are not blocked. The filter membrane 60 must be able to withstand all of these conditions; and the housing 80 provides a container for this purpose. The filter may be heat staked across a bottom area of the (polyester) housing 80 to define turn the collection well 54. The filter support member 59 (in one embodiment, a sintered bronze or other metal disc) provides a porous, thermally conductive support to be pressed against the filter membrane 60 to support both during vacuum and pressured air cycles.

Figure 8:
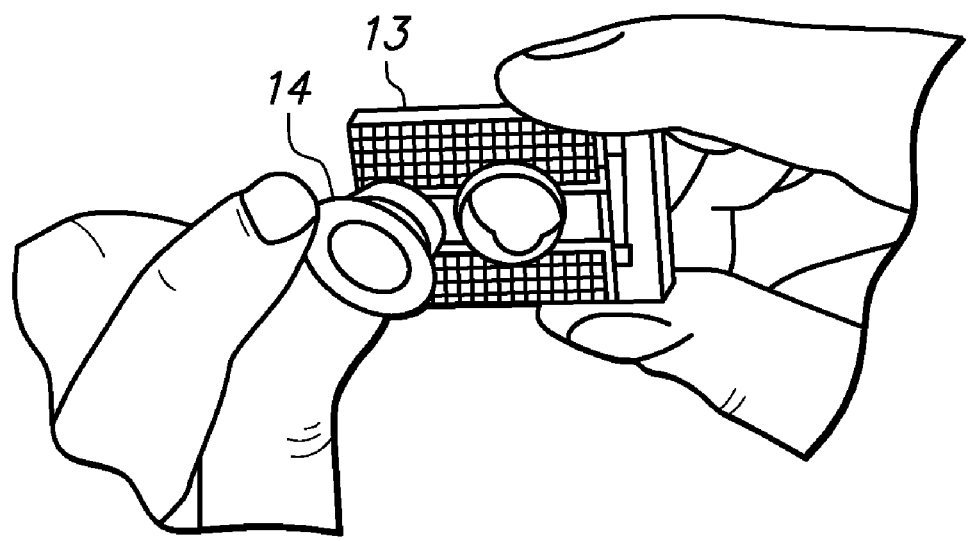
FIG. 8 depicts a user attaching the filter assembly to the cell block cassette prior to creation of a new cell block.
Figure 9:
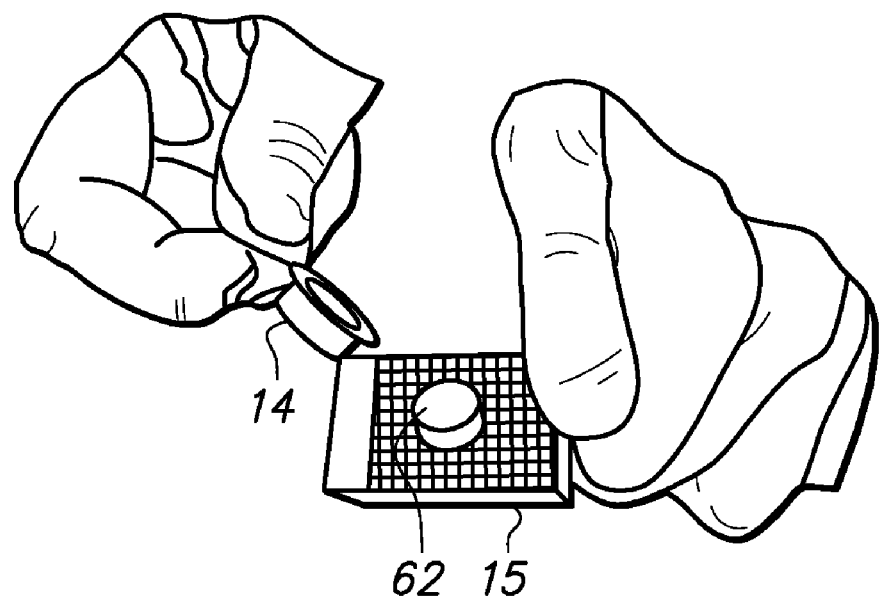
FIG. 9 depicts a user detaching the filter assembly from the cell block cassette following creation of a new cell block.

The housing (or filter holder) 80 and attached (heat staked) filter 60 define the collection well 54 for the various liquids and wax to form a hardened protrusion from the mating cassette body 13. This filter allows the fluids to pass through but leave cells to collect on the surface of the membrane. The vacuum is involved in the process to pull fluid through the filter, so a metal or other hard support member 59 is used to keep the filter 60 from being pulled into the waste chamber by the vacuum. This support member 59 has a given porosity, such as 80 microns, to allow fluid to easily continue to pass through the filter assembly after passing through the much smaller filter pores. The sealing surface of the base portion 52 forms a vacuum seal on the outer sealing edge of the waster chamber interface when the cassette is seated (and latched into) the cassette interface in the processing station. The compliant nature of the outer plastic "mushroom" shape of the sealing surface 52 provides both adequate vacuum sealing and a proper preload when compressed to withstand the pressure applied to the under surface during back pulsing (pressurized air pulsing). The sealing surface of the base 52 also provides the system operator with a graspable means to remove the filter assembly 14 from the main cassette body 13, thus leaving behind a solid protrusion of paraffin wax containing a layer of cells at the very top end of the wax protrusion when the cell block has been processed. For purposes of illustration, FIG. 8 depicts an operator attaching the filter assembly 14 to the main cassette body 13 prior to processing a new cell block. FIG. 9 depicts the operator detaching the filter assembly 14 from the cell block cassette 13 following creation of a new cell block 62.

Preferably, the main cassette body has a substantially planar top surface and a substantially planer bottom surface, and the top and bottom surfaces are substantially parallel with one another, to allow for ease in stacking of multiple cassette bodies having their respective filter assemblies removed (e.g., for labeling, bar code application, etc).

In alternative embodiments, many other structures and methods of obtaining the same outcome of creating a collection well are possible. For example, a radial seal can be used to create the vacuum seal, something similar to the seals used in syringes. This would require the use of a more compliant material, and possibly with a form of rubber insert as a seal. A face seal also could be used for forming the vacuum seal, which would include the use of some sort of gasket or similar material either free to float on the instrument or fixed to the interface. The gasket material could also be placed on the base of the filter holder depending on the design. Other shapes and geometries can be used for the filter housing 80, which would create various shapes and sizes of the collection well. One such alternative shape is oval, which would reduce the need for a re-melt step (discussed in conjunction with the finishing station 20), since the microtome would be able to make a ribbon out of the block as is.

Figure 11A:
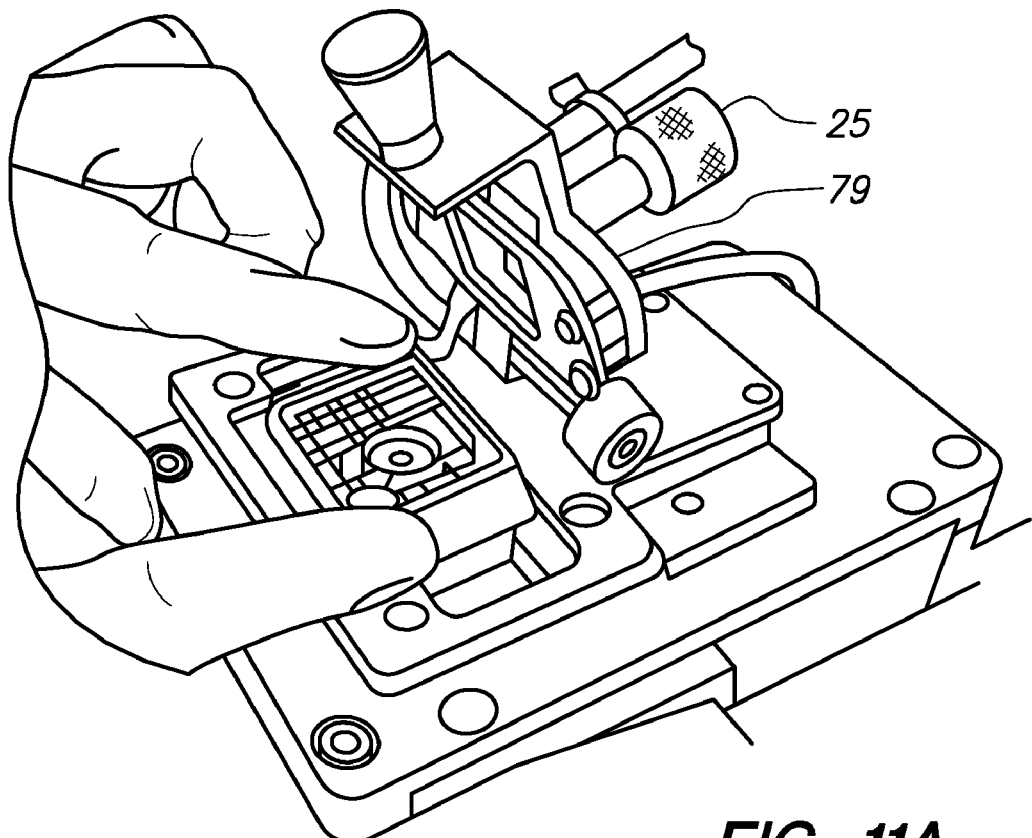
FIGS. 11A-B depict a user loading a cell block cassette and attached filter assembly into the cell block interface prior to creation of a new cell block.
Figure 11B:
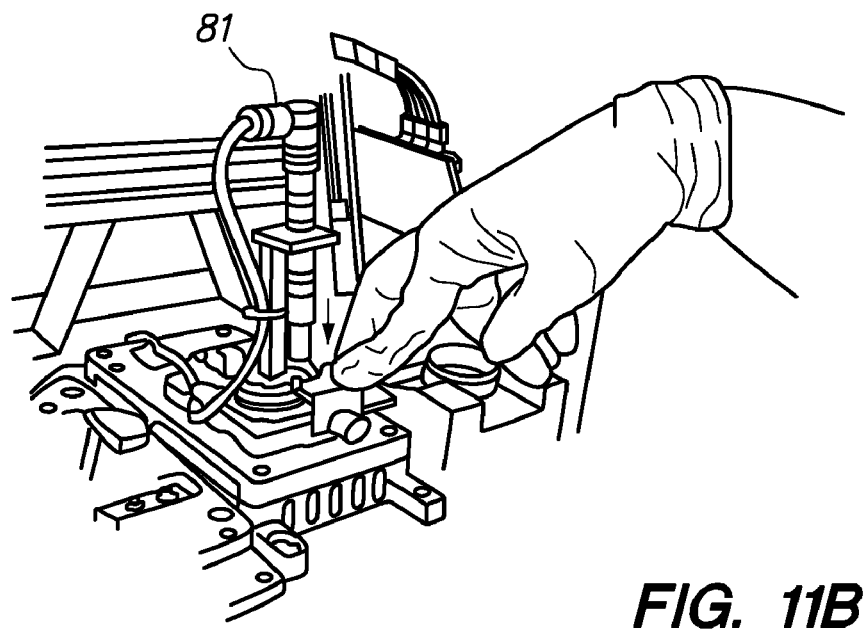

For purposes of illustration, FIGS. 11A and 11B depict a user loading a cell block cassette and attached filter assembly 11 into the cell block interface on the processing station prior to creation of a new cell block. Notably, a clamping member 79 of the sensor assembly 81 may be pivoted and moved aside (FIG. 11A) for inserting the cassette 11 into the interface, after which the clamping member is secured to the interface (FIG. 11B) so that the sensor assembly 81 (and sensor 25) are properly aligned with the collection well of the (now secured) cell block cassette. Clamping down on the cassette and filter assembly 11 also secures the vacuum seal formed between the sealing surface 52 of the filter assembly and the waste chamber interface (not shown). This is needed in particular to avoid displacement of the cassette/filter assembly 11, or failure of the seal due to backpressure maintained in the vacuum chamber 39 to prevent fluids from passing through the filter 60 unless the vacuum is ON, as well as the more significant back pressure that may be used for temporarily lifting the collected matter off the filter (discussed in detail below). At the time the cell block cassette is loaded into the cassette interface, the user should also verify that the fluid level sensor is clean and unobstructed.

Figure 41:
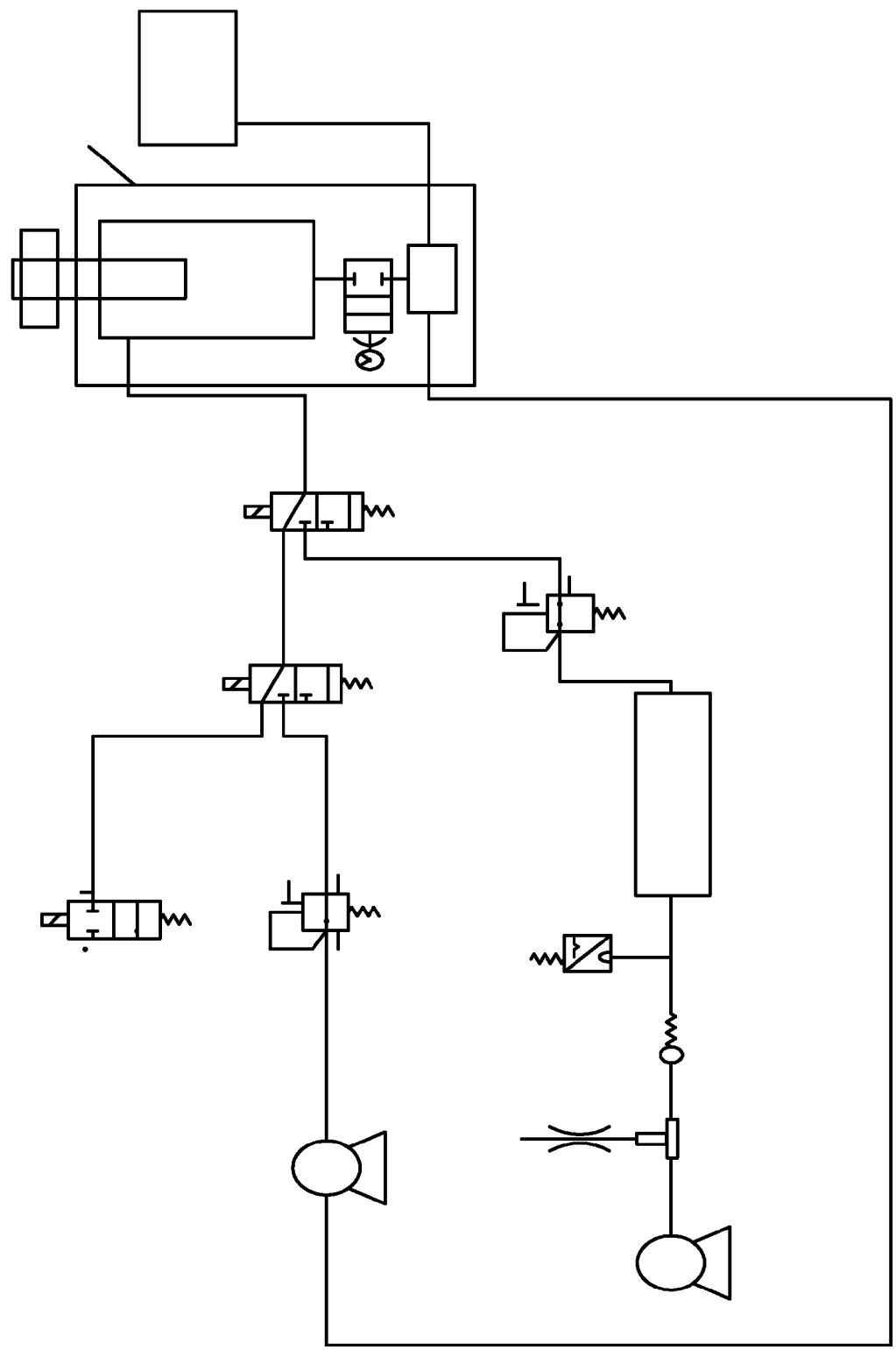
FIG. 41 is an exemplary schematic block diagram of a vacuum and pressure delivery system employed in the waste line of the cell block processing station.

When dispensing the sample fluid into the collection well, certain samples will tend to clog the filter before a sufficient cellular material layer is retained. Such samples usually contain small individual cells, such as lymphocytes and other inflammatory cells, which have a tendency to stack and almost immediately impede the fluid flow across the filter. In order to collect additional cellular materials, and therefore a larger cell layer retained by the filter, air bubbles are pushed (or pulsed) through the filter from the waste chamber to temporarily lift the cellular materials away from the filter surface, and allow more liquid to pass through. This is done by applying a pressure within the waste chamber just larger than the bubble point of the filter material to gently lift the cellular material from the filter surface. FIG. 41 shows embodiment for the vacuum and pressure delivery system for the waste chamber. The pressure pulse valve allows a small pressure to be injected in the waste chamber. This small pressure is just larger than the bubble point of the membrane filter. When sample collection has stalled, this small pressure pulse can lift the sample from the filter and allow more sample to be collected.

In alternate embodiments, another form of sample fluid agitation that may enhance the amount of sample collected is simply mechanical vibration of the cell block cassette and filter assembly 14. Such mechanical motion would likely prolong the amount of time it takes to completely clog the filter pores, thereby allowing more sample to be collected. One or both of lateral vibration (parallel to the filter membrane) and vertical motion may be used. The frequency of vertical vibration would appear to be more sensitive to the amount of sample (mass) present in the collection well. Actuation of the mechanical vibration of the cell block cassette can be accomplished in a verity of ways. For example, a custom piezoelectric actuator designed into the engine assembly could be used to deliver the proper energy required to maximize cellular matter collection. A voice coil design may also be able to deliver enough low frequency energy to enhance sample fluid delivery. Another option would be to deliver energy into the cell block cassette through an acoustic pressure wave induced into the waste chamber interior below the filter membrane. The acoustic energy would vibrate the filter membrane during sample collection, thus, keeping the pores open longer.

As is described further in conjunction with the cell block process flow charts of FIGS. 15-20, when dispensing the sample fluid into the collection well, certain samples will tend to clog the filter before a sufficient cellular material layer is retained. Such samples usually contain small individual cells, such as lymphocytes and other inflammatory cells, which have a tendency to stack and almost immediately impede the fluid flow across the filter. In order to collect additional cellular materials, and therefore a larger cell layer retained by the filter, air bubbles are pushed (or pulsed) through the filter from the waste line to temporarily lift the cellular materials away from the filter surface, and allow more liquid to pass through. This is done by applying a pressure within the waste line just larger than the bubble point of the filter material to gently lift the cellular material from the filter surface.

FIG. 41 shows embodiment for the vacuum and pressure delivery system for the waste chamber. The pressure pulse valve allows a small pressure to be injected in the waste chamber. This small pressure is just larger than the bubble point of the membrane filter. When sample collection has stalled, this small pressure pulse can lift the sample from the filter and allow more sample to be collected.

An alternative form of sample agitation that appears to enhance the amount of sample collected is simply mechanical vibration of the cassette/filter. The mechanical motion prolongs the amount of time it takes to completely clog the filter pores allowing more sample to be collected. Lateral vibration parallel to the filter membrane appears to work better than vertical or perpendicular motion. The frequency of vertical vibration also appears to be more sensitive to the amount of sample (mass) present. Actuation of the cassette/filter can be accomplished in a verity of ways. A custom piezoelectric actuator designed into the engine assembly could deliver the proper energy required to maximize sample collection. A simpler voice coil design may also be able to deliver enough low frequency energy to enhance sample delivery. Another option would be to deliver energy into the cassette/filter through an acoustic pressure wave induced into the waste chamber volume below the filter membrane. The acoustic energy would vibrate the filter membrane during sample collection keeping the pores open longer.

FIGS. 15-20 are detailed flowcharts illustrating the processes undertaken by the processing station 10 when processing a cell block. Notably, the processor of the processing station keeps a log of the cell block events, which may be printed or transferred using the Ethernet or USB connections.

Figure 15:
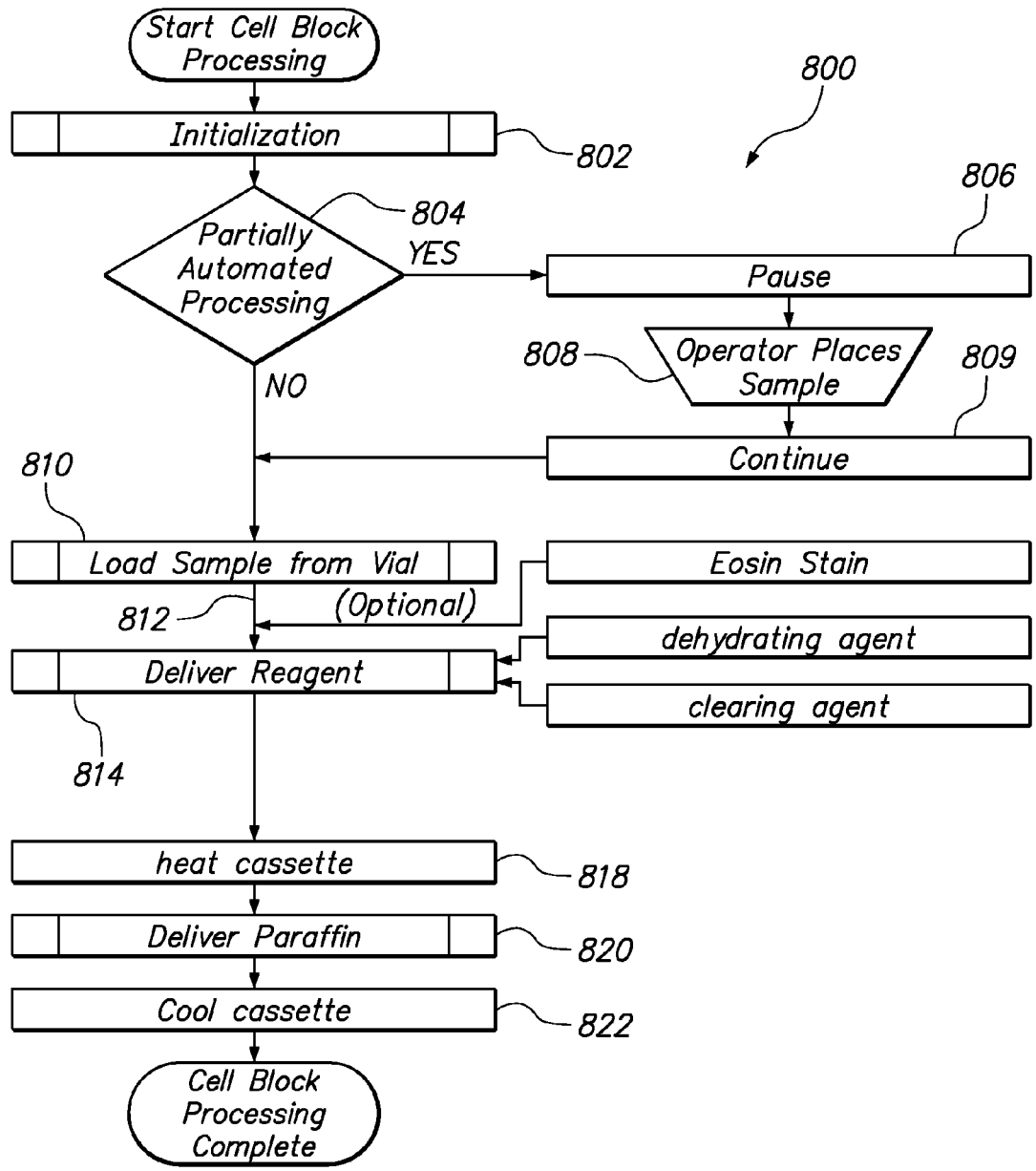
FIG. 15 is a flow chart of the process the cell block processing station undertakes to create a new cell block.
Figure 16:
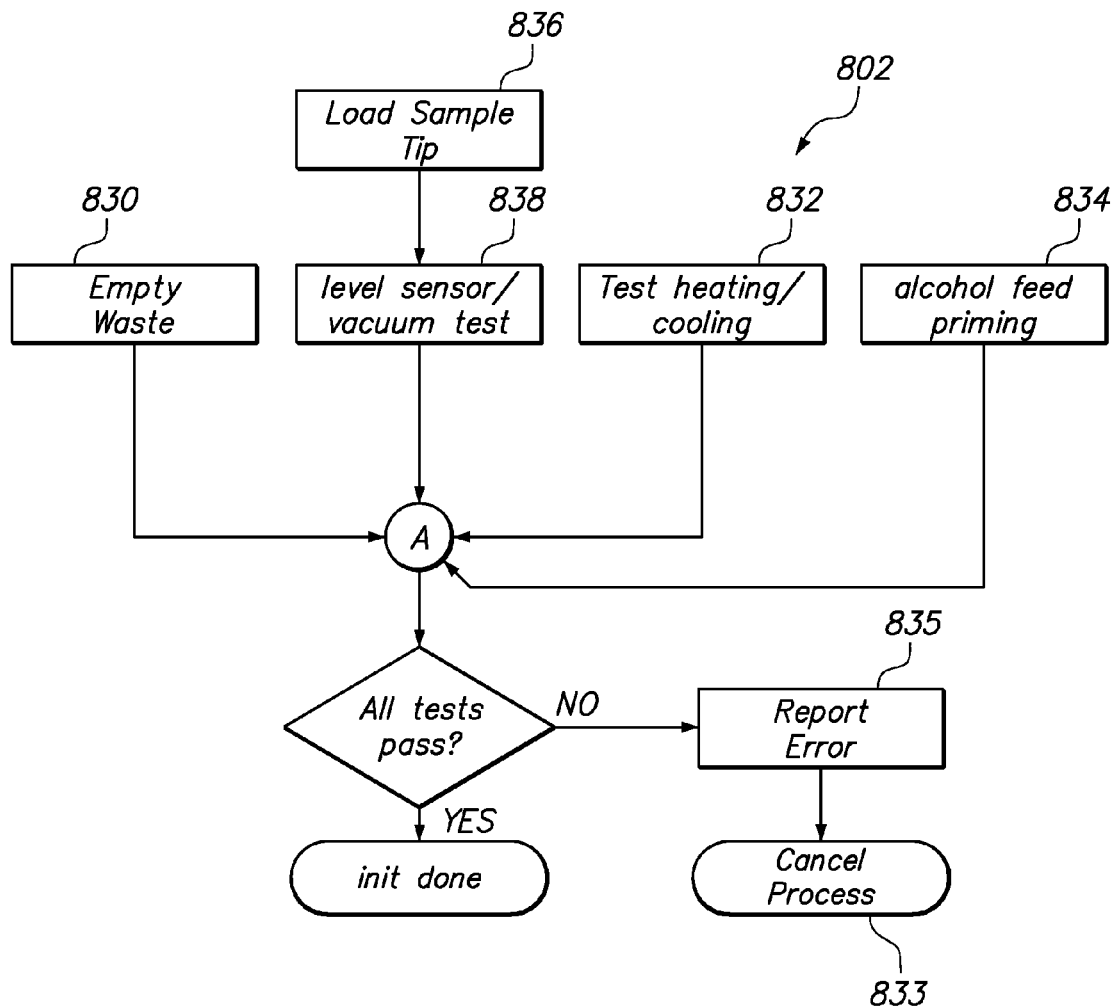
FIG. 16 is a flow chart of the system initialization process for the cell block processing station when undertaking to create a new cell block.
Figure 17A:
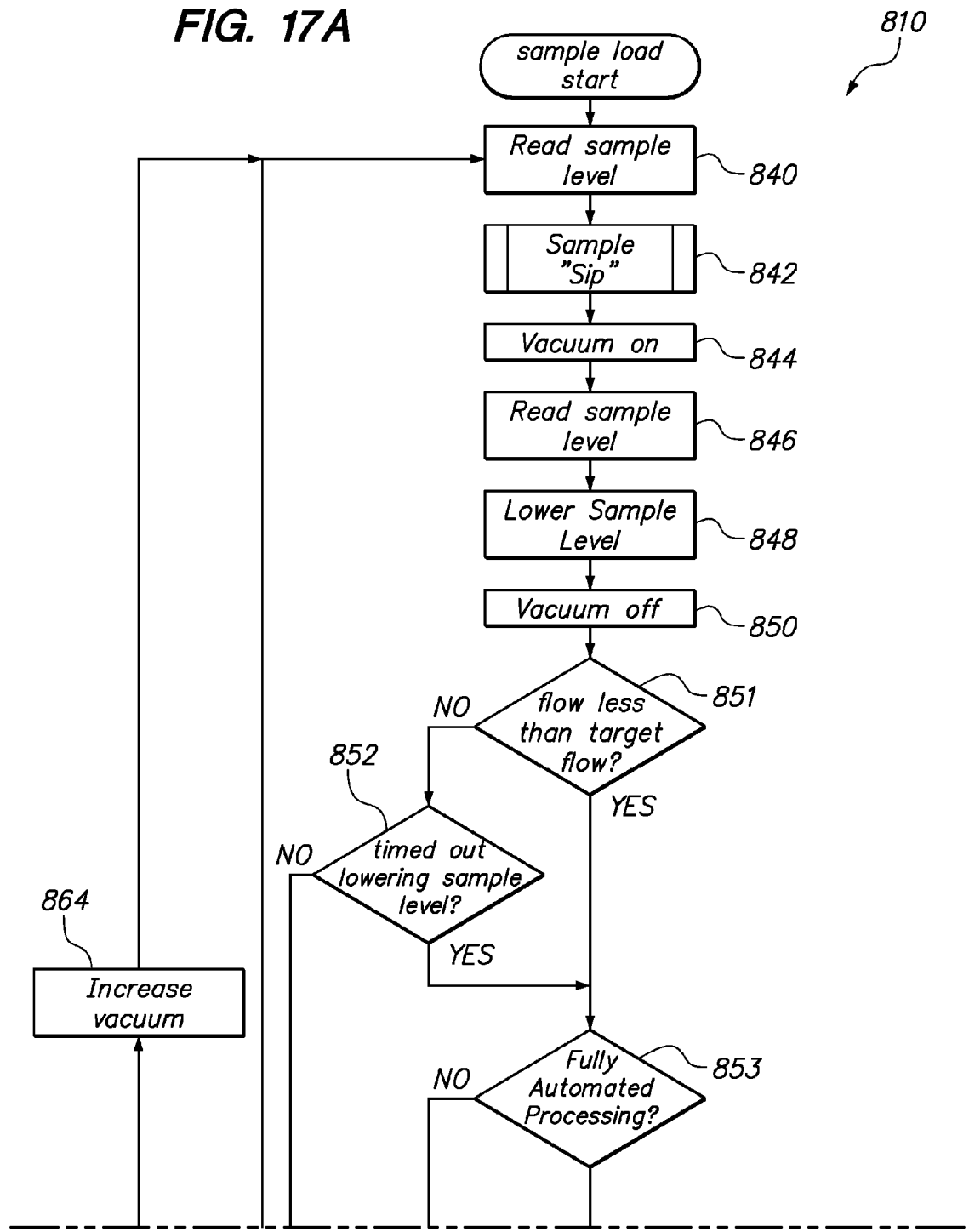
FIGS. 17A-B is a flow chart of the sample fluid delivery process used for creating a new cell block.
Figure 17B:
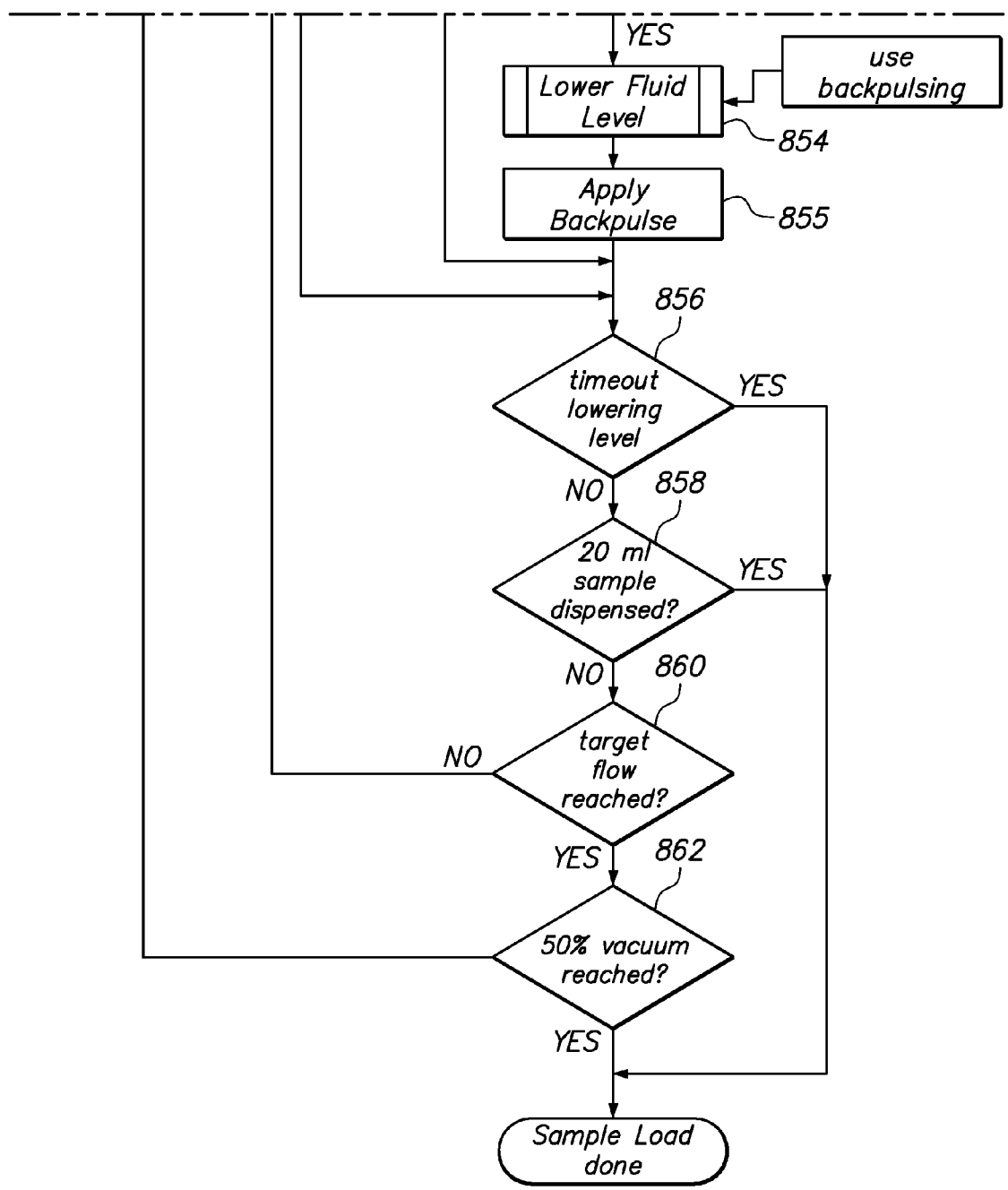

In particular, FIG. 15 is a flow chart of a cell block process 800 using the system 20 of FIGS. 1-14. The user has already loaded a new (and sterile) cell block cassette and filter assembly into the cassette interface of the processing station (FIGS. 11A and 11B), with the sealing surface 52 of the filter assembly forming a vacuum seal with the interior of the waste chamber 39. The user has also verified that there is adequate paraffin in the heated wax bath 68 (FIGS. 10A-C), and sterile pipette tips available at the respective sample interface and wax bath. The amount of sample fluid that is used for processing a cell block is normally limited to 20 ml, but may less may be used if a sufficient cell layer is collected by the filter with less sample fluid. Thus, a user should verify that the sample vial has at least 20 ml of fluid prior to commencing the cell block process 800.

The cell bock process 800 starts with an system initialization cycle 802 of the processing station, which (referring also to FIG. 16) includes evacuating the waste chamber (830) any liquid or solid waste remaining from the last cell block process (discussed below) by opening a heated waste chamber evacuation valve; testing the heating/cooling system (832) for the sample collection well (i.e., the peltier system that controllably heats and cools, respectively, the filter support 59, which in turn heats or cools the contents of the collection well 54); and priming the isopropyl alcohol feed line (834) using the liquid waste port provided at the sample vial interface to dispose of the alcohol. The system then loads a sample fluid pipette tip (836) and tests the fluid level sensor and waste chamber vacuum systems (838). Assuming no errors are encountered during the initialization process 802, the initialization is completed and the sample fluid aspiration process commences. If one or more errors occur during the initialization, the system reports these to the user (835) and the cell block process is cancelled (833).

Referring back to FIG. 15, the user indicates whether the cell block process will be fully or "partially automated" (804), where "partially automated" indicates that the user will be manually loaded tissue fragments into the collection well in addition to the sample fluid aspiration. If "partially automated" is selected, the system pauses (806) to allow the user to manually insert (e.g., with tweezers or the like) tissue fragments into the collection well. For example, this may be required because there are tissue fragments in a patient sample that may otherwise clog the aspiration pipette tip. In any event, once the tissue fragments are manually placed in the collection well, the system continues the process (809). Notably, there may be differences in the automated processing if the user has manually inserted tissue fragments, e.g., pressurized air back pulsing (or "burping") through the filter is not used, and the amounts and exposure times of the respective reagents (isopropyl alcohol and xylene) and paraffin are much greater than if the cellular materials are limited to those collected through sample fluid aspiration. Also, in order for the system to continue with the automated cell block processing, a fluid aspiration component must still be used (and a sample fluid vial is required), even if the tissue sample is limited to a relatively large fragment taken from a core biopsy.

The system then undertakes the process (810) of aspirating sample fluid from the sample vial and dispensing the sample fluid into the collection well of the cassette-filter assembly using a pipette tip. The amount of fluid that is dispensed at any one time always depends on the existing fluid level in the collection well (measured by the sensor 25) and may also depend on the most recently measure flow rate across the filter. Also, the waste chamber back pressure is maintained so that no fluid flows across the filter unless the vacuum is activated. Because the pipette tips have a fixed volume, and the syringe pump on the isopropyl alcohol feed line may be precisely controlled, the controller can carefully track how much fluid is aspirated, from the sample vial, how much has been dispensed into the collection well, and how much remains in the pipette tip at any given time. Prior to dispensing fluid into the collection well (including the first time), the controller checks on the fluid level in the collection well (840). Depending on the amount of fluid already in the collection well, the controller then activates the syringe pump on the alcohol feed line to dispense a limited volume of sample fluid into the collection well (842). The details of this sample "sipping" process 842 are shown in FIG. 18A.

Figure 18A:
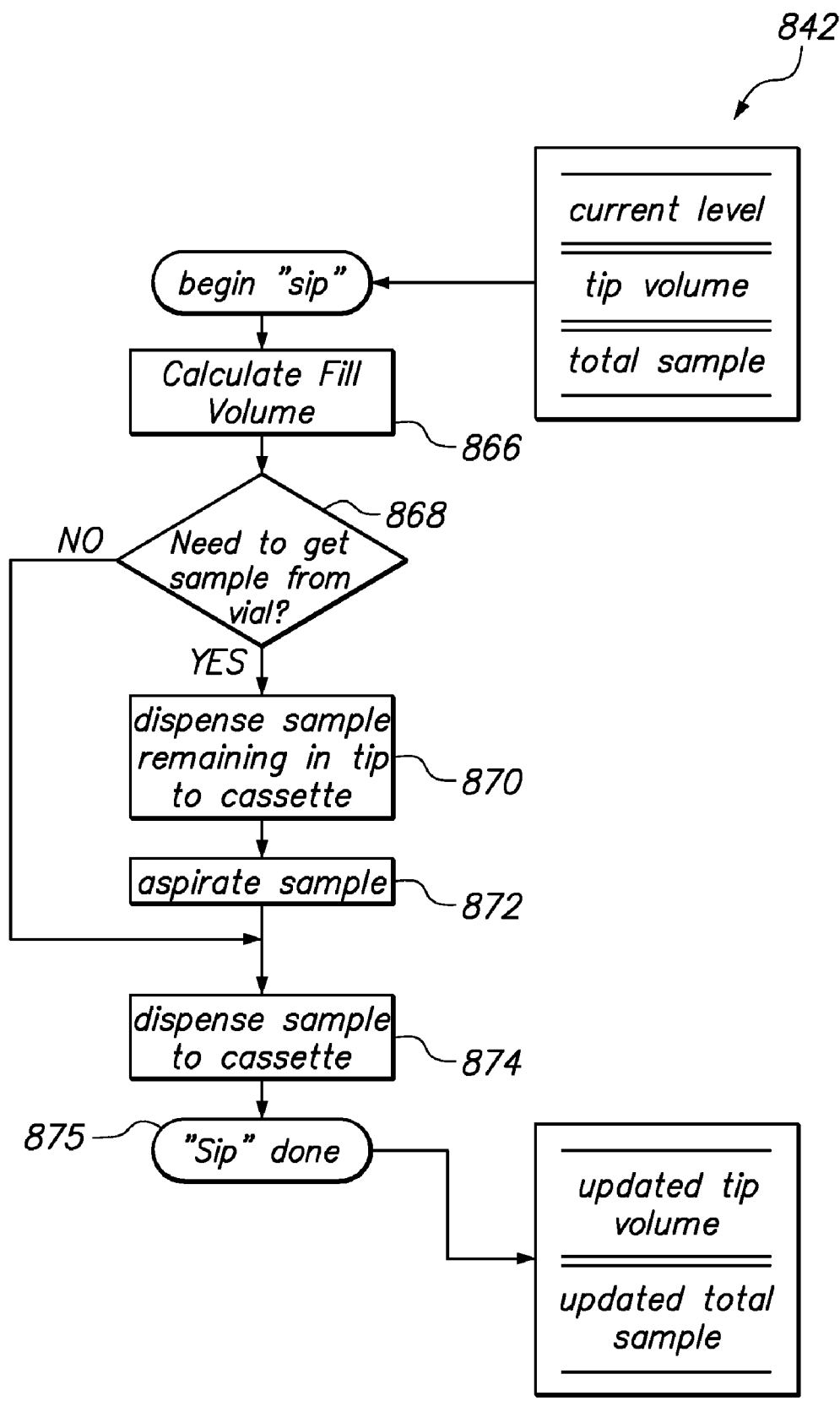
FIG. 18A is a flow chart of the sample sipping process in the fluid delivery process of FIGS. 17A-B.

In particular, with reference to FIG. 18A, the sample sipping process 842 starts with the controller calculating the available fill volume 866 in the collection well based on the fluid level sensor reading. Then, depending on the current volume, if any, of sample fluid remaining in the pipette tip from a previous sipping process, the controller determines whether additional sample fluid needs to be aspirated into the pipette tip (868) in order to meet the calculated fill volume. If additional sample fluid is needed, the controller first dispenses the remaining sample fluid in the pipette tip into the collection well (870), and then aspirates additional sample fluid from the sample vial (872) and dispenses the balance of the fill volume into the collection well (874) to complete the sip process (875).

Figure 18B:
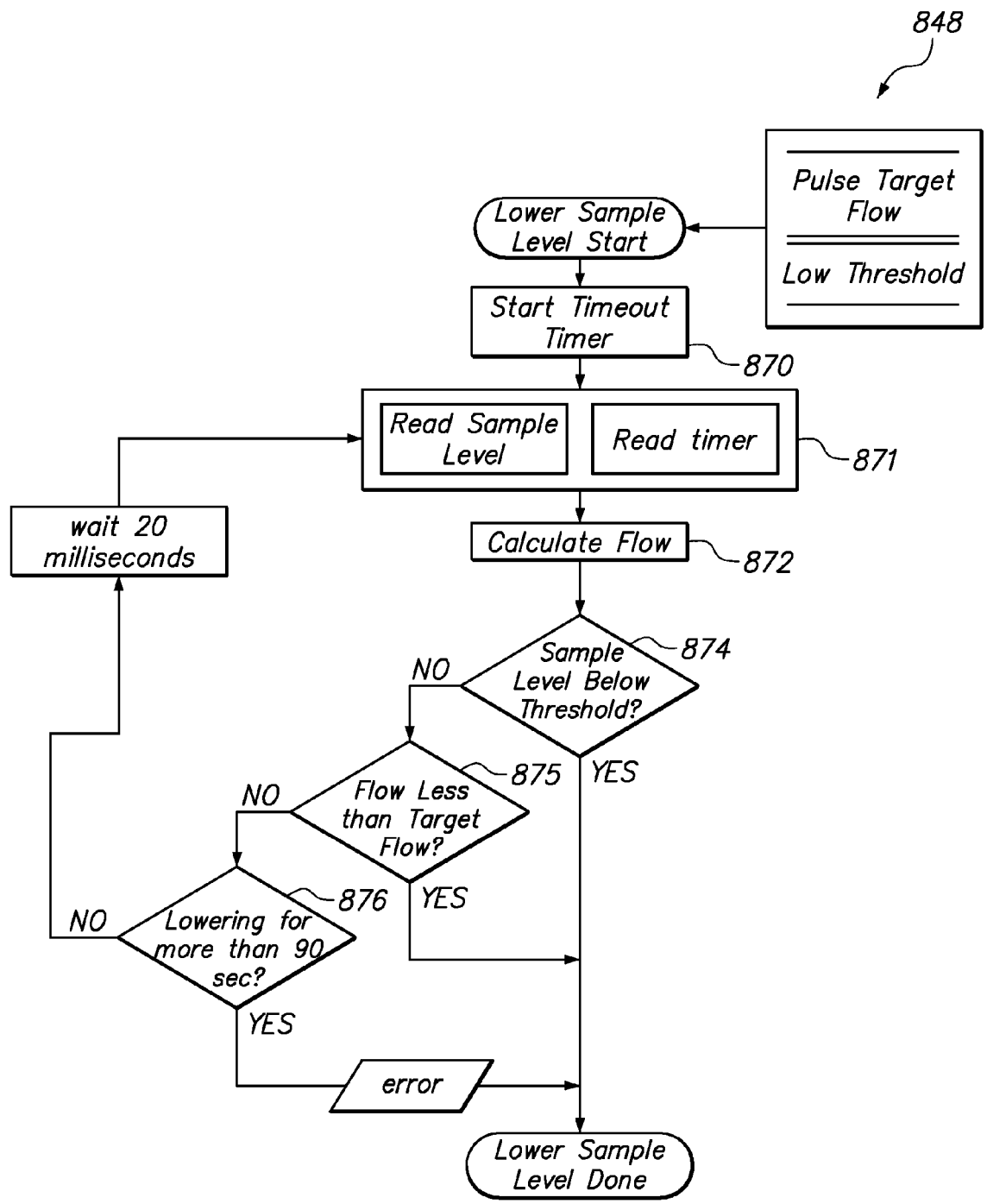
FIG. 18B is a flow chart of the sample fluid level lowering process in the fluid delivery process of FIGS. 17A-B.

After the sample fluid is dispensed into the collection well, the controller activates the vacuum pump (844) in fluid communication with the waste chamber sample to draw the fluid across the filter, while monitoring the fluid level (846) in the collection well as a function of time. The details of the "lower sample level" process (848) are shown in FIG. 18B. In particular, two threshold items are monitored: a pulse target flow rate, which is the flow rate at which a back pressure (or "burping" pulse) may be applied, and a low threshold fluid level, which is the threshold fluid level that is maintained in the collection well at the end of a sample sip process. To initiate the "lower sample level" process (848), a "timeout" timer is started by the controller (870), and the fluid level is monitored with respect to the timer (871). From this information, along with the known dimensions of the collection well, a flow rate across the filter may be calculated (872). So long as the sample fluid drains down to the threshold level (874) without any "timeout", then the process is complete, and the flow rate is noted by the system. If the sample level does not fall below the threshold, but the flow rate is less then the target rate, then the process is complete. However, the sample level does not fall below the threshold and the flow rate is not less then the target rate, then the monitoring of the fluid level and flow rate continues (steps 871-872 repeated). In one embodiment, the fluid level and flow rate are monitored every 20 milliseconds for up to 90 seconds, after which, the system "times out" and an error message is provided to the user (876).

Figure 18C:
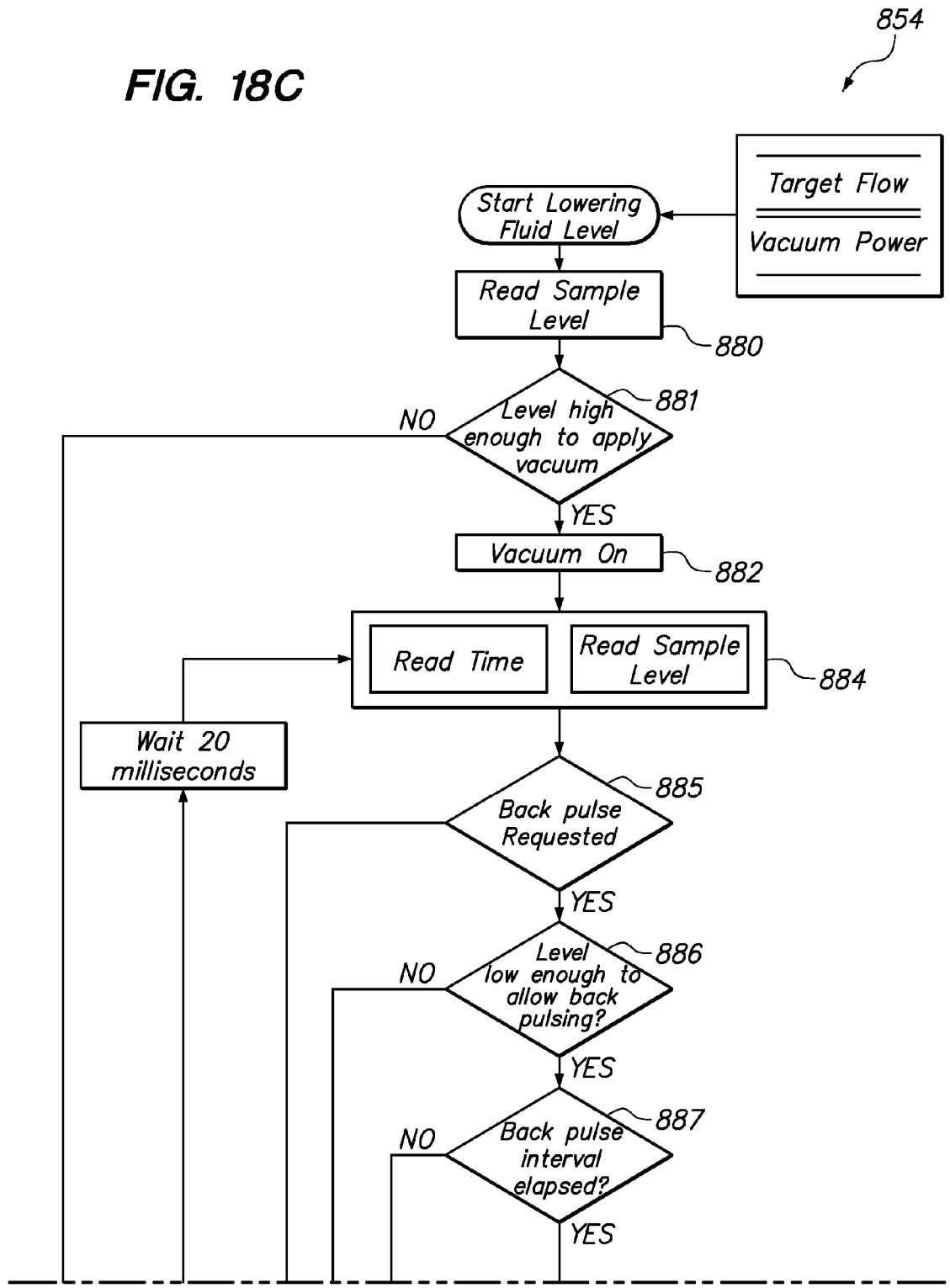
FIGS. 18C-D is a flow chart of the sample fluid level lowering process in the fluid delivery process of FIGS. 17A-B.
Figure 18D:
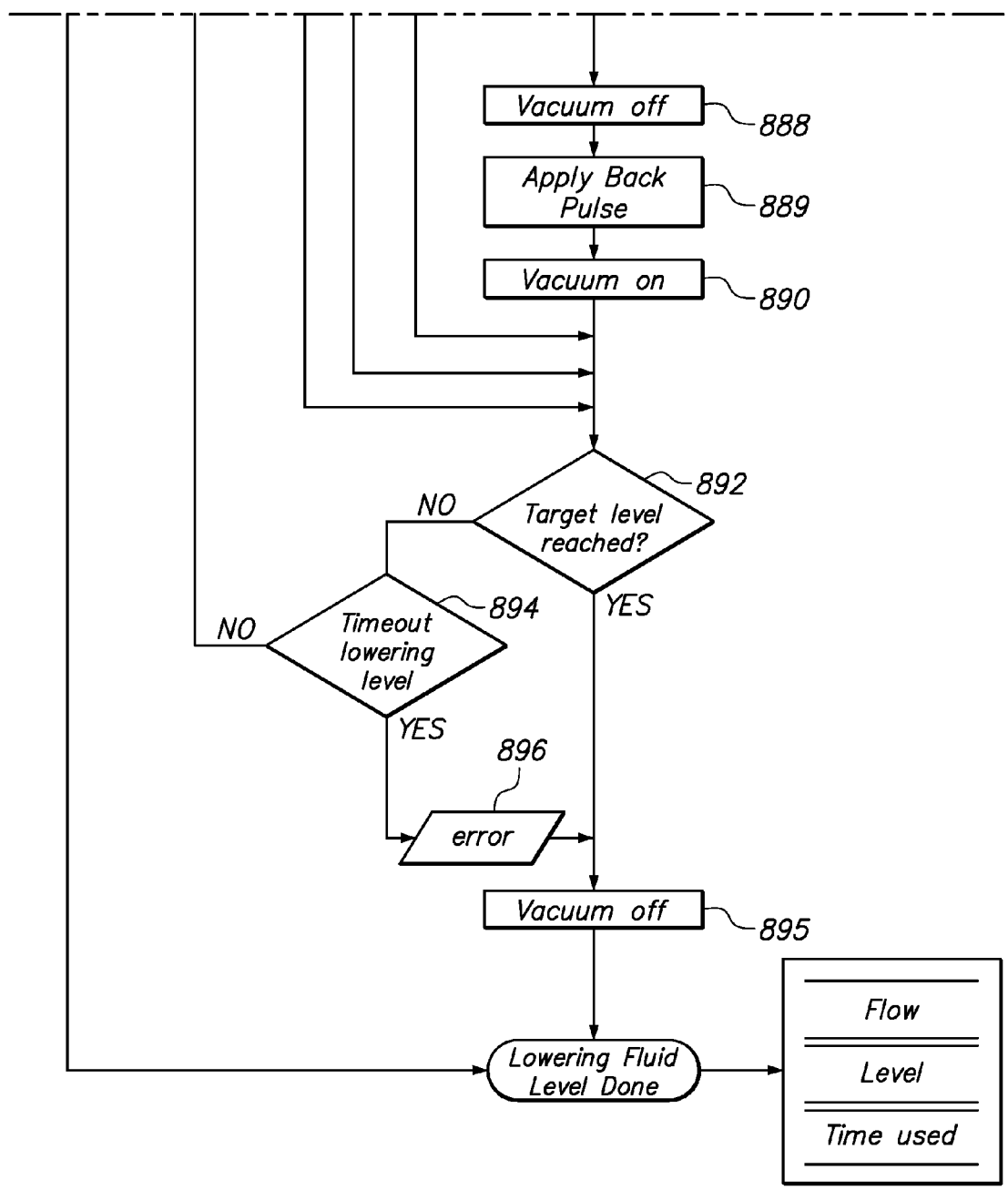
Figure 19:
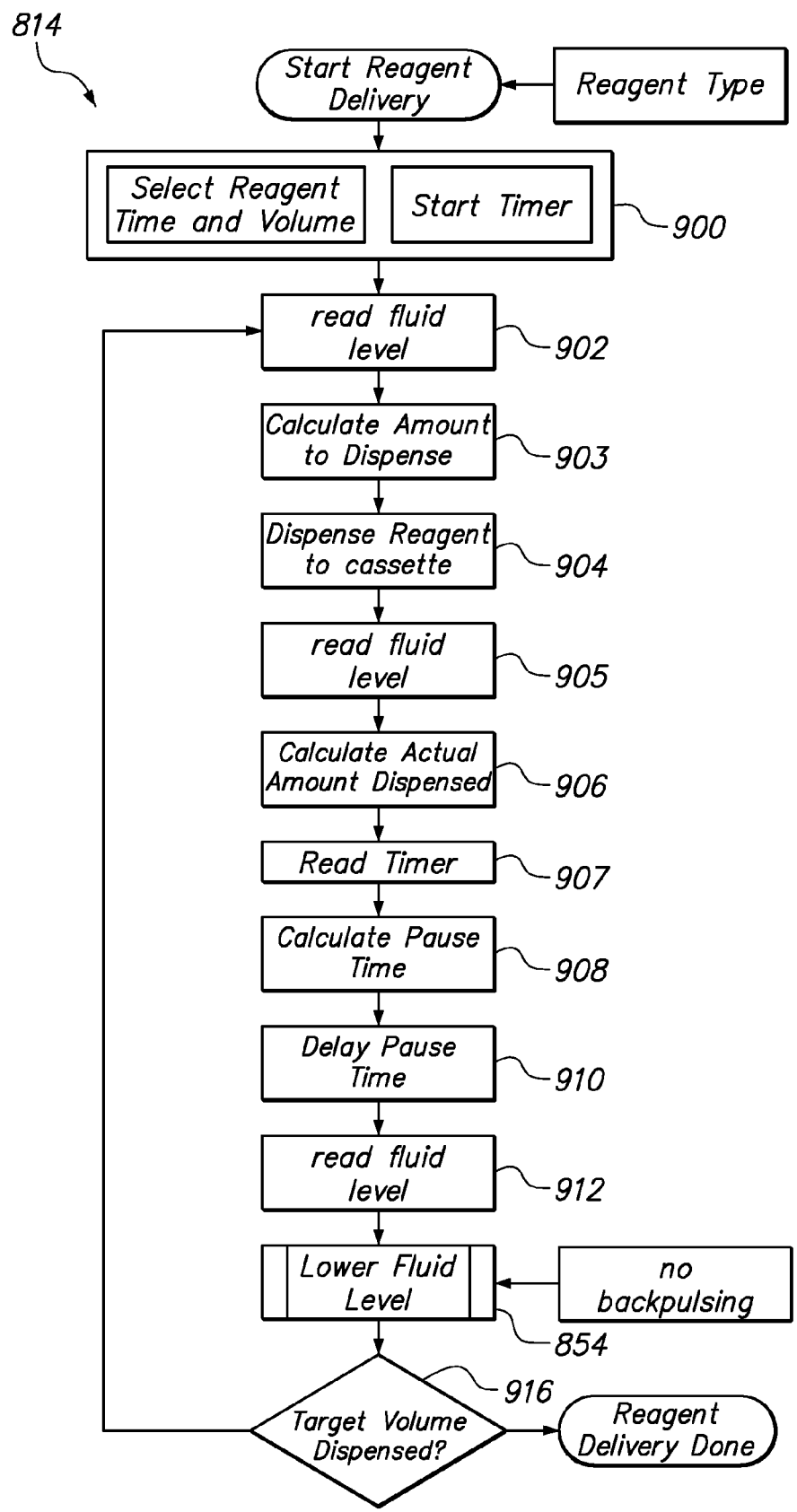
FIG. 19 is a flow chart of the reagent delivery process in the fluid delivery process of FIGS. 17A-B

Once the fluid level in the collection well is lowered to a minimum level (preferably at least some fluid is left in the collection well so that the retained cellular matter is not exposed to the air), the vacuum is turned OFF (850). The flow rate of the just-completed sample sip is then compared with a target flow rate (851). If the flow rate was greater than the target flow rate, and if the system did not "time out" while monitoring the fluid level (856), and if less than 20 ml of sample fluid have been dispensed (858), a new sample sip is commenced by returning to step 840. However, if the flow rate on the just finished sip was less than the target rate (851), or the system "timed out" while monitoring the fluid level (852), and if the cell processing was not "partially automated," (853, then the system undergoes a lower fluid level process (856) using back pulse of air pressure supplied from the waste chamber in order to momentarily lift the cellular matter off the filter and allow more sample fluid in the collection well to pass through. The details of the "lower fluid level" process (854) are shown in FIGS. 18C-D.

In particular, the lower fluid level process 854 begins by reading the fluid level in the sample collection (880) to ensure the level is high enough to turn ON the vacuum in the waste chamber to start drawing fluid out of the collection well (881). If the fluid level is not high enough to turn ON the vacuum, the lower fluid level process 854 is considered done. If there is sufficient fluid level to draw some down through the filter, then the vacuum is turned ON (882), and the system notes the time and fluid level (884) and monitors same every 20 milliseconds until the process is completed or times out. If a back pulse is "requested" (885), meaning the cell block process is fully automated and the fluid is sample fluid, the system next checks to make sure the fluid level is not too high for back pulsing (886), since otherwise the pressurized air coming up through the filter from the waste chamber can cause the sample fluid to splash out of the collection well. The controller also verifies that a previous back pulse was not administered within a predetermined interval (887) to ensure that back to back pulses are not administered. If the fluid level is not too high, and a previous back pulse has not been administered within the allowed interval, then the vacuum is turned OFF (888), and the source of pressurized air is put in communication with the waste chamber at a pressure sufficiently high to create a pressurized air back pulse (or "burp") (889) through the filter to lift the cellular matter away from the filter surface. The pressurized air is then turned OFF, and the vacuum turned back ON (890), to allow for the fluid to pass across the momentarily cleared filter.

Following application of a back pulse, the fluid level and flow rate continues to be monitored in the same manner as if no back pulse had been applied (in 20 ms cycles). The controller evaluates whether a "target level" is reached (892), which is based on a composite test that factors in both whether the fluid level is within a threshold of the lower limit (e.g., within about 10% of the total collection well height or volume) and the process has taken longer than a specified amount of time (e.g., approximately 40 seconds), in which case it is assumed that the system has pulled as much sample fluid through the filter as is needed, and the vacuum is turned OFF (895) the lowering fluid level process 854 is complete. On the other hand, if this target level is not reached after 90 seconds of processing time (894), and the process is ended with the user received a system error message (896), and the cell block processing ceases for that sample.

Returning to FIGS. 17A-B, if back pulsing through the filter allows the fluid to drain from the collection well prior to a "time out" (856), and if less than 20 ml of sample fluid have been dispensed (858) and the flow rate is lower than the target flow rate (860), then the vacuum rate may be increased (864) (e.g., from 10% to 50% following an initial sample sip) and a new sample sip is commenced by returning to step 840. Notably, in embodiments of the invention, the vacuum rate is not raised higher than 50% of maximum for pulling sample fluid. However, if despite back pulsing through the filter the fluid does not drain from the collection well prior to a "time out" (856), or if 20 ml of sample fluid have been dispensed (858), or if the flow rate drops below the target flow rate (860) at the full vacuum strength applied for pulling sample fluid (862), then no more sample fluid is dispensed into the collection well.

Returning to FIG. 15, once the aspiration and dispensing of the sample fluid is complete, eosin stain is (optionally) injected into collection well (812) by the automated arm assembly. In particular, the controller closes the valve on the alcohol feed line at the pipette tip holder and the opens the valve on the eosin feed line. Because the eosin container is pressurized, the eosin self-dispenses through the same pipette used for the sample fluid into the collection well, and the automated arm need not be repositioned. Once the desired amount of eosin stain has been dispensed, the controller closes the valve on the eosin stain feed line, and selectively re-opens the valve on alcohol feed line, and the syringe pump is activated to meter out the isopropyl alcohol (a drying reagent to displace the water content from the cellular mater) into the collection well according to the reagent delivery process (814) illustrated in FIG. 19.

In particular, the controller selects the reagent (in this case, the alcohol), starts a timer (900), and reads (detects) the fluid level of the remaining sample fluid in the collection chamber (902) in order to calculate how much alcohol to initially dispense (903) without overflowing the collection well. The calculated amount of reagent (alcohol) is then dispensed (via precise operation of the syringe pump) into the collection well (904) and the fluid level is again read (905) to verify the actual amount that was dispensed (906). The timer is then read (907), followed by a calculated ouase time (908) and delay pause time (910). Essentially: the controller calculates the amount of time to wait before passing the reagent through the filter in order to adequately expose the cellular material to the respective reagent. If the flow is fast, the total time needed to fill and empty the collection well such that the volume is dispensed may be less than the specified exposure time. So, the system preferably delays a bit in each reagent dispense process to compensate. Roughly, the exposure times the number of fills minus the time to lower level in the last iteration.

The fluid level is read again (912) and the lower fluid level process 854 (FIGS. 17A-B) is performed, except that no back pulsing is done. At that point, the controller determines whether the target volume of the reagent (alcohol) has been dispensed, and for the required exposure time (916). If so, then the reagent delivery process is done. If not, the process returns to step 902 and is repeated.

Once the alcohol has been fully dispensed, the controller closes the valve on the alcohol feed line, and selectively opens the valve on the (pressurized) xylene feed line, as the reagent delivery process (814) is repeated for dispensing xylene (a clearing reagent to eliminate the alcohol). For a fully automated process, preferably 3.0 ml each of isopropyl alcohol and xylene are respectively dispensed, with at least 90 seconds of exposure of the cellular material to each reagent in the collection well. For a semi-automated process (meaning some cell fragments are manually introduced into the cell collection well), 15 ml of alcohol for at least 5 minutes exposure is followed by 20 ml of xylene for at least another 5 minutes exposure. In either case, the remaining xylene is vacuum pulsed out of the collection chamber just prior to when the paraffin is first dispensed therein.

Returning to FIG. 15, with a small portion of the xylene still in the collection well to prevent the cell layer from direct air exposure, the collection well is heated (818) via heating the metallic support member 59 underlying the filter 60. The reason for heating the collection well is to prevent the liquefied paraffin from immediately solidifying upon contact. The automated arm disposes of the pipette used for the sample fluid, stain and reagents, and connects to a new pipette tip at the wax station. Using a separate pipette tip for aspirating the paraffin than was used for aspirating the sample fluid helps avoid cross-contamination between cell samples. For this same reason, a separate pipette tip is preferably used each time additional paraffin is aspirated from the wax bath.

Figure 20B:
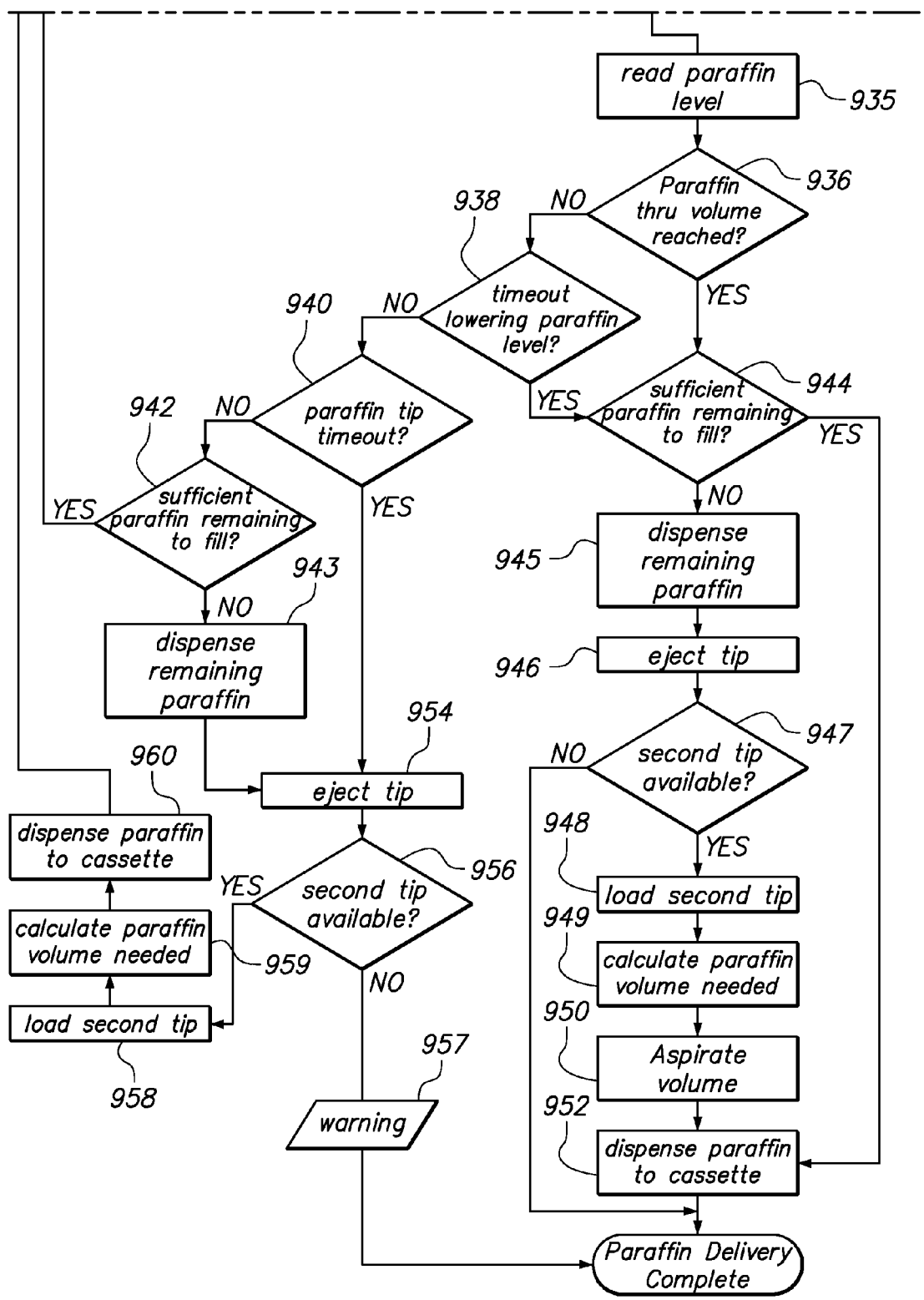
Figure 21A:
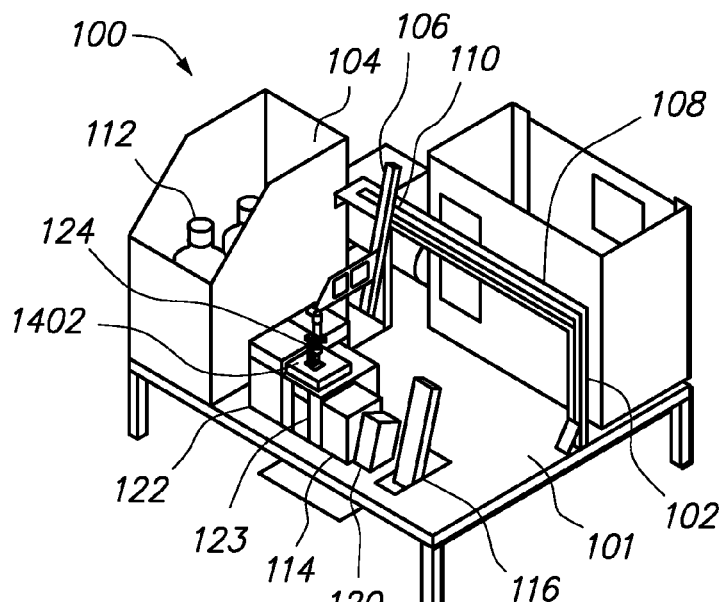
FIG. 21A-E are respective perspective, top and side views of another embodiment of a cell block processing station constructed according to embodiments of the disclosed inventions.
Figure 21B:
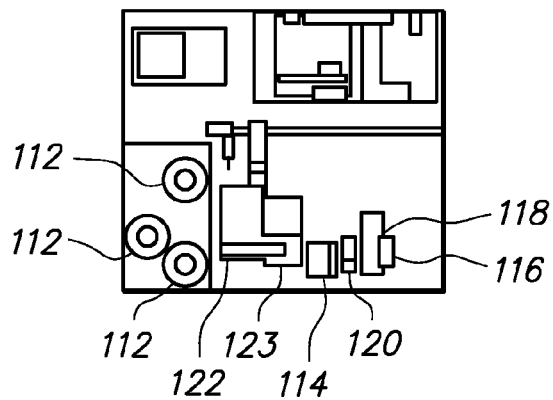
Figure 21C:
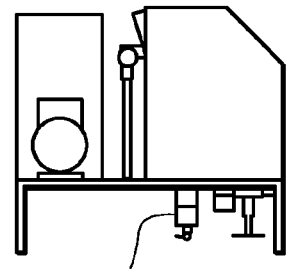
Figure 21D:
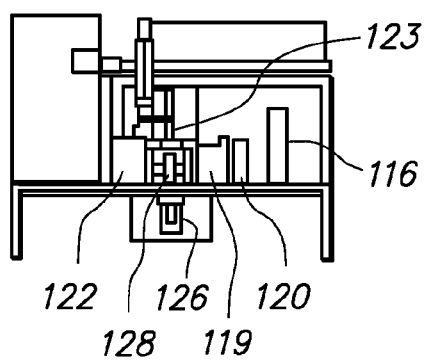
Figure 21E:
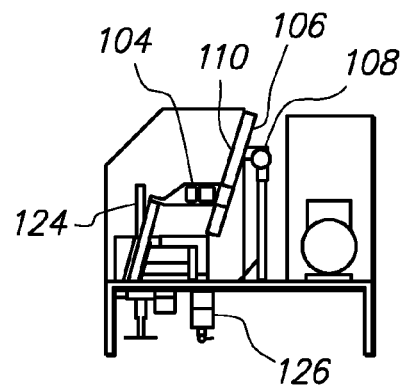
Figure 21F:
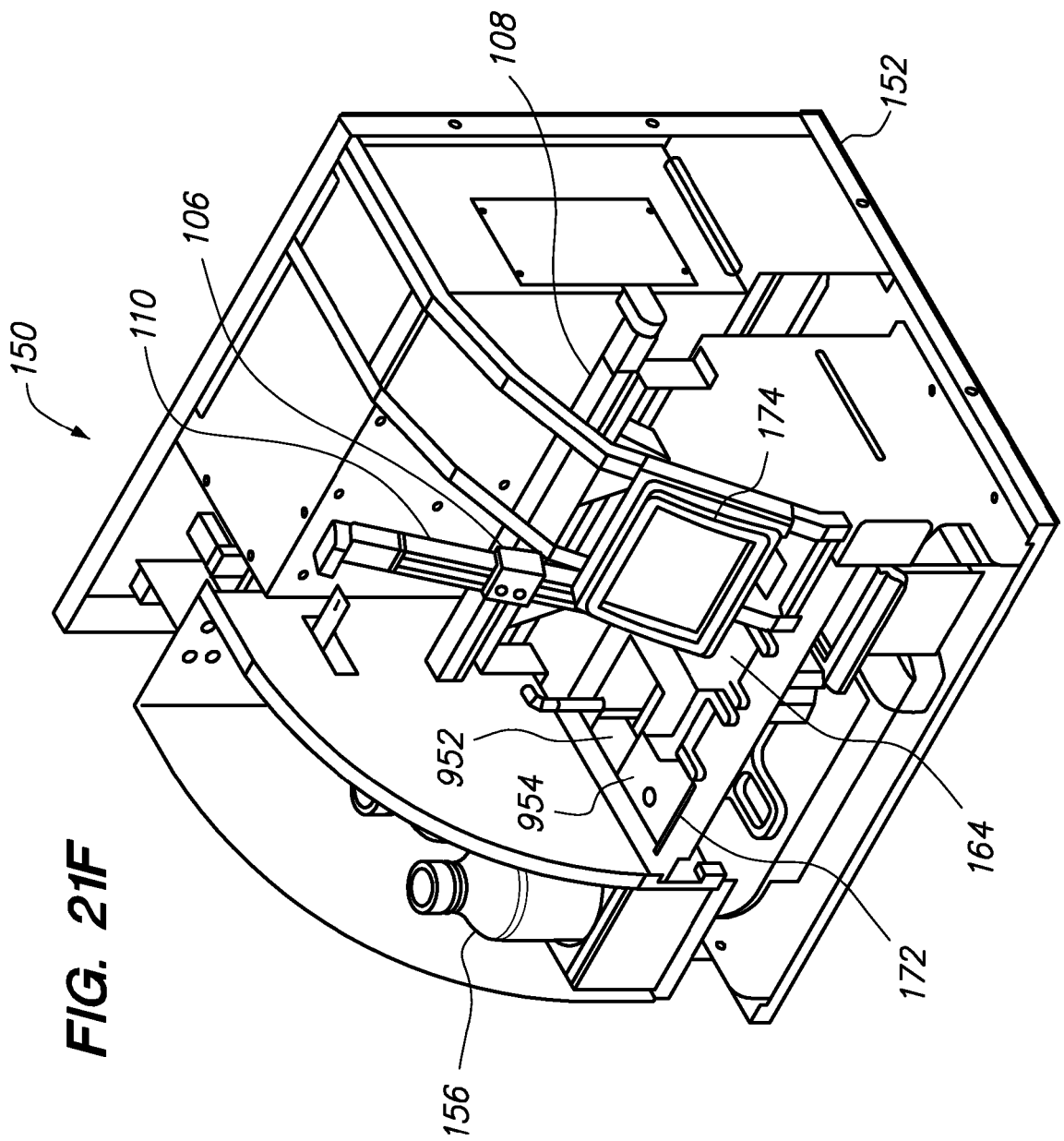
FIG. 21F-J are respective perspective, top and side views of yet another embodiment of a cell block processing station constructed according to embodiments of the disclosed inventions.
Figure 21G:
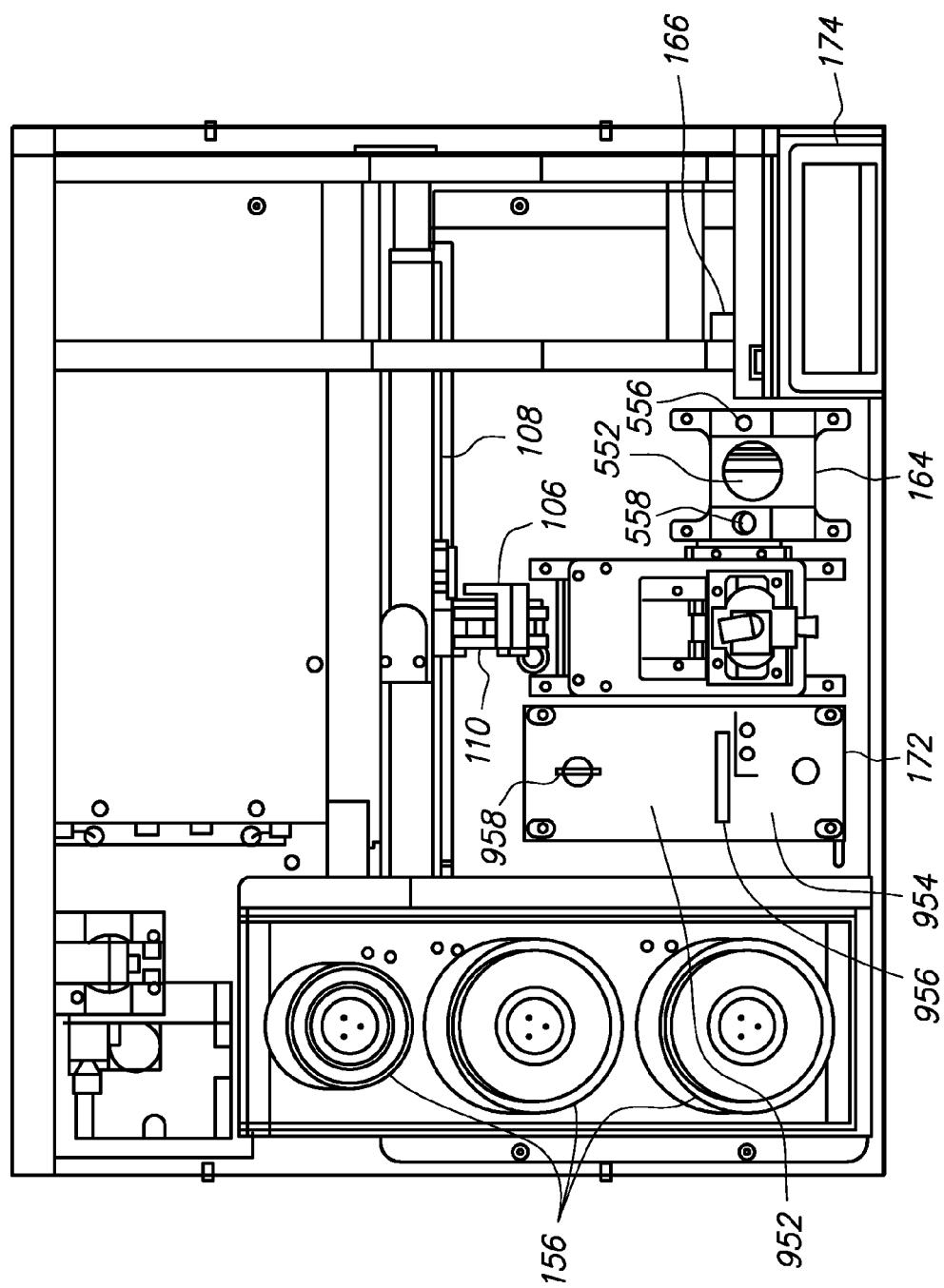
Figure 21H:
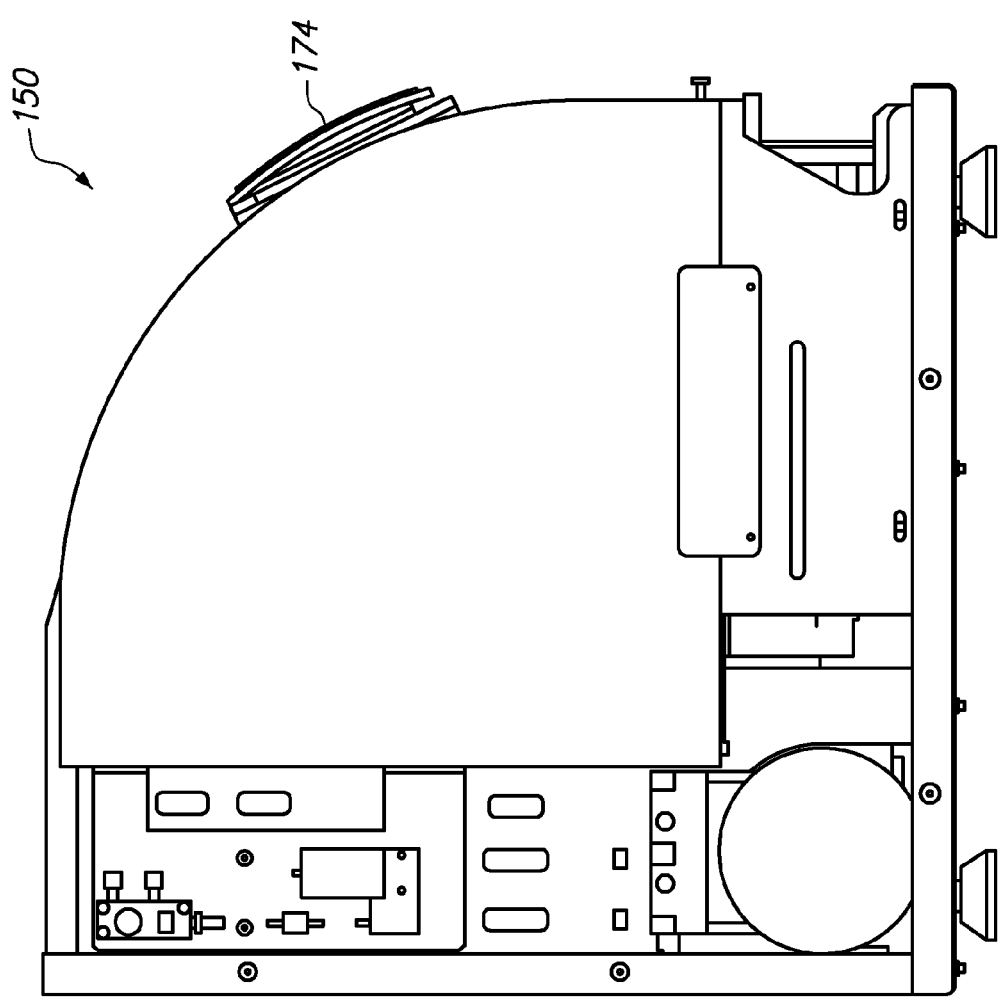
Figure 21I:
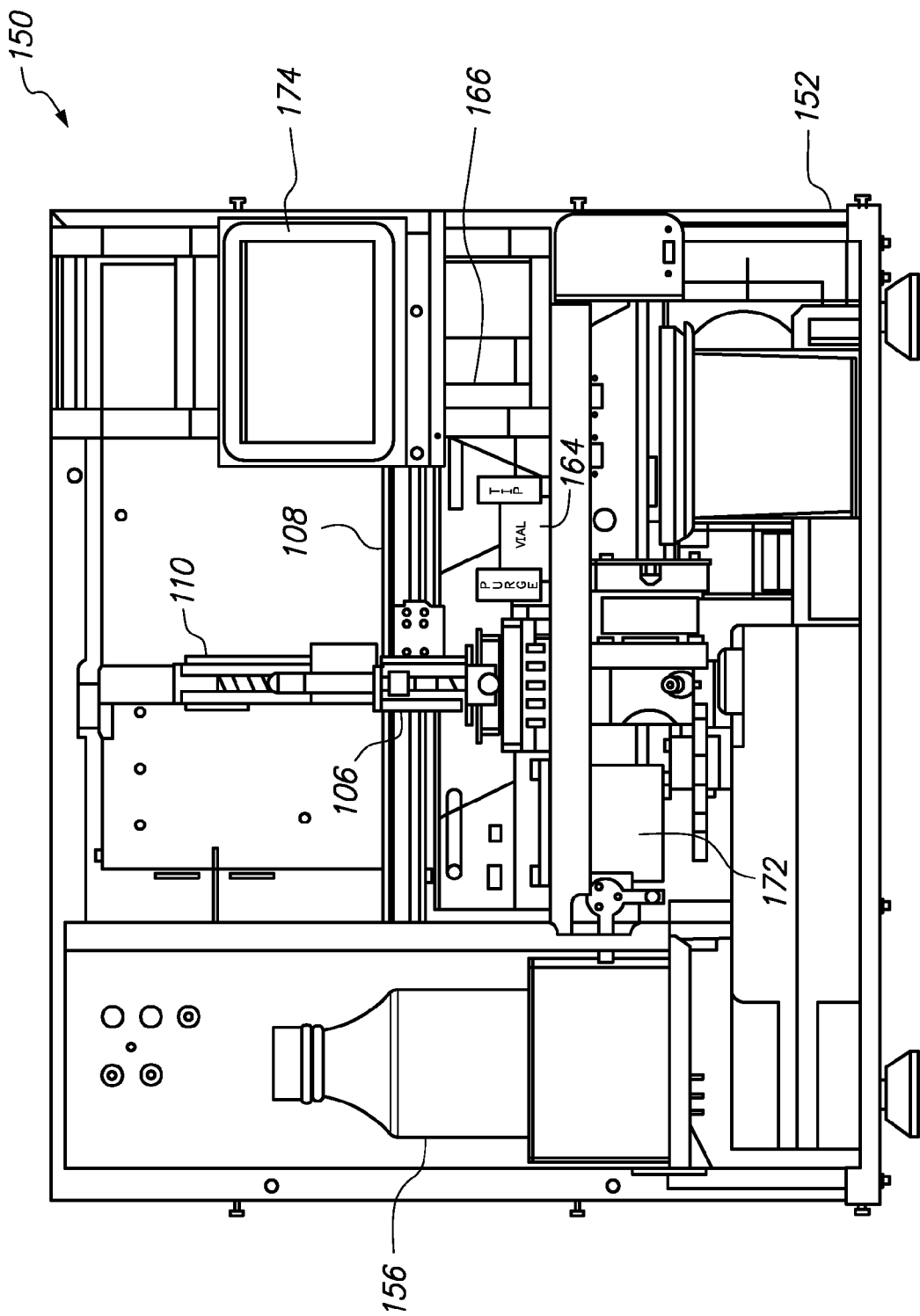
Figure 21J:
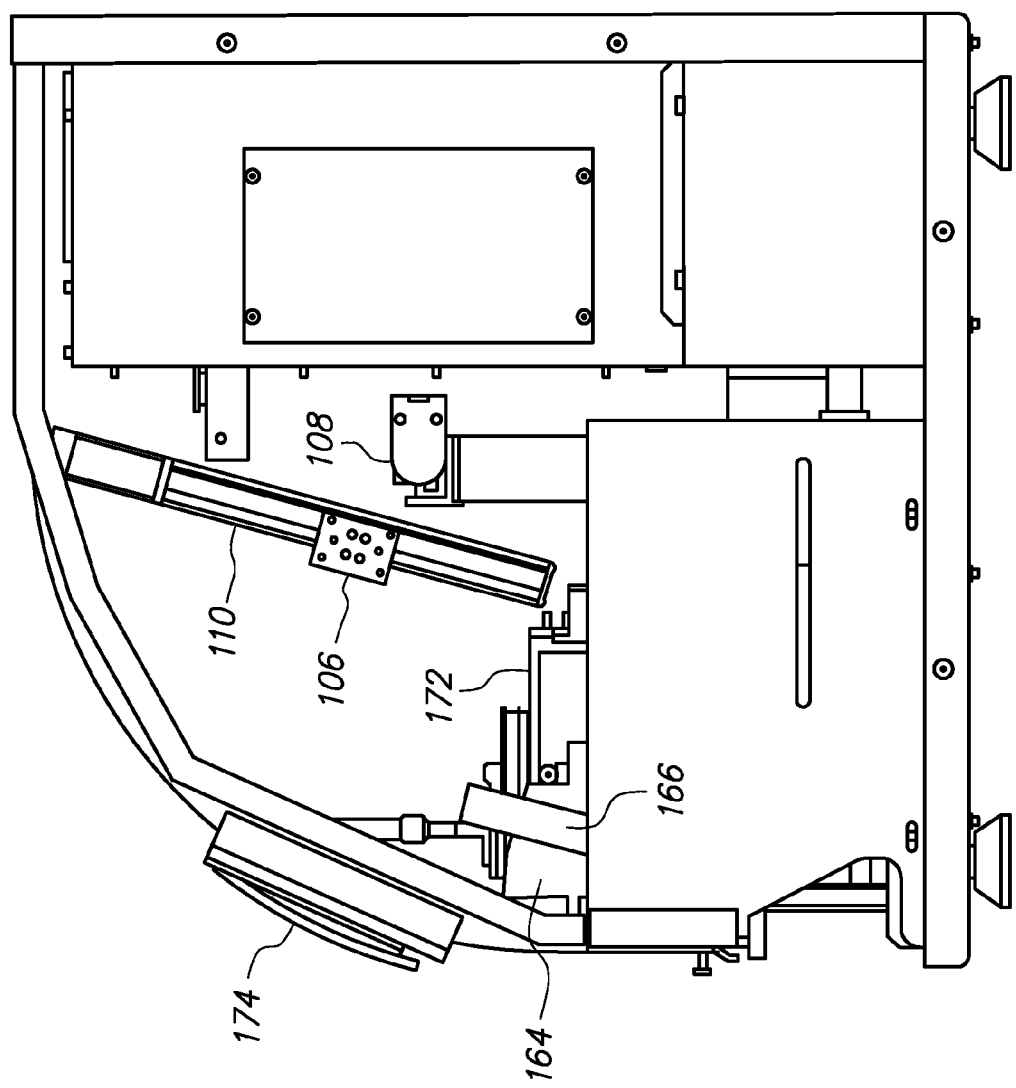

The process for delivery of the paraffin (820) is illustrated in FIGS. 20A-B. In particular, a new pipette tip (located at the wax bath station) is secured to the pipette tip holder (920), and the controller again reads the fluid level in the collection well (921). As the newly secured pipette is dipped into the wax bath and loaded with a first volume of the liquefied paraffin, the waste chamber vacuum is switched ON (full strength) to remove the residual xylene through the filter and then switched back OFF (922). The liquefied paraffin is then dispensed into the collection well (924), and the vacuum is switched back ON (925) to draw the liquefied paraffin into the cellular matter, through the filter pores and into the waste chamber, to thereby fully embed the cellular matter that was retained by the filter. The flow of the paraffin is monitored in the same manner as the prior fluids, by tracking the fluid level in the collection well and the elapsed time (927). The level of the paraffin is compared to a desired low level (928) indicating a full absorption of the wax into the cellular matter. Once the desired absorption level is detected by the sensor, the vacuum is switched off (934). In the mean time, if the absorption level is not yet reached prior to the system timing out (930). In the case of a "time out" on the paraffin level lowering watch, the vacuum is shut OFF. Similarly, a further "time out" (932) is monitored by the controller to track the time that the liquefied paraffin has been in the pipette tip. Because the paraffin can quickly solidify, preferably no longer than 30 seconds is provided for this "paraffin tip" time out period.

Whether because of the level sensed, or a "time out" was reached, once the vacuum is shut OFF, the controller again reads the fluid level in the collection well (935) to determine whether the desired paraffin through volume has been reached (936). If so, (or if there was a "time out" for the lowering paraffin level watch), then the controller determines what liquefied paraffin remains in the pipette tip (944), dispenses same into the collection well (945), and ejects the pipette tip (946). If a further pipette is available (947), the further tip is retrieved by the pipette holder (948), loaded with further liquefied paraffin from the wax bath (949/950), and dispensed into the collection well (952) to fully encapsulate the cellular matter. If at step 936 the desired paraffin through volume is was not reached, and there was not a "time out" on the lowering paraffin level watch (938) or a paraffin tip time out (940), then (again), the controller determines what liquefied paraffin remains in the pipette tip (942), dispenses same into the collection well (943), and ejects the pipette tip (954). Further steps 956 (verifying a second pipette tip is available), 958 (loaded the second tip on the pipette tip holder), 959 (calculating what remaining paraffin is needed) and 960 (dispensing same into the collection well), are then performed, as illustrated in FIG. 20B. In the event no second pipette tip is available, a warning is sounded to the user, and the paraffin delivery process ceased (957).

For a fully automated process, approximately 1.5 ml of paraffin is introduced and held at temperature to assure the paraffin remains melted with an exposure time of 20 seconds. In a semi-automated process, 1.5 ml of paraffin is introduced and kept molten for at least 7.5 minutes. Using separate pipette tips for aspirating the sample fluid and for dispensing reagents versus aspirating the paraffin helps avoid cross-contamination between cell samples. This is the same reason that separate pipette tips are used for aspirating paraffin if more than one aspiration from the wax bath is needed.

Extra care must be taken when dispensing the paraffin to be sure that the pipette tips do not become clogged with solidified pieces of wax, or that solidified pieces are introduced into the collection well, as this may cause the cell block to later crack or fall apart. Thus, the system imposes a strict time limit on how long it will allow continued dispensing of paraffin from the same pipette tip. After the paraffin is introduced and drawn into the cellular material (and through the filter 60 and substrate 59) by the vacuum, a further quantity is poured into the well with the vacuum off, in order to fully embed the cellular matter. The collection well is then chilled (822 in FIG. 15), e.g., by reversing the peltier system used to heat the substrate 59 so that it now chills the substrate, to solidify the paraffin in the collection well prior to when the operator removes the cassette and newly formed cell block from cassette interface and removes the filer assembly from the cassette and paraffin block. In order to separate the filter assembly 14 from the main cassette body 13, it may be advisable to first chill the already solidified paraffin to cause further thermal contraction of same. This can be accomplished, for example, by spraying a cold gas (compressed air) onto the cell block or placing it in a freezer for a short period of time. As the wax contracts, it releases from the respective filter and support member.

Figure 12:
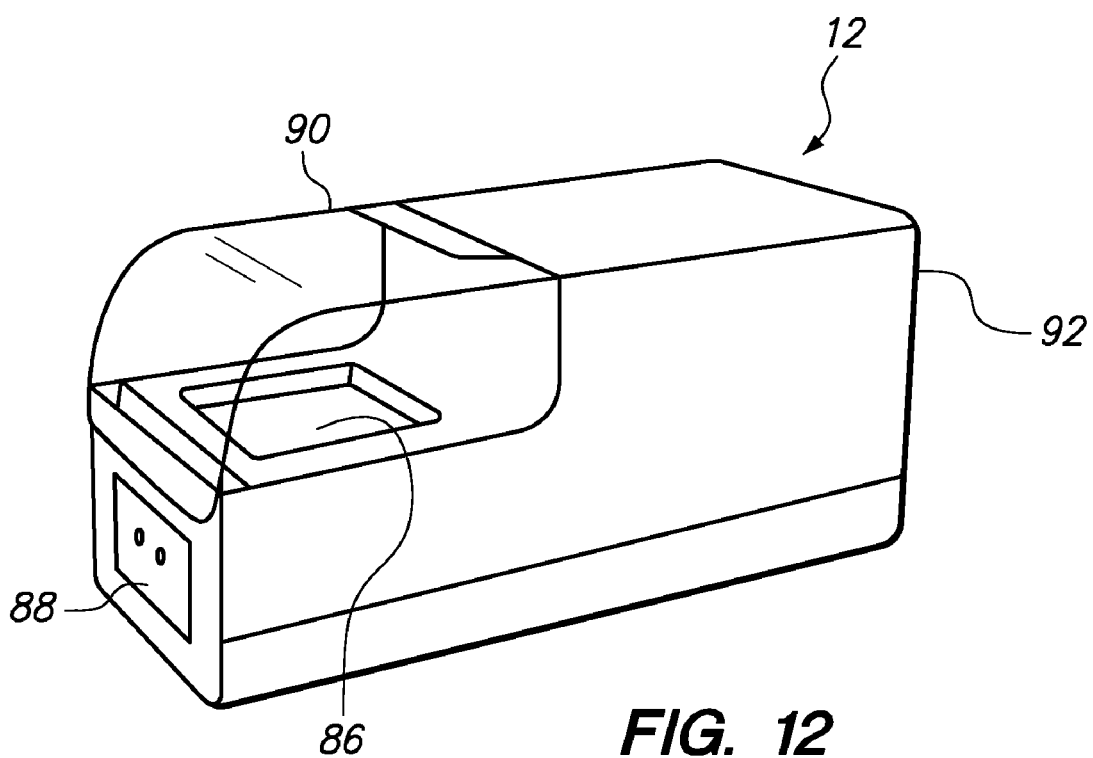
FIG. 12 is a perspective view of the finishing station.
Figure 14:
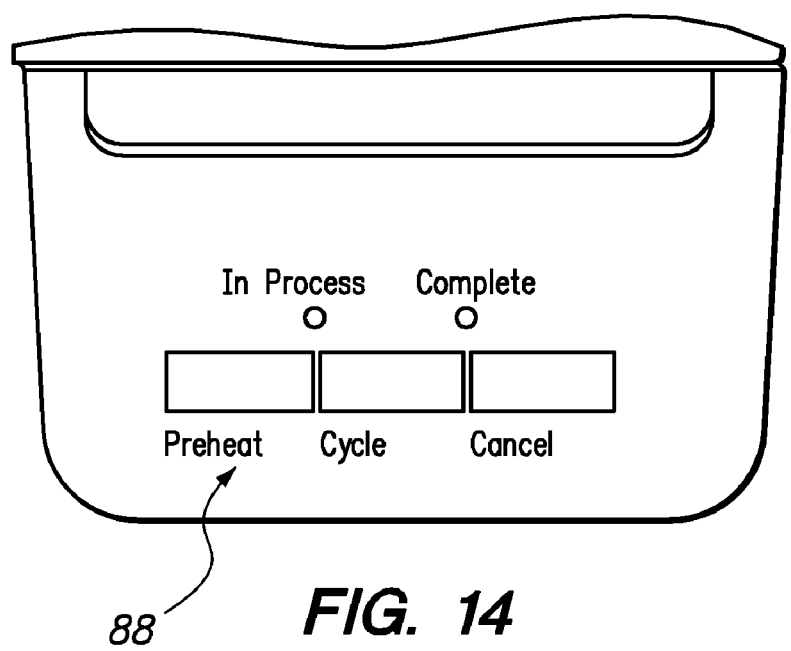
FIG. 14 shows the user interface on the finishing station.
Figure 13A:
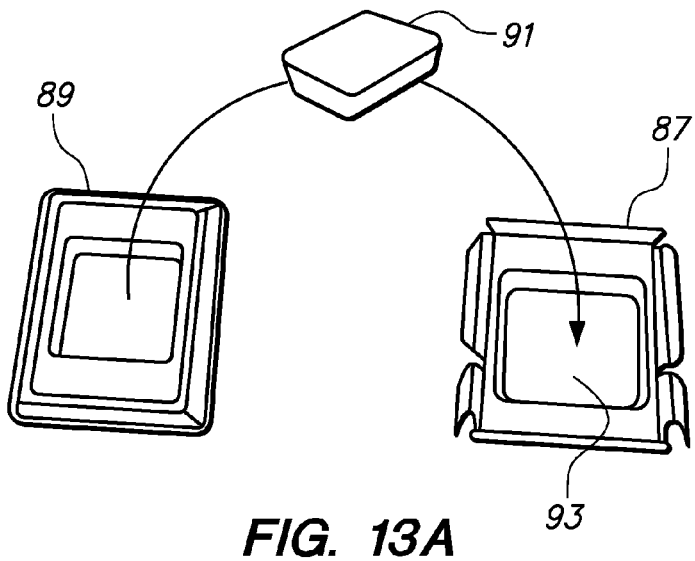
FIGS. 13A-13C depict placement of an additional paraffin block and cell block cassette in a thermally conductive mold for thermal treatment using the finishing station.
Figure 13B:
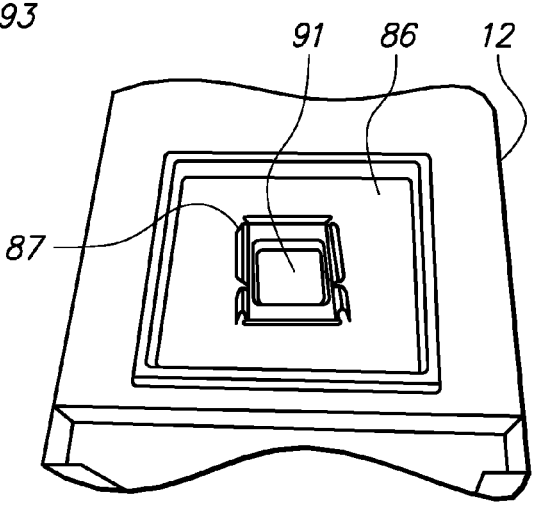
Figure 13C:
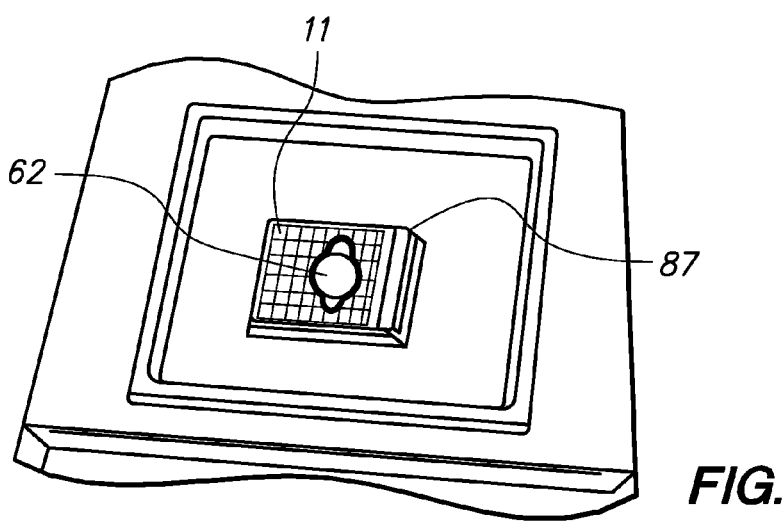

FIG. 12 is a perspective view of the finishing station 12, which generally includes a housing 92 for enclosing the processor and electronics and heat exchanger, a thermally conductive heating/cooling plate 86, a simple user-interface (control panel) 88 (FIG. 14), and a clear plastic cover 90 for the heating/cooling plate 86. As illustrated in FIGS. 13A-13C, the finishing station is used to embed the cell block in additional paraffin, in particular the end of the cell block containing the cell layer.

In particular, a piece of paraffin 91 is first transferred from its packaging 89 into the re-melt well 93 of thermally conductive (e.g., stamped metal) embedding mold 87 (FIG. 13A). The embedding mold 87 is then on the heating/cooling plate 86 on the finishing station 12 (FIG. 13B), and the operator starts the unit using the user interface 88 begin melting the wax 91. When the embedding wax 91 is completely melted (about seven minutes), the cell block cassette 11 is placed into the well 93 of the mold 87 by fitting one end into the mold 87 and lowering the cassette until it is fully inserted into the mold, with the cell block paraffin side face side and into the liquid paraffin. Preferably, no air bubbles are trapped between the melted paraffin and the cell block paraffin. The unit then continues to apply heat to the plate 86, until the embedding paraffin on the cell block has softened and started to melt. At this point, the plate is abruptly switched over to cooling. In particular, it is important that the re-melt process employ be fast and controlled heating, followed by fast and controlled cooling. In one embodiment, a method for the paraffin re-melt includes placing the paraffin-embedded cellular material atop an additional amount of paraffin; controllably heating to thereby soften and at least partially blend together the embedding paraffin and additional paraffin, without softening or liquefying the embedding paraffin to a point that the retained cellular material therein breaks apart and disburses through the embedding paraffin; and controllably cooling to thereby bond the additional paraffin to the embedding paraffin.

Figure 22A:
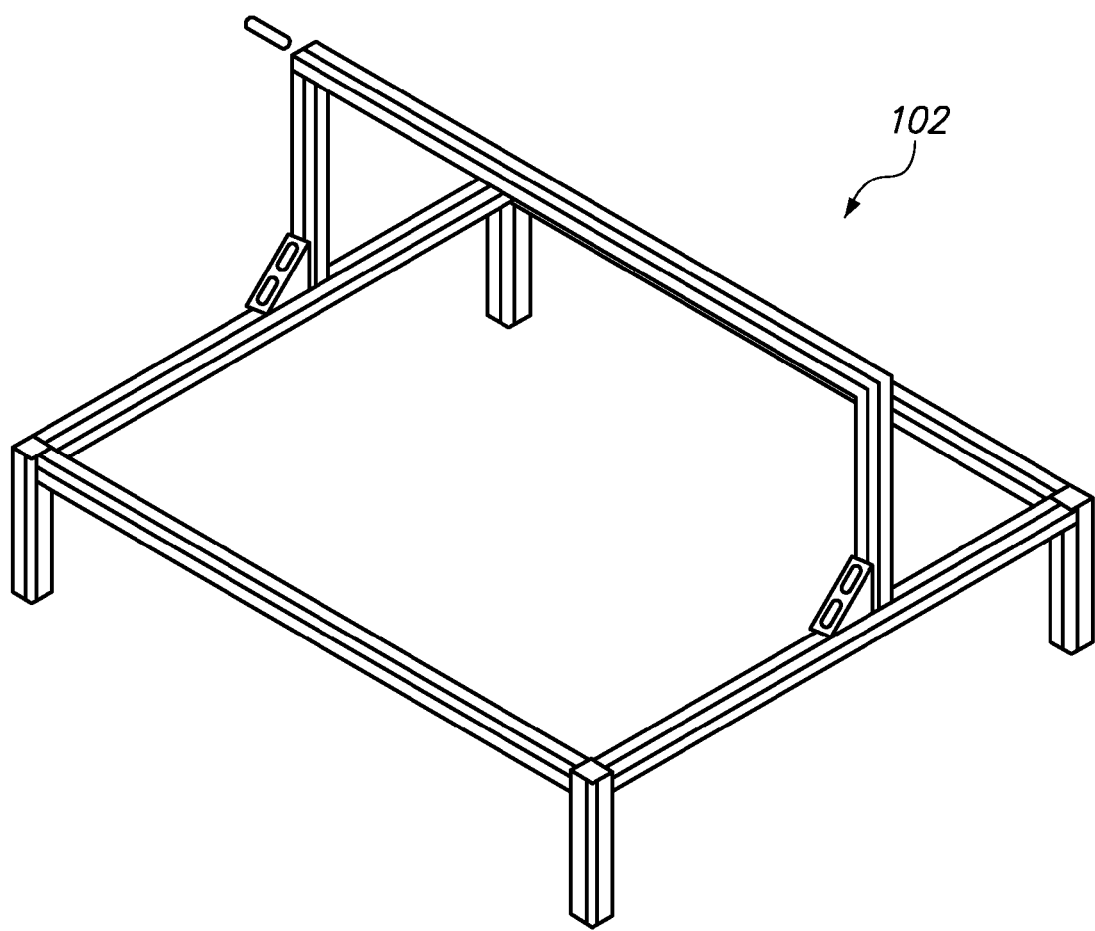
FIG. 22A depicts a base frame of the processing station of FIGS. 21A-E.
Figure 22B:
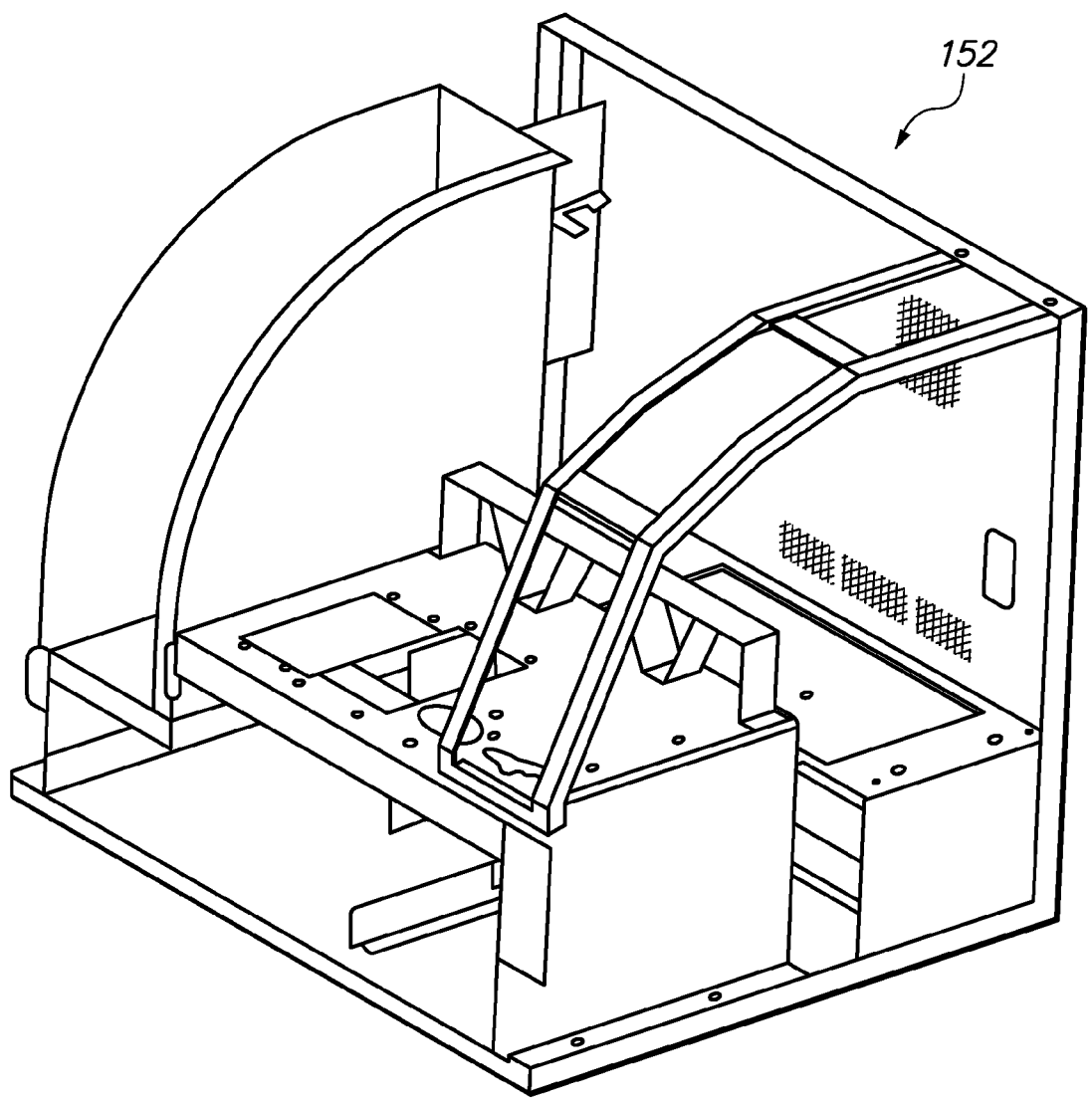
FIG. 22B depicts a base frame of the processing station of FIGS. 21F-J.

FIGS. 21A-J depict further embodiments of a cell block processing station, which are similar if not identical in most aspects to the processing station 10 of the above-described system 20, and are being shown and described herein to provide additional details regarding making and using embodiments of the disclosed inventions. In particular, FIGS. 21A-E depict the structures and features of one processing station 100, which are assembled on a respective base 101 and base frame 102, shown in FIG. 22A. FIGS. 21F-J depict the structures and features of another processing station 150, which are assembled on a base frame 152, shown in FIG. 22B.

Figure 23A:
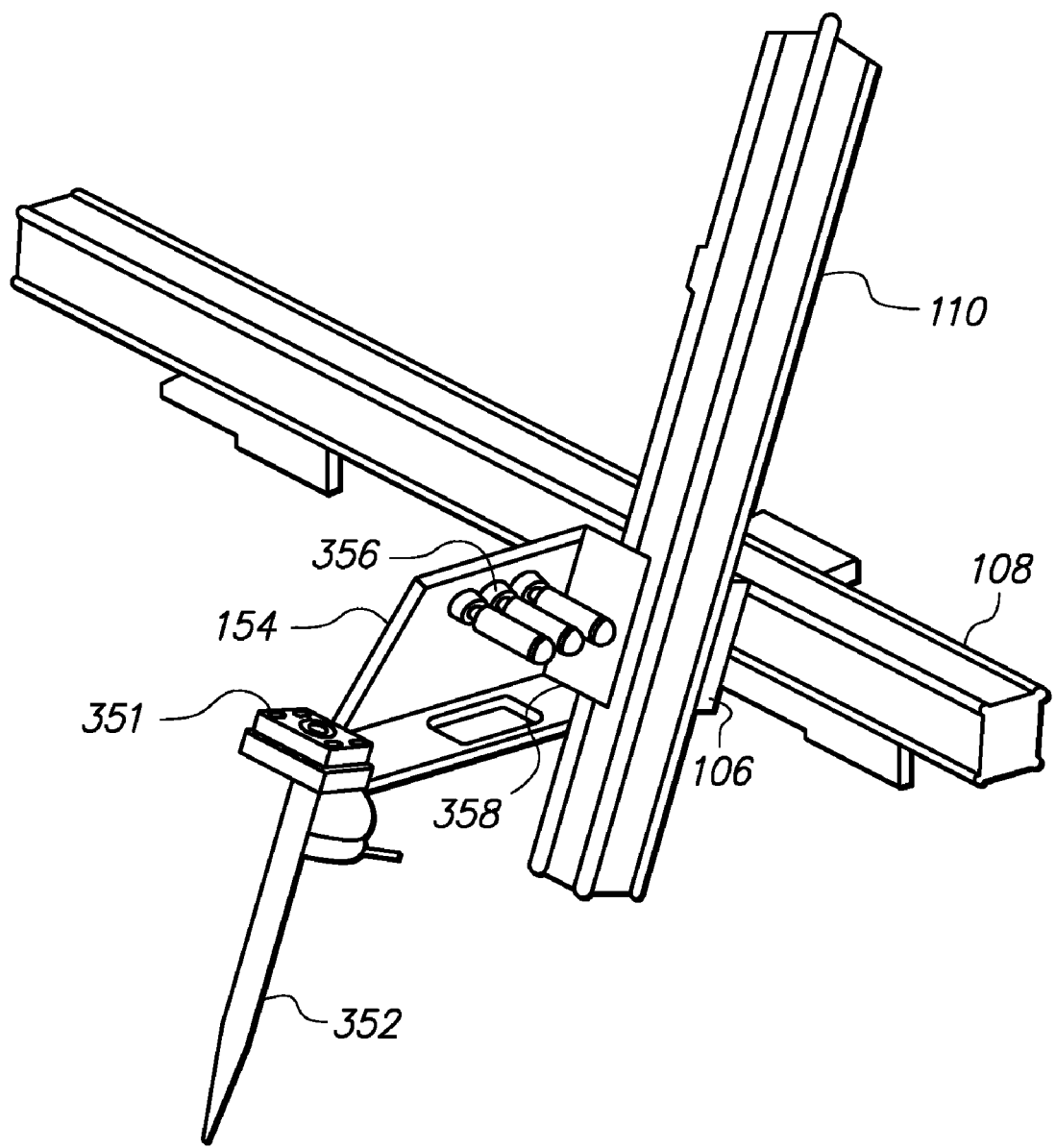
FIGS. 23A to 23D are perspective representations embodiments of an automated arm assembly for use in the cell block processing station embodiments disclosed herein.
Figure 24A:
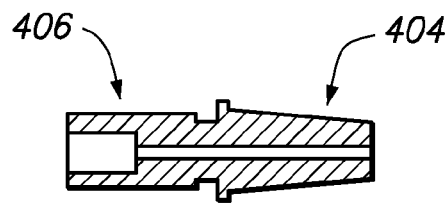
FIGS. 24A and 24B depict one embodiment of a pipette tip connector for use with the automated arm assembly.
Figure 24B:
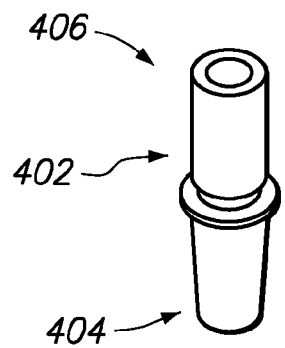

A sample arm 104 is connected to the base frame 102 of the processing station 100 by a robotic arm 106. FIG. 23A shows a perspective drawing of the sample arm 104. The robotic arm 106 is configured to move laterally along the base frame 102 on a horizontal railing 108. The robotic arm 106 can also move vertically with respect to the base frame 102 along a vertical railing 110. The vertical railing 110 is connected to the horizontal railing 108. Thus, using a combination of the horizontal railing 108 and vertical railing 110, the sample arm 104 can move to various locations within the processing station 100. In particular, the vertical railing 110 is preferably connected to the horizontal railing 108 at a slight angle from perpendicular, e.g., approximately 15° (so that the vertical railing 110 forms an angle of approximately 75% with the horizontal railing 108), in order to allow a tip of an attached pipette to pass by a level sensor 124 aligned over the cassette well. To the sample arm 104 is attached a pipette connector 402, as shown in FIGS. 24A-B. The lower end 404 of the pipette connector 402 is configured to attach to a pipette, such as a disposable plastic pipette.

A plurality of tubes, not shown, are connected to the upper end 406 of the pipette connector 402 when the pipette connector 402 is placed on the sample arm 104. One of the tubes is a vacuum tube, which is filled with alcohol (as a source of reagent, the use of which is described below) and connected to a vacuum source, not shown. When a pipette is attached to the pipette connector 402 and the distal tip of the pipette is immersed in a fluid, the vacuum causes the fluid to flow into the pipette.

Other tubes connected to the upper end 406 of the pipette connector 402 cause the pipette connector 402 to be in fluid communication with a plurality of liquid sources 112. The liquid sources 112 hold reagents, such as xylene and alcohol, used for the preparation of cell blocks.

Figure 25:
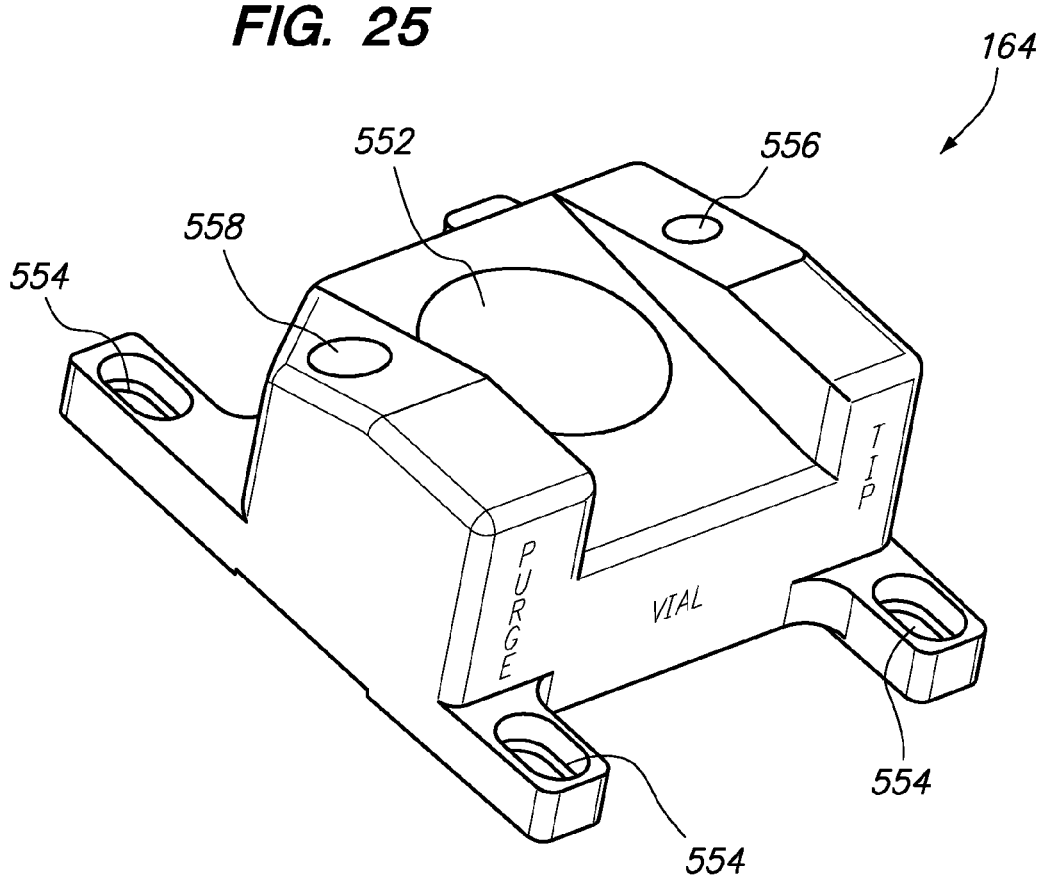
FIG. 25 is a perspective representation of one embodiment of a sample vial interface (or holder) block.

A vial holder block 114 is located in the processing station 100. The vial holder block 114, also shown in FIG. 25, is configured to hold a vial containing a biological sample. The biological sample comprises cells that are to be embedded in wax.

Figure 26:
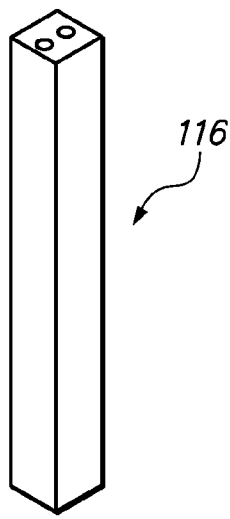
FIG. 26 is a perspective representation of one embodiment of a pipette tip removal post.
Figure 27:
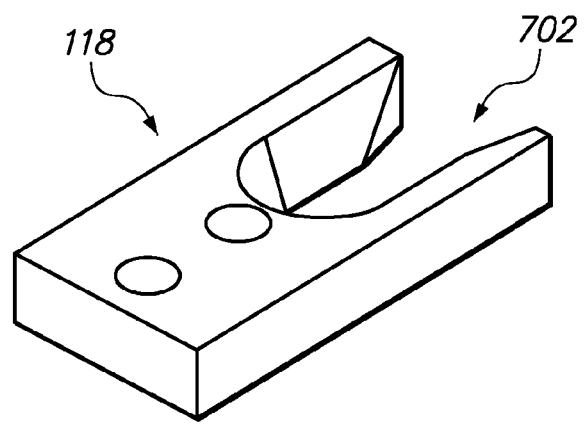
FIG. 27 is a representation of an embodiment of a pipette tip removal knife.

The processing station 100 also comprises a pipette removal element. The pipette removal element comprises a pipette removal post 116, also shown in FIG. 26, and a pipette removal knife 118, also shown in FIG. 27. The pipette removal knife 118, which is mounted on top of the pipette removal post 116, comprises a flared opening 702. When the pipette connector 402, having a pipette attached thereto, is laterally inserted into the opening and then moved upward, the pipette is then detached from the pipette connector 402. A liquid waste line is provided into which the contents of a pipette tip can be disposed.

Figure 29:
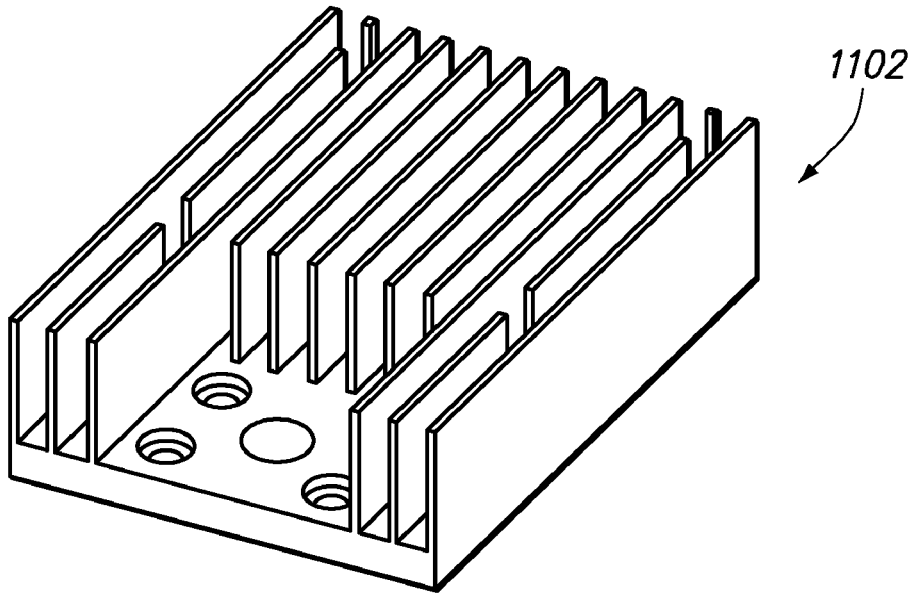
FIG. 29 is a representation of an embodiment of a heatsink.

The processing station 100 includes a sample platform 123. In some embodiments, the sample platform 123 comprises a heatsink 1102 (FIG. 29). A top plate 1202 (FIG. 31) covers the heatsink 1102. A cell block cassette and filter assembly holder 1302 (FIG. 32), is configured to be placed in the opening 1204 of the top plate 1202. The cassette holder 1302 is configured to hold a cassette assembly (e.g., the cell block cassette 11). A clamp plate 1402 (FIG. 33) is configured to be placed over the cassette holder 1302, such that the opening 1404 of the clamp plate 1402 is placed over the opening 1304 of the cassette holder 1302.

Figure 34:
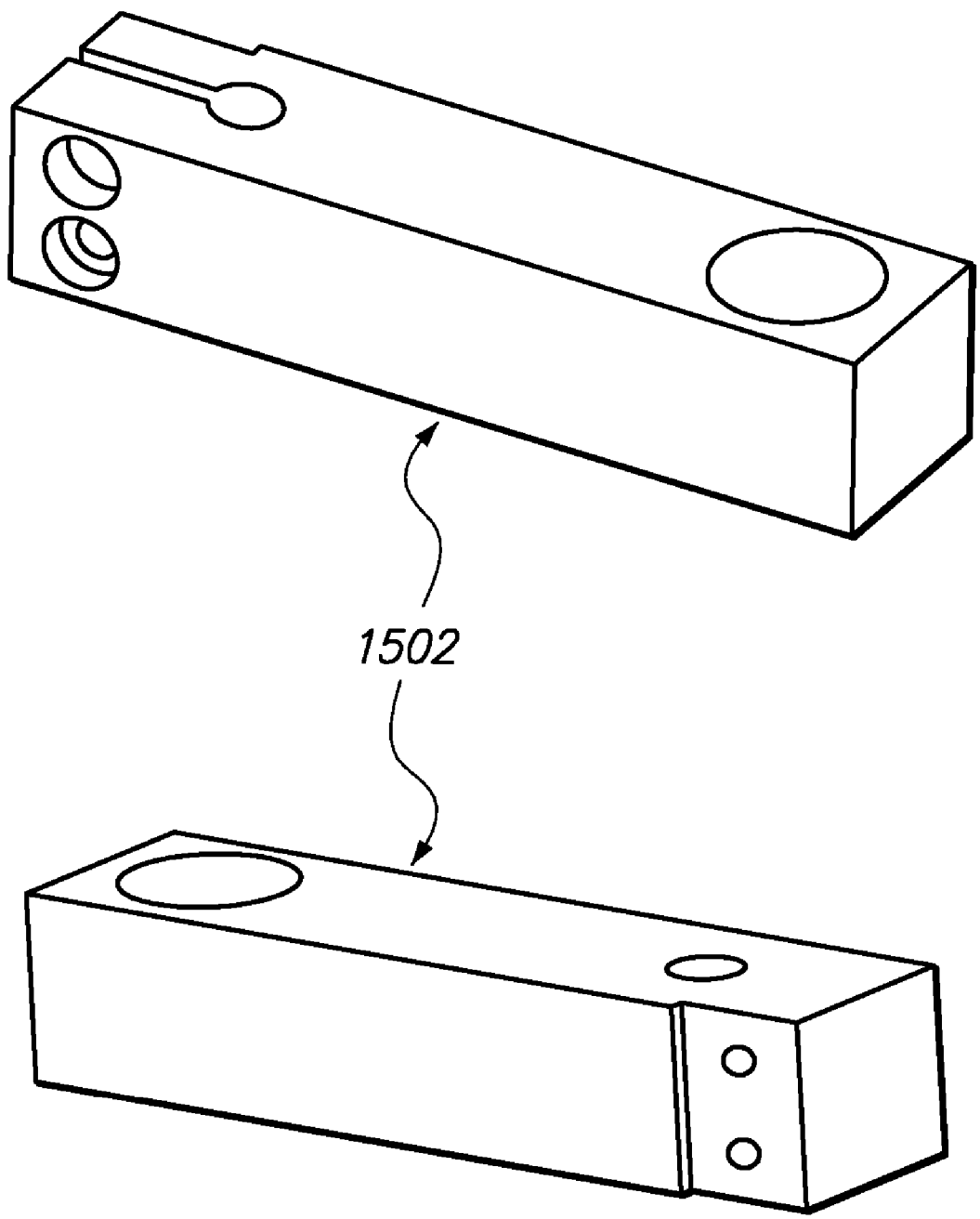
FIG. 34 is a representation of one embodiment of a sensor arm.

A sensor 124 is provided, which measures the level of liquid in the cassette well 1612, for example, using ultrasound wave energy, as is done in the ML series of ultrasonic sensors produced by Cosense. The sensor 124 is held in place by a sensor arm 1502 (assembly shown in FIG. 34).

The processing station 100 also includes a vacuum source 126. The vacuum source 126 is connected to the cell block sealing surface 52 on the filter assembly 14, through an airtight channel 128 so that it can apply vacuum to the collection well and draw liquid through the filter 60. The liquid drawn from the collection well is held in the waste chamber 39. In some embodiments, the vacuum source 126 comprises a pressure gauge that can measure the pressure differential between the air over the collection well 1612 and the air-tight channel 128.

FIGS. 21F-I depict the components of processing station 150, which are all attached to the base frame 152. The processing station 150 includes the same robotic arm 106, horizontal railing 108, and vertical railing 110 as station 100, which operate in a similar manner as described above.

Figure 23B:
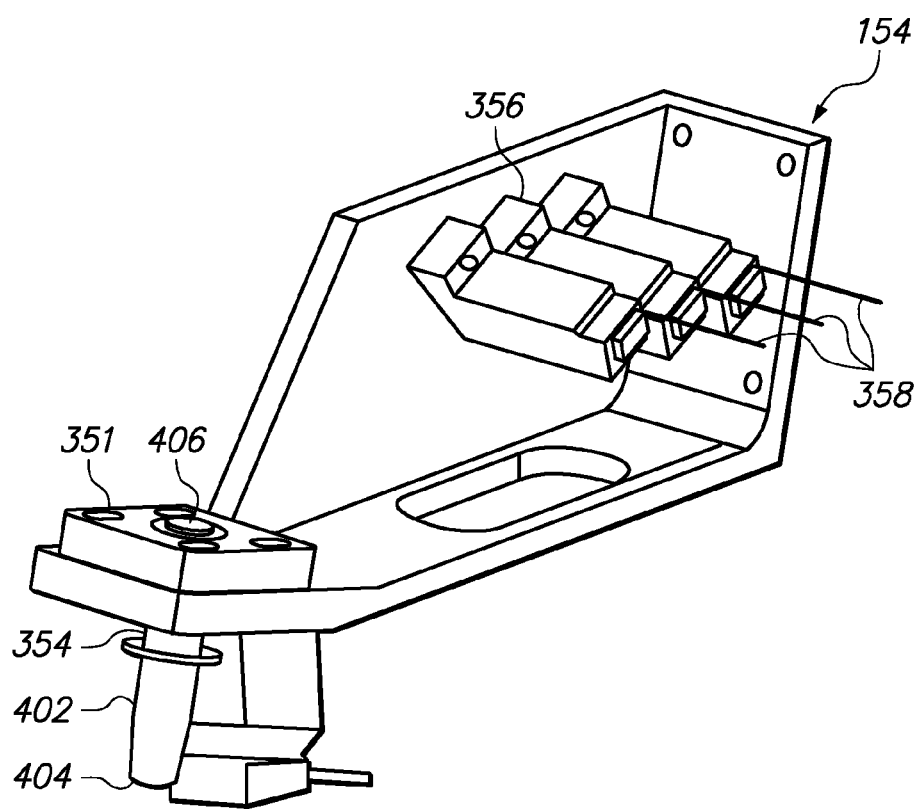
Figure 23C:
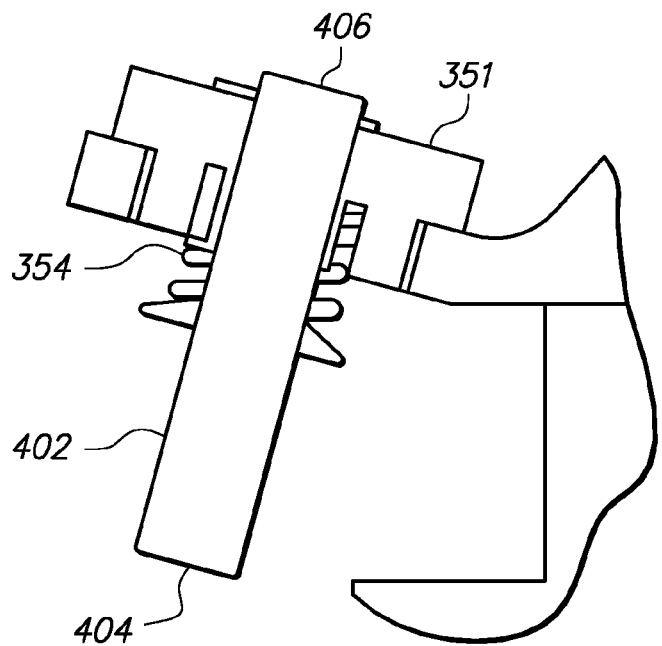

FIG. 23B shows a sample arm 154 is connected to the horizontal railing 108 and the vertical railing 110 of the processing station 150 by a robotic arm 106. FIG. 23C shows a perspective drawing of the sample arm 154.

Figure 23D:
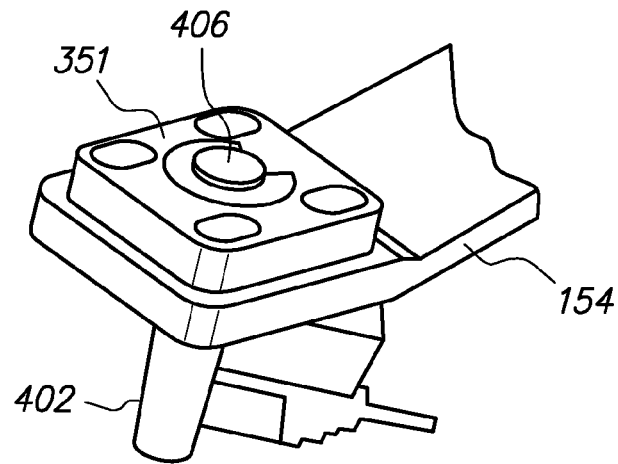

To the sample arm 154 is attached a pipette connector 402, as shown in FIGS. 23C and 23D, through a connector head 351. The lower end 404 of the pipette connector 402 is configured to attach to a pipette 352, such as a disposable plastic pipette, as shown in FIG. 23B. A spring 354 dampens the pressure on the pipette connector 402 when a pipette 352 is being attached thereto.

To the sample arm 154 are also attached a plurality of valves 356, such as solenoid valves. A plurality of tubes 358 connect at one end to the valves 356 and at the other end to sources of reagents 156. A plurality of tubes, not shown, connect the valves 356 to the upper end 406 of the pipette connector 402 when the pipette connector 402 is placed on the sample arm 154. The tubes, which are a vacuum tube and other reagent tubes, operate in a similar manner as described above.

A vial holder block 164 is located on the processing station 150. The vial holder block 164 (FIG. 25), is configured to hold a vial in the opening 552. The vial, not shown, typically contains a biological sample. The biological sample comprises cells that are to be embedded in wax. The vial holder block 164 comprises holes or openings 554, which are configured to allow a screw to pass through to fasten the vial holder block 164 to the frame 152. The block 164 also comprises an opening 556 configured to hold a pipette tip. The block 164 further comprises a purge opening 558, which in some embodiments is connected to the waste disposal unit, discussed below. In some embodiments, the sample arm 154 obtains a pipette tip. The distal end of the pipette tip is lowered into the biological sample solution within a vial placed in the opening 552. Vacuum is applied to the interior of the pipette tip, which causes aspiration of some of the sample solution to enter the pipette tip. In some embodiments, the sample arm 154 removes the pipette tip from the biological solution and transfers it to the purge opening 558, where the biological sample within the pipette tip is forced out of the pipette tip and into the purge opening 558. The process of obtaining a sample and purging it may be repeated more times. This process lowers the risk that the biological sample within the pipette tip would be contaminated by any contaminants inadvertently present in the pipette tip.

Figure 28:
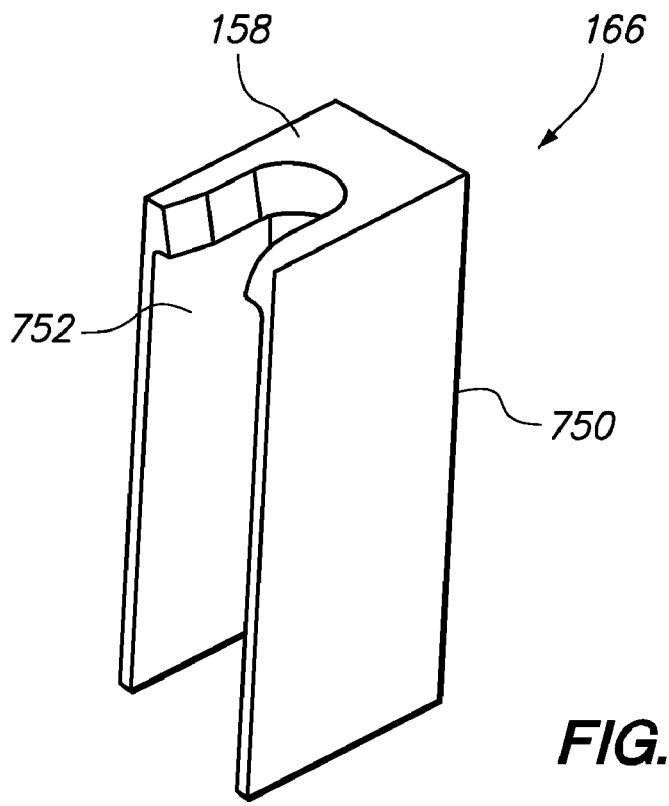
FIG. 28 is a representation of another embodiment of a pipette tip removal post to which a pipette tip removal knife is attached.

It is also envisioned that any time the pipette tip is to be rinsed, or the contents thereof purged, the contents of the pipette tip can be emptied into the purge opening 558. This includes any time the pipette tip is to be washed between the use of the various reagents. The processing station 150 also comprises a pipette tip removal element. The pipette tip removal element comprises a pipette removal element 166, also shown in FIG. 28. The pipette tip removal element 166 comprises a pipette removal post 750 and a pipette removal knife 158. In some embodiments, the pipette removal post 750 and the pipette tip removal knife 158 are molded together as one piece. In other embodiments, the pipette tip removal knife 158 is a separate unit from the pipette tip removal post 750. In these embodiments, the pipette tip removal knife 158 is mounted on top of the pipette tip removal post 752. The pipette tip removal knife 158 comprises a flared opening 752, which operates in a similar manner as the flared opening 702, discussed above. A wax station (not shown) identical to that shown in FIGS. 10A-C is also provided.

Figure 30A:
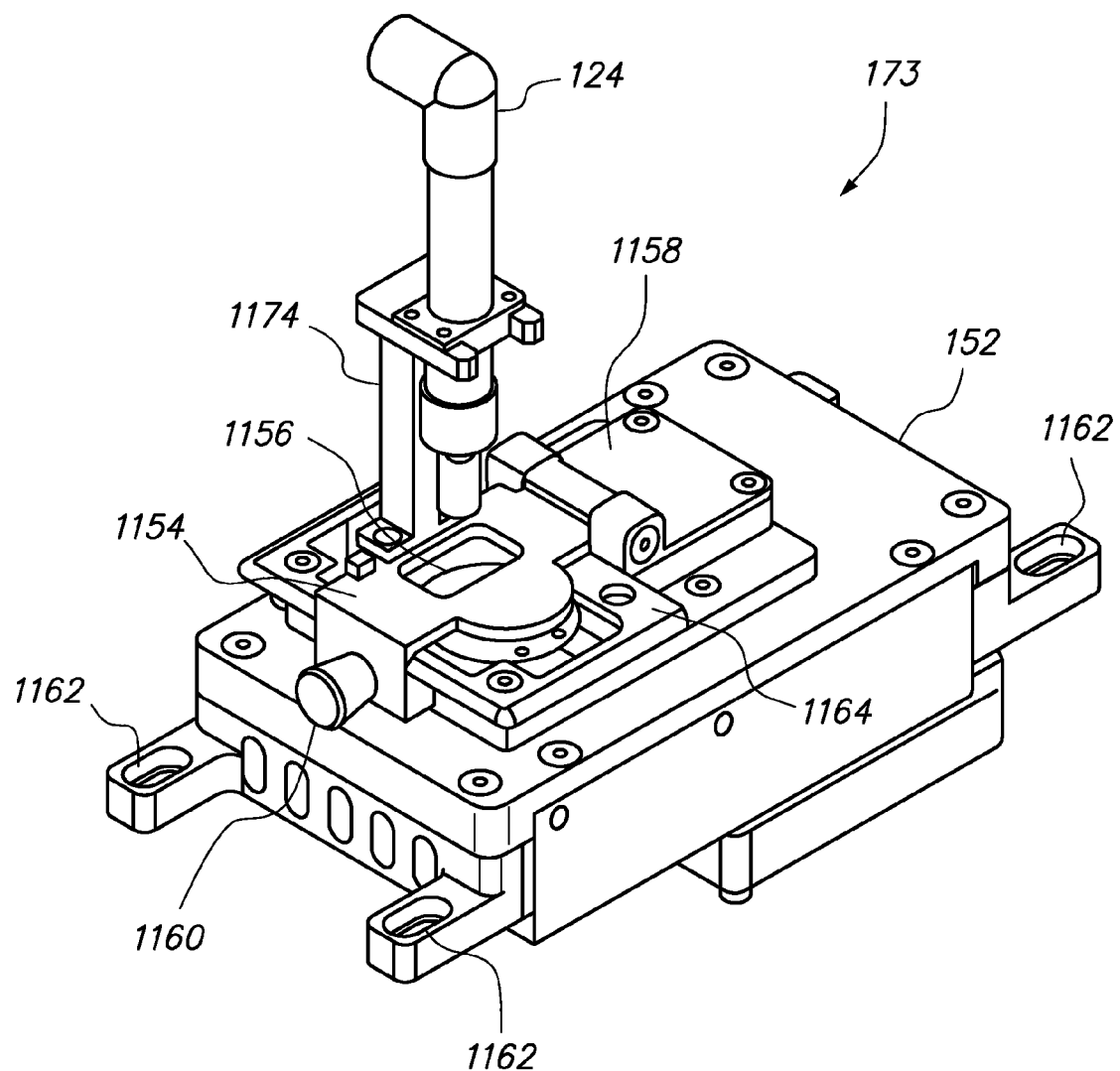
FIG. 30A is a representation of an embodiment of a sample platform.
Figure 30B:
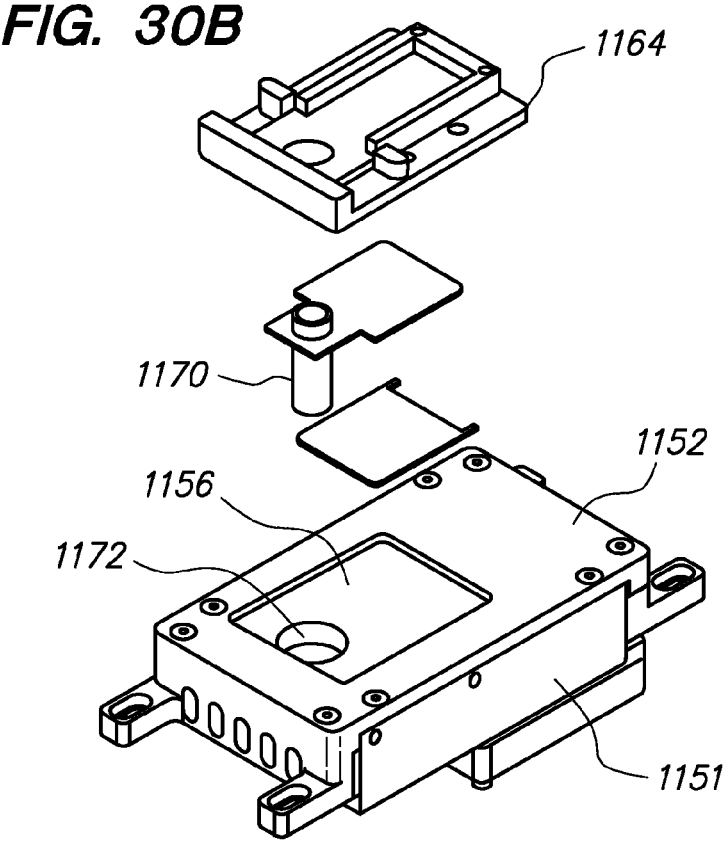
FIG. 30B is an exploded representation of an embodiment of a heat engine with a sample platform.

The processing station 100 also comprises a sample platform 173 (FIG. 30A). In some embodiments, the sample platform 153 is mounted over a thermal engine 1151 (FIG. 30B). A top plate 1152 covers the thermal engine 1151. A waste tube 1170 is placed in an opening 1172 of the thermal engine 1151, which allows for the waste from the preparing the sample in the cassette to flow to the waste disposal unit, discussed below. A cassette holder 1164 is configured to be placed in the opening 1156 of the top plate 1152, over the waste tube 1170. The cassette holder 1164 is configured to hold the cell block cassette and filter assembly 11. The cassette holder 1164 is held in place further by a hinged cover 1154. The hinged cover 1154 is attached at one end to a hinge 1158, which in turn is connected to the top plate 1152. At the other end, the hinged cover 1154 is held in place by a knob 1160 attached to a screw (not shown). To place a cassette on the sample platform 173, the knob 1160 is turn to loosen the screw. The hinged cover 1154 is turned upward about the hinge 1158.

Figure 30C:
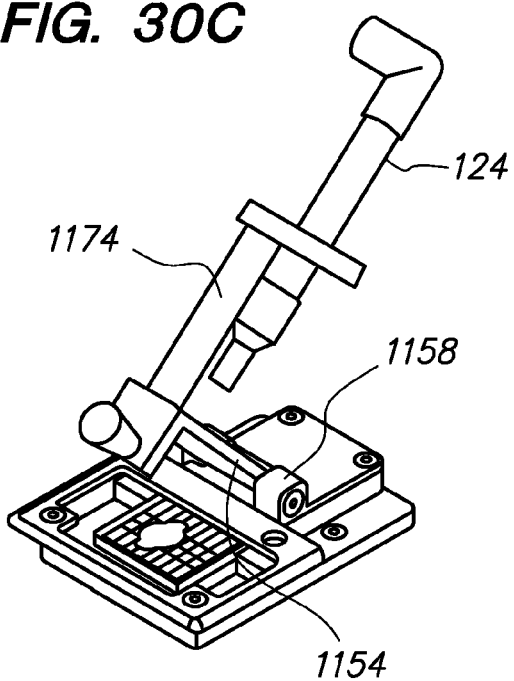
FIG. 30C is a representation of another embodiment of a sample platform.

FIG. 30C shows the configuration of the hinged cover 1154, with the sensor 124, discussed below, attached, when the hinged cover 1154 is turned upward about the hinge 1158. The cassette is then placed in the cassette holder 1164. The hinged cover 1154 is then turned downward about the hinge 1158 and is secured in place by turning the knob 1160. The sample platform 173 comprises holes or openings 1162, which are configured to allow a screw to pass through to fasten the sample platform 173 to the frame 152. A sensor 124 is provided, which measures the level of liquid in the cassette collection well, for example, using ultrasound wave energy, as is done in the ML series of sensors produced by Cosense, or by a Baumer Ultrasonic Level Sensor with beam columnator, such as UNAM 12U9914/S14D. The sensor 124 is held in place by a sensor arm 1174.

The processing station 150 also comprises a touch screen display 174. The touch screen display 174 is electronically coupled to the other components in the system and allows the user to select which reagents to use, the amount of reagents to be used, the order by which the reagents are used, and other functional elements of using the processing station 150.

A further aspect is directed to a heated waste evacuation system, apparatus and method for controllably and safely evacuating flammable liquid and solid waste that is generated during cell block processing. According to one embodiment, an apparatus for evacuating cell block processing waste includes a heated valve, such as a heated ball valve, that is positioned below a reservoir that collects waste. The valve can be heated by one or more heating elements, such as cartridge heaters. According to another embodiment, an apparatus for evacuating cell block processing waste includes a combination of heated valve and a heated reservoir. The heated valve can be heated by one or more heating elements, such as cartridge heaters. The reservoir can be heated by a heating element, such as a foil heater. The valve can be controllably opened and closed to allow liquid and solid waste and mixtures thereof to be collected, heated and released. Heating waste components ensures that solids, such as paraffin wax, remain molten or partially molten to facilitate waste disposal in a controlled and efficient manner.

More particularly, referring to FIGS. 35-38, a waste evacuation system 2800 includes a reservoir or housing 2802 that defines a waste collection area 2804 therein. Solid and liquid waste (such as wax, xylene, alcohol and mixtures thereof) pass from a cell block engine 2803, through a waste tube, such as waste tube 1170, and into the waste collection area 2804. Cell block engine 2803 generally refers to the unit or components that generate a cell-bearing block. Waste can be collected from the cell block engine 2803 by gravity and also by vacuum, which can be supplied via vacuum port 2806.

Figure 35:
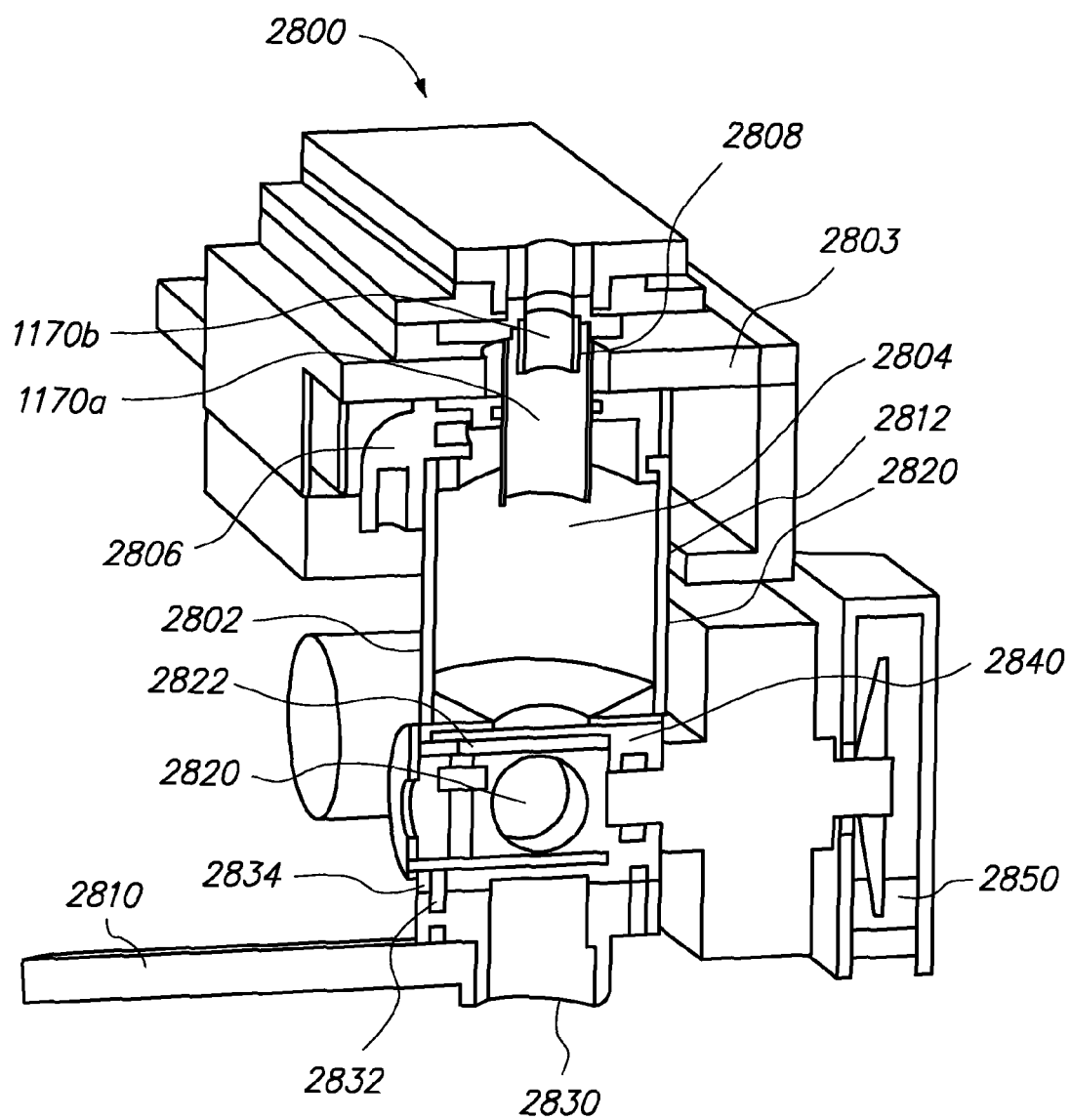
FIG. 35 is a representation of a waste evacuation system according to one embodiment that includes a heated valve and a heated reservoir.
Figure 36:
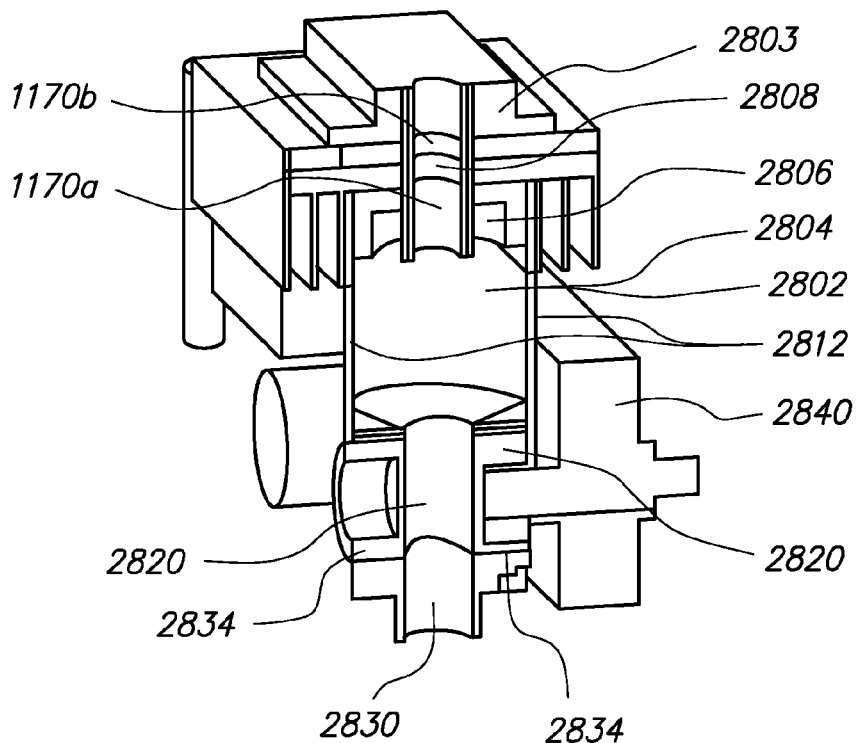
FIG. 36 is a further representation of a waste evacuation system
Figure 37:
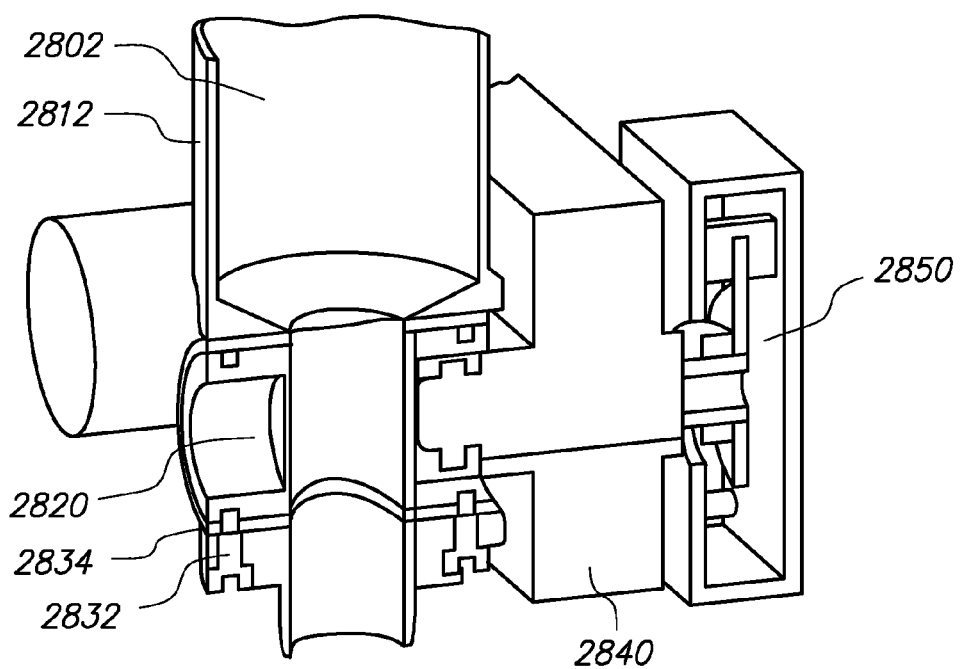
FIG. 37 is a more detailed representation of a heated valve.
Figure 38:
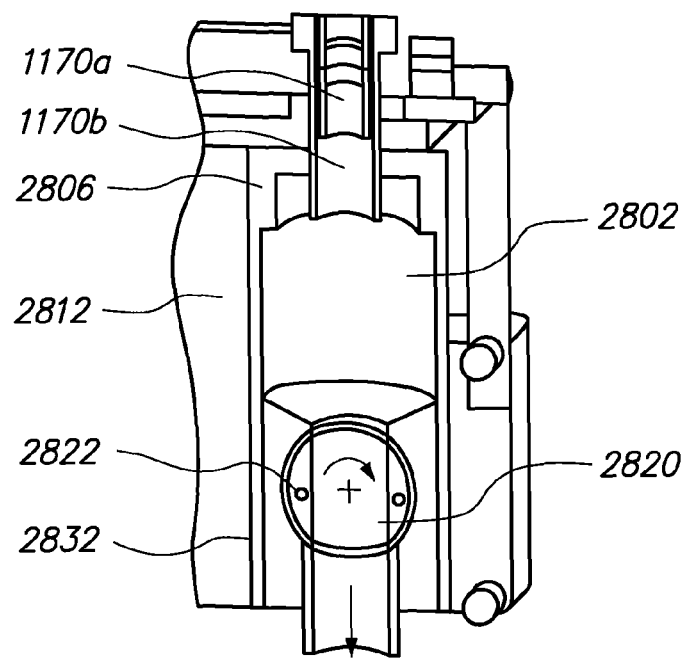
FIG. 38 is a representation further showing heated reservoir and heated valve components of an evacuation system.

In the illustrated embodiment, the waste tube 1170 includes two tubes —an outer tube 1170a and an inner tube 1170b. The bottom edge 2808 of the inner tube 1170b defines a waste drip-edge 2808. The inner tube 1170b allows waste from the cell block engine 2803 to drip from the knife edge, and the outer tube 1170a prevents falling waste from being drawn into the vacuum. In the illustrated embodiment, the outer tube 1170a extends downwardly into the reservoir 2802 further than the inner tube 1170b. The tubes 1170a and 1170b can be concentrically arranged in a dual tube configuration as shown in FIG. 35. The reservoir 2802 that holds the waste can be, for example, a single body housing made of 6061 anodized aluminum.

A heating element 2812 is applied to or around the reservoir 2802 to heat the waste held in the collection area 2804. For example, according to one embodiment, a foil heater 2812, such as a Minco foil heater, is wrapped around the reservoir 2802. An undercut can be added to position the foil heater 2812 as necessary. The foil 2812 heats solids such as paraffin wax to maintain the solids in a molten or semi-molten state. This prevents wax from building up on the interior walls of the chamber of the valve 2820.

The bottom of the reservoir 2820 is connected to a top of the valve 2820. According to one embodiment, the valve 2820 can be a ball valve. The valve 2820 can have a single body design to minimize leak paths. A heating element 2822 is applied to the valve 2820 to facilitate evacuation of waste from the reservoir 2802 above. In one embodiment, the heating element 2822 is in direct contact with the valve 2820. For example, in one embodiment, a cartridge heater 2822 is applied to the valve 2820 to heat the valve 2820 by conduction.

In this embodiment, holes can be formed through the valve 2820 near the edges of the throat of the valve 2820 (as shown in the cut-away view of the valve 2820 in FIG. 35). The cartridge heater 2822, which can be an elongated pencil-like member, can be inserted into the holes and into the valve 2820. Exemplary cartridge heaters 2822 that can be used include cartridge heaters that are used for injection molding. For example, an exemplary cartridge heater 2822 is a FIREROD cartridge heater having a diameter of about 0.125". The cartridge heater 2822 is heated using electric current. Exemplary cartridge heater 2822 settings include can be 48 VAC and 80 watts. Other voltage levels can be used if desired, such as 115 VAC. In the illustrated embodiment, the cartridge heater 2822 includes two heating elements, one extending above the throat of the valve 2820, the other extending below the throat. A resistance temperature detector (RTD) monitor can be used to monitor the heat of the cartridge heater 2822. Persons skilled in the art will appreciate that other heating elements 2822, and manners of applying heating elements 2822 to or into the valve 2820 can be utilized.

By directly contacting and heating the valve 2820, a cartridge heater 2822 can heat waste promptly and act as a "hot plate" when the valve 2820 is in the closed position. The valve 2820 is advantageously heated so that the waste passing through the valve 2820 remains heated. This is particularly advantageous for paraffin wax waste, which can begin to solidify shortly after heat is not applied to wax. For example, paraffin wax can have a melting point of about 55°, and the heating element of the reservoir 2802 and/or the valve 2820 can set to heat the interior of the reservoir 2802 and/or valve 2820 to a temperature above this melting point to maintain the solid paraffin wax and liquids or mixtures thereof in a semi-molten or molten state.

The bottom of the valve 2820 is connected to a waste exit chamber 2830. The waste exits the evacuation system 2800 via the chamber 2830 and into a storage receptacle. The valve 2820 is connected to the chamber 2830 via screws 2832 and a seal sleeve or liner 2834. The liner 2834 provides a seal between the valve 2820 and the waste exit chamber 2830. For this purpose, the bottom of the valve 2820 can have a flexure to clamp to the liner 2834. The sealing material of the liner 2834 can be PFA (Perfluoroalkoxy). Alternatively, the liner 2834 material can be PTFE Teflon. The screws 2832 prevent the liner 2834 from rotating or translating and to prevent the valve 2820 from translating. The screws 2832 also make it easy to change the liner 2834 if the liner 2834 should need replacing. A waste handle 2810 extends from the area below the valve 2820 adjacent to the waste exit chamber 2830.

According to one embodiment, solid and liquid waste accumulates in the reservoir 2802 when the valve 2820 is closed. Vacuum is applied via port 2806 to draw waste from the cell block engine 2803 until processing of a cell block is complete, after which a chill or cooling cycle is initiated. While the cell block is cooling, the waste can be heated, e.g., to 60° C. Prior to opening the valve 2820, the valve 2820 and/or valve body can be heated, e.g., at 70° C. for about two minutes or other suitable time. Different temperatures and heating durations can be utilized as necessary to achieve the desired level of heating.

A motor or other actuator 2840 is then activated to open the valve 2820. One exemplary motor 2840 includes a ³⁄₁₆" cross-pin/½" drive shaft and a maximum torque of about 500 in-lbs (without pin yield). The motor 2840 stall torque can be about 300 in-lbs. The valve 2820 can be actuated with about 50 in-lbs (max). The valve 2820 can be rotated by direct drive from the motor 2840. Exemplary motors 2840 include a 12 Volt, 1.2 Amp, 300 in-lb Brush DC Gearmotor. Persons skilled in the art will appreciate that various motors and motor parameters and configurations can be utilized with embodiments.

As a result of opening the valve 2820, the solid/liquid waste is evacuated from the waste collection area 2804, through the valve 2820, through the waste exit chamber 2830, and into collection receptacle or waste tank positioned below the chamber 2830. For example, the valve 2820 can have a throat having a diameter of about 0.8" through which waste can pass. After evacuating the waste, it is not necessary to continue heating the valve 2820. Thus, the cartridge heater 2822 can be deactivated to stop applying heat to the valve 2820. The valve 2820 is closed, and the system 2800 is ready for preparation of the next cell block, and the above heating and actuation process is repeated as necessary.

Figure 39:
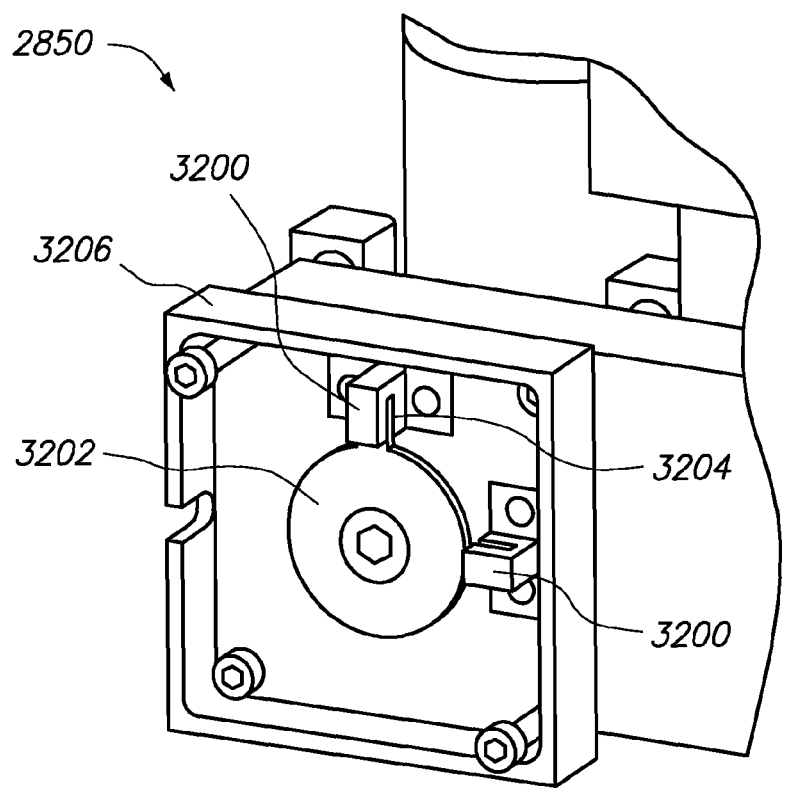
FIG. 39 is a representation of a feedback system to control the positioning and rotation of a valve of a waste evacuation system.

Referring to FIGS. 35 and 39, to ensure that the valve 2820 is opened and closed properly, the rotational position of the valve 2820 can be monitored via a limit switch or feedback system 2850. The output of the feedback system 2850 can be used to control the motor 2840, which opens and closes the valve 2820. In one embodiment, a feedback system 2850 can include one or more sensors 3200. In the illustrated embodiment, the feedback system 2850 includes two Hall Effect sensors 3200 and a wheel 3202. The well 3204 includes a protrusion 3204 extending form the outer edge of the wheel 3202. A housing 3206 encloses and protects the sensors 3200 from waste and other debris.

In the illustrated embodiment, the sensors 3200 are positioned at twelve o'clock and three o'clock positions, i.e., separated by 90 degrees. In one embodiment, the valve 2820 is a ¼ turn valve, as shown in FIG. 35. Thus, at one position, the valve 2820 is closed, and rotating the valve 2820 by 90 degrees opens the valve 2820. For purposes of explanation and illustration, the valve 2820 is closed when the wheel protrusion 3204 is located at the twelve o'clock sensor 3200, and open when the protrusion 3204 is located at the three o'clock sensor 3200.

In use, when the valve 2820 is closed, waste is accumulated in the reservoir 2802, and the motor 2840 can be activated to rotate the valve 2820 to an open position. As the valve 2820 rotates, the wheel 3202 connected thereto also moves from the closed twelve o'clock position to an open three o'clock position. Movement of the valve 2820 is limited by the sensors 3200. More specifically, the protrusion 2304 of the wheel 2302 moving 90 degrees from the twelve o'clock position to the three o'clock position is detected by the second sensor 3200 at three o'clock. In this exemplary configuration, the protrusion 3204 interrupts a signal transmitted between parts of an individual sensor 3200. Upon detecting the protrusion 3204, the second sensor 3200 can generate a signal to deactivate the motor 2840 to limit rotation of the valve 2820 and keep the valve open.

Similarly, when the waste has been evacuated, and the valve 2820 is to be closed, the motor 2840 can be activated to rotate the valve 2820 (which rotates the wheel 3202) back from the three o'clock position to the twelve o'clock position. Movement of the valve 2820 in the opposite direction is limited by the protrusion 3204 of the wheel 3202 moving 90 degrees counterclockwise and being detected by the first sensor 3200 (as a result of an interrupted signal) at the twelve o'clock position. Upon detecting the protrusion 3204, the protrusion interrupts a signal transmitted between parts of the individual sensor at the twelve o'clock position, and in response, this sensor 3200 can generate a signal to deactivate the motor 2840. This limits rotation of the valve 2820 and keeps the valve closed.

Persons skilled in the art will appreciate that different sensors 3200 can be utilized to limit or control movement of the valve 2820. Further, persons skilled in the art will appreciate that different sensor 3200 configurations can be utilized depending on the type of valve 2820 that is utilized and the degree of rotation that is needed to open and close the valve 2820. Further, the feedback system 2850 can be used to limit movement of the valve 2820 between closed and open positions, or between closed and partially open positions as necessary. Thus, the sensors 3200, sensor 3200 configuration and valve 2820 shown in the figures are provided for purposes of explanation and illustration, not limitation.

Figure 40:
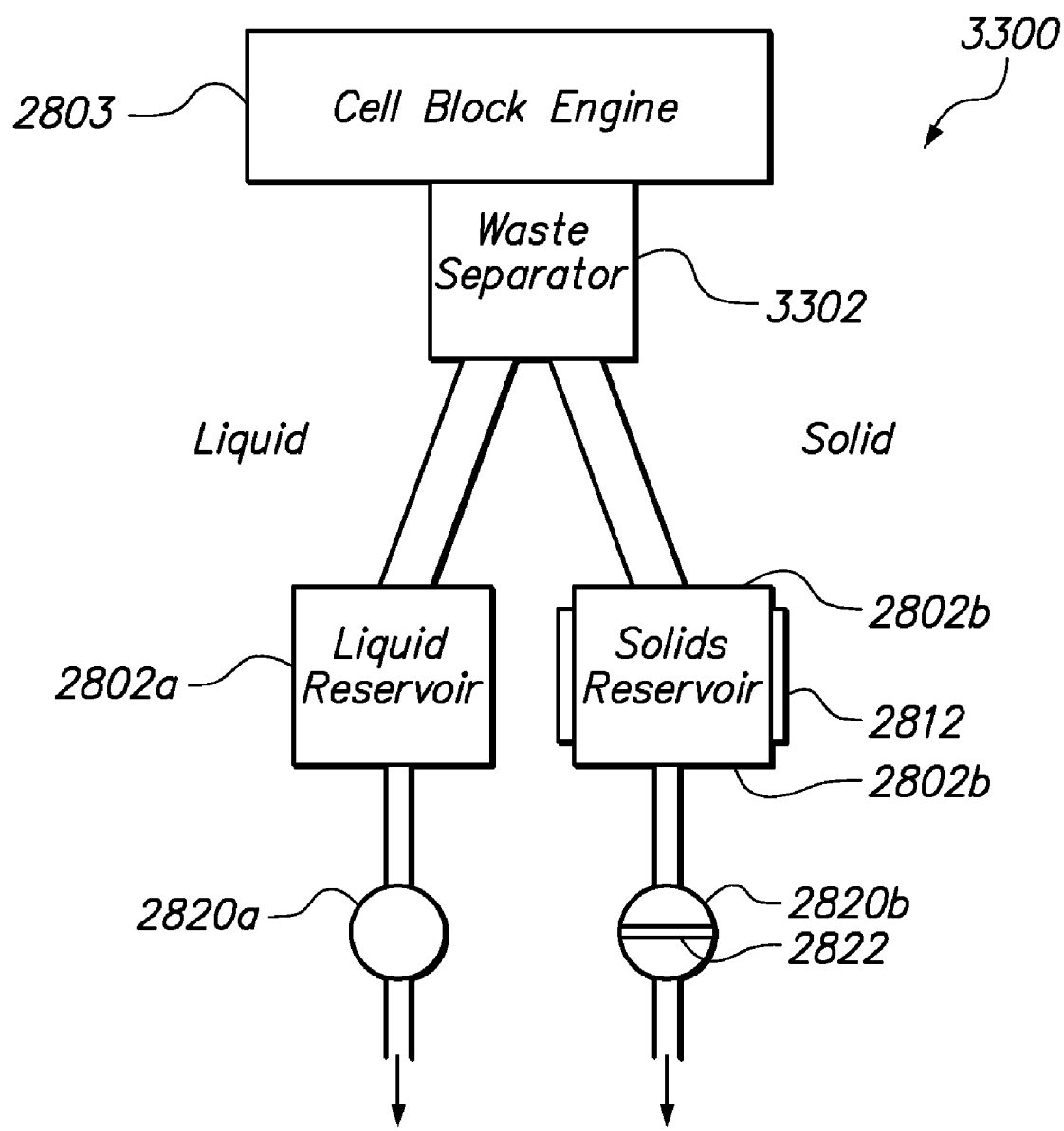
FIG. 40 is a representation of another waste evacuation system that separates and separately processes liquid waste and solid waste generated during cell block processing.

In a further alternative embodiment, FIG. 40 generally illustrates one alternative embodiment of a system 3300 in which solid waste (such as paraffin wax) and liquid waste (such as xylene and alcohol) are separated and separately processed. In the illustrated embodiment, waste that includes a mixture of solids (such as paraffin wax) and liquids (such as xylene and alcohol) can be divided or separated into solid and liquid components by a separator 3302, which outputs liquid waste 3304 and solid waste 3306. Separated liquids 3304 can be stored in a liquid reservoir 2802*a*, and separated solids can be stored in a solids reservoir 2802*b*.

Liquid waste is collected in the liquid reservoir 2802*a* when the valve 2820*a* is closed. Similarly, solid waste is collected in the solids reservoir 3312 when the valve 2820*b* is closed. A foil heater 2812 can be used to apply heat to the solids reservoir 2802*b*, as described with reference to FIGS. 35-38 above. Heat can also be applied to the valve 2820*b* connected to the solids reservoir 2802*b* via a cartridge heater 2822, foil element, or other suitable heating element, as discussed above. Solid waste can then be evacuated from the solids reservoir 2802*b* by opening the heated valve 2820*b*. It may not be necessary to heat the liquid reservoir 2802*a* or the valve 2820*a* positioned below the liquid reservoir 2802*a* since the liquids from cell block processing do not solidify like wax. Thus, in the illustrated embodiment, only the solids reservoir 2802*b* and the valve 2820*b* are heated for evacuating solid waste.

Further, persons skilled in the art will appreciate that in alternative embodiments, the waste evacuation system shown in FIGS. 35-40 can be modified. For example, although the above description refers to a ball valve, or a rotating valve, other embodiments can use other types of valves, such as slide valves. Other alternative embodiments utilize different heating elements. For example, although a valve was described as being heated by a cartridge heater, in an alternative embodiment, a valve can also be heated by a foil heater. Similarly, although the reservoir was described as being heated by a foil heater. Thus, the heating elements used to heat the valve and the reservoir may be the same or different heating elements. Additionally, although embodiments are described in the context of cell block processing, embodiments may be suitable for other applications, such as altering the flow rate of a viscous fluid by application of heat, and reducing friction of a thin film on a surface by application of heat.

The invention may be embodied in other specific forms besides and beyond those described herein. The foregoing embodiments are therefore to be considered in all respects illustrative rather than limiting.

What is claimed is:

1. A cell block cassette and filter assembly, comprising:
   a cell block cassette having a having a collection aperture formed therein, the cell block cassette defining a downward facing annular groove formed in a bottom surface thereof, the groove surrounding the collection aperture; and
   a filter assembly removably attached to the cell block cassette, the filter assembly defining a collection well in communication with the collection aperture, and having a filter positioned across a bottom surface of the collection well, sized to retain cellular matter carried in a fluid dispensed through the collection aperture into the collection well, the filter assembly comprising a base portion and a neck portion extending away from the base portion, the neck portion defining a perimeter of the collection well and having an annular top end that makes an interference fit with the downward facing annular groove located in the bottom surface of the cell block cassette so as to detachably attach the filter assembly to the cell block cassette,
   wherein the collection aperture of the cell block cassette and the collection well of the filter assembly are configured and dimensioned so that liquefied paraffin dispensed therein may solidify to form a solid wax protrusion retained by, and extending beyond the bottom surface of, the cell block cassette when the filter assembly is thereafter detached, with cellular matter previously retained by the filter forming a layer of cells at an outermost end of the wax protrusion.

2. The cell block cassette and filter assembly of claim 1, the filter assembly further comprising a filter support retention portion extending from an underside of the base portion, with a porous filter support member retained therein, the filter being disposed across a top surface of the filter support member within the collection well.

3. The cell block cassette and filter assembly of claim 2, wherein the base portion forms an obtuse angle with the neck portion, and wherein an outermost edge of the base portion extends beyond an outermost edge of the filter support retention portion.

4. The cell block cassette and filter assembly of claim 2, wherein the filter support member is thermally conductive.

5. The cell block cassette and filter assembly of claim 2, wherein the filter support member is selected from a group comprising
   a sintered metal disc,
   a metallic screen, and
   a solid metal disc having one or more drain holes.

6. The cell block cassette and filter assembly of claim 1, the filter comprising pores less than five microns in diameter.

7. The cell block cassette and filter assembly of claim 6, wherein the filter pores are approximately three microns in diameter.

8. The cell block cassette and filter assembly of claim 1, the cell block cassette comprising a substantially planar top surface and a substantially planer bottom surface, the top and bottom surfaces being substantially parallel with one another to allow for stacking of multiple cell block cassettes having their respective filter assemblies removed.

9. A cell block cassette and filter assembly, comprising:
a cell block cassette having a collection aperture formed therein, the cell block cassette defining a downward facing annular groove in a bottom surface thereof, the groove surrounding the collection aperture; and
a filter holder body removably attached to the cell block cassette, the filter holder body defining a collection well in communication with the collection aperture, and having a filter positioned across a bottom surface of the collection well, the filter sized to retain cellular matter carried in a fluid dispensed through the collection aperture, into the collection well, and flowing across the filter, the filter holder body further defining a sealing surface substantially surrounding the collection well,
the filter holder body having a base portion forming the sealing surface and a neck portion extending away from the base portion, the neck portion defining a perimeter of the collection well and having an annular top end that makes an interference fit with the downward facing annular groove located in the bottom surface of the cell block cassette in order to detachably attach the filter holder body to the cell block cassette,
wherein the collection aperture of the cell block cassette and the collection well of the filter holder body are configured and dimensioned so that liquefied paraffin dispensed therein may solidify to form a solid wax protrusion retained by, and extending beyond the bottom surface of, the cell block cassette when the filter assembly is thereafter detached, such that cellular matter previously retained by the filter forms a layer of cells at an outermost end of the wax protrusion.

10. The cell block cassette and filter assembly of claim 9, the filter holder body further comprising a filter support retention portion extending from an underside of the base portion, with a porous filter support member retained therein, the filter being disposed across a top surface of the filter support member within the collection well.

11. The cell block cassette and filter assembly of claim 10, wherein the base portion sealing surface forms an obtuse angle with the neck portion, and wherein an outermost edge of the sealing surface extends beyond an outermost edge of the filter support retention portion.

12. The cell block cassette and filter assembly of claim 10, wherein the filter support member is selected from a group comprising
 a sintered metal disc,
 a metallic screen, and
 a solid metal disc having one or more drain holes.

13. The cell block cassette and filter assembly of claim 9, the cell block cassette comprising a substantially planar top surface and a substantially planer bottom surface, the top and bottom surfaces being substantially parallel with one another to allow for stacking of multiple cell block cassettes having their respective filter holder bodies removed.

14. A cell block cassette and filter assembly, comprising:
a cell block cassette having a collection aperture formed therein, the cell block cassette defining a downward facing annular groove in a bottom surface thereof, the groove surrounding the collection aperture; and
a filter assembly removably attached to the cell block cassette, the filter assembly comprising a filter holder body having
 a neck portion defining a collection well in communication with the collection aperture,
 a base portion defining a sealing surface substantially surrounding the collection well, and
 a filter support retention portion extending from an underside of the base portion, with a porous filter support member retained therein and a filter disposed across a top surface of the filter support member within the collection well, the filter sized to retain cellular matter carried in a fluid dispensed through the collection aperture, into the collection well, and flowing across the filter,
the filter holder neck portion having an annular top end that makes an interference fit with the downward facing annular groove located in the bottom surface of the cell block cassette in order to detachably attach the filter holder to the cell block cassette,
wherein the respective collection aperture of the cell block cassette, and the collection well of the filter assembly are configured and dimensioned so that liquefied paraffin dispensed therein may solidify to form a solid wax protrusion retained by, and extending beyond the bottom surface of, the cell block cassette when the filter assembly is thereafter detached, such that cellular matter previously retained by the filter forms a layer of cells at an outermost end of the wax protrusion.

15. The cell block cassette and filter assembly of claim 14, wherein the base portion sealing surface forms an obtuse angle with the neck portion, and wherein an outermost edge of the sealing surface extends beyond an outermost edge of the filter support retention portion.

16. The cell block cassette and filter assembly of claim 14, wherein the filter support member is selected from a group comprising
 a sintered metal disc,
 a metallic screen, and
 a solid metal disc having one or more drain holes.

17. The cell block cassette and filter assembly of claim 14, the cell block cassette comprising a substantially planar top surface and a substantially planer bottom surface, the top and bottom surfaces being substantially parallel with one another to allow for stacking of multiple cell block cassettes having their respective filter assemblies removed.

\* \* \* \* \*